United States Patent [19]

Bradfield et al.

[11] Patent Number: 5,650,283
[45] Date of Patent: Jul. 22, 1997

[54] BIOLOGICAL ASSAY FOR DETECTING AGONISTS TO THE AH RECEPTOR

[75] Inventors: Christopher A. Bradfield, Chicago; Kristin M. Dolwick, Schaumburg, both of Ill.; Lucy A. Carver, Rolla, Mo.

[73] Assignee: Northwestern University, Evanston, Ill.

[21] Appl. No.: 366,051

[22] Filed: Dec. 29, 1994

Related U.S. Application Data

[63] Continuation-in-part of Ser. No. 45,806, Apr. 8, 1993, Pat. No. 5,378,822.

[51] Int. Cl.$^6$ ........................................ G01N 33/53
[52] U.S. Cl. .......................... 435/7.1; 435/71; 536/73.5
[58] Field of Search ........................ 435/7, 7.1, 69.1, 435/69.7, 252.3, 32.1; 536/23.4, 23.5

[56] References Cited

PUBLICATIONS

Adesnik, M. et al., *Crit. Rev. Biochem*, 1985; 19:247–305.
Alvares, K., et al., *Proc. Natl. Acad. Sci. USA*, 1992; 89:4908–4912.
Becker, D.M., et al., *Methods of Enzymol.*, 1991;194:182–187.
Brunelli, J.P., et al., *Yeast*, 1993:1299–1808.
Carver, L.A., et al., *J. Bio. Chem.*, 269:30109–30112.
Delidow, B.C., et al., *PCR Protocols: Current Methods and Applications*, Humana Press, Totowa, NJ, 1993; vol. 15:1–29.
Dennison, M.S., et al., *Proc. Natl. Acad. Sci. USA*, 1988;85:2528–2532.
Dolwick, K.M., et al., *Mol. Pharmacol*, 1993;44:911–917.
Dolwick, K.M., et al., *Proc. Natl. Acad. Sci. USA*, 1993;90:8566–8570.
Fields, S., et al., *Science*, 1990;29:1046–1047.
Giguere, V., et al., *Cell*, 1986;46:645–652.
Herbomel, P., et al., *Cell*, 1984;39:653–662.
Jain, et al., *J. of Bio. Chem.*, 1994;269:31518–31524.
Knutson, J.C., et al., *Toxicity of Halogenated Hydrocarbons* (Khan, M.A.Q. and Stanton, R.H., eds) Pergamon Press, New York, 1981:187–201.
Lillie, J.W., et al., *Nature*, 1989;338:39–44.
Lindquist, S., et al., *Annu. Rev. Genet.*, 1988;22:631–677.
Lu, A.Y.H., et al., *Pharmacol. Rev.*, 1979;31:277–295.
Ma, J., et al., *Cell*, 1987;50:137–142.
Morin, P.J., et al., *Nucleic Acid Res.*, 1990;20:2453–2458.
Picard, D., et al., *Gene*, 1990;86:257–261.
Picard, D., et al., *Nature*, 1990;348:166–168.
Poland, A., et al., *Mol. Pharm.* 1994;46:915–921.
Poon, D., et al., *Mol. Cell. Biol.* 1991;11:4809–4821.
Ptastine, M., et al., *Nature*, 1988;335:683–689.
Schiestl, R.H., et al., *Curr. Genet.*, 1989;16:339–346.
Triezenberg, S. J. et al., *Genes & Dev.*, 1988;2:718–729.
Van Doren, K., et al., *J. Virol.*, 1984;50:606–614.
Ema et al., *Biochem. Biophys. Res. Comm.* 184(1): 246–253, 15 Apr. 1992.
Mak et al, *J. Biol. Chem.* 264(36):21613–21618, 25 Dec. 1989.
Hoffman et al., *Science* 252:954–958, 17 May 1991.

*Primary Examiner*—John Ulm
*Attorney, Agent, or Firm*—Dressler, Rockey, Milnamov & Katz

[57] ABSTRACT

Murine and human Ah receptor cDNAs are provided. These molecules can be used to generate large quantities of Ah-receptor protein. The Ah receptor can be inserted into cell systems such as yeast or mammalian, expressed, and used in assays to detect agonists to the Ah receptor. The Ah receptor inserted into such systems can be either the full Ah receptor, the receptor containing deletions at its amino and carboxyl ends, or a chimeric receptor. The chimeric Ah receptor has its binding and dimerization domains replaced with an analogous region from another binding protein.

17 Claims, 16 Drawing Sheets

Fig. 6B

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 3207 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..2415

( x i ) SEQUENCE DESCRIPTION: SEQ ID NO:1:

```
ATG AGC AGC GGC GCC AAC ATC ACC TAT GCC AGC CGC AAG CGG CGC AAG    48
Met Ser Ser Gly Ala Asn Ile Thr Tyr Ala Ser Arg Lys Arg Arg Lys
 1               5                  10                  15

CCG GTG CAG AAA ACA GTA AAG CCC ATC CCC GCT GAA GGA ATT AAG TCA    96
Pro Val Gln Lys Thr Val Lys Pro Ile Pro Ala Glu Gly Ile Lys Ser
             20                  25                  30

AAT CCT TCT AAG CGA CAC AGA GAC CGG CTG AAC ACA GAG TTA GAC CGC   144
Asn Pro Ser Lys Arg His Arg Asp Arg Leu Asn Thr Glu Leu Asp Arg
         35                  40                  45

CTG GCC AGC CTG CTG CCC TTC CCG CAA GAT GTT ATT AAT AAG CTG GAC   192
Leu Ala Ser Leu Leu Pro Phe Pro Gln Asp Val Ile Asn Lys Leu Asp
     50                  55                  60

AAA CTC TCT GTT CTT AGG CTC AGC GTC ACG TAC CTG AGG GCC AAG AGC   240
Lys Leu Ser Val Leu Arg Leu Ser Val Thr Tyr Leu Arg Ala Lys Ser
 65                  70                  75                  80

TTC TTT GAT GTT GCA TTA AAG TCC ACC CCT GCT GAC AGA AAT GGA GGC   288
Phe Phe Asp Val Ala Leu Lys Ser Thr Pro Ala Asp Arg Asn Gly Gly
                 85                  90                  95

CAG GAC CAG TGT AGA GCA CAA ATC AGA GAC TGG CAG GAT TTG CAA GAA   336
Gln Asp Gln Cys Arg Ala Gln Ile Arg Asp Trp Gln Asp Leu Gln Glu
            100                 105                 110

GGA GAG TTC TTG TTA CAG GCG CTG AAT GGC TTT GTG CTG GTT GTC ACA   384
Gly Glu Phe Leu Leu Gln Ala Leu Asn Gly Phe Val Leu Val Val Thr
        115                 120                 125

GCA GAT GCC TTG GTC TTC TAT GCT TCC TCC ACT ATC CAA GAT TAC CTG   432
Ala Asp Ala Leu Val Phe Tyr Ala Ser Ser Thr Ile Gln Asp Tyr Leu
    130                 135                 140

GGC TTT CAG CAG TCT GAT GTC ATC CAT CAG AGC GTA TAT GAG CTC ATC   480
```

```
Gly Phe Gln Gln Ser Asp Val Ile His Gln Ser Val Tyr Glu Leu Ile
145                 150                 155                 160

CAT ACA GAA GAC CGG GCG GAA TTC CAG CGC CAG CTT CAC TGG GCT CTA    528
His Thr Glu Asp Arg Ala Glu Phe Gln Arg Gln Leu His Trp Ala Leu
                165                 170                 175

AAC CCA GAC TCT GCA CAA GGA GTG GAC GAA GCC CAT GGC CCT CCA CAG    576
Asn Pro Asp Ser Ala Gln Gly Val Asp Glu Ala His Gly Pro Pro Gln
            180                 185                 190

GCA GCA GTC TAT TAT ACC CCA GAC CAG CTT CCT CCA GAG AAC GCT TCT    624
Ala Ala Val Tyr Tyr Thr Pro Asp Gln Leu Pro Pro Glu Asn Ala Ser
        195                 200                 205

TTC ATG GAG AGG TGC TTC AGG TGC CGG CTG AGG TGC CTG CTG GAT AAT    672
Phe Met Glu Arg Cys Phe Arg Cys Arg Leu Arg Cys Leu Leu Asp Asn
    210                 215                 220

TCA TCT GGT TTT CTG GCA ATG AAT TTC CAA GGG AGG TTA AAG TAT CTT    720
Ser Ser Gly Phe Leu Ala Met Asn Phe Gln Gly Arg Leu Lys Tyr Leu
225                 230                 235                 240

CAT GGA CAG AAC AAG AAA GGG AAG GAC GGA GCG CTG CTT CCT CCA CAA    768
His Gly Gln Asn Lys Lys Gly Lys Asp Gly Ala Leu Leu Pro Pro Gln
                245                 250                 255

CTG GCT TTG TTT GCA ATA GCT ACT CCA CTT CAG CCA CCC TCC ATC CTG    816
Leu Ala Leu Phe Ala Ile Ala Thr Pro Leu Gln Pro Pro Ser Ile Leu
                260                 265                 270

GAA ATT CGA ACC AAA AAC TTC ATC TTC AGG ACC AAA CAC AAG CTA GAC    864
Glu Ile Arg Thr Lys Asn Phe Ile Phe Arg Thr Lys His Lys Leu Asp
            275                 280                 285

TTC ACA CCT ATT GGT TGT GAT GCC AAA GGG CAG CTT ATT CTG GGC TAT    912
Phe Thr Pro Ile Gly Cys Asp Ala Lys Gly Gln Leu Ile Leu Gly Tyr
        290                 295                 300

ACA GAA GTA GAG CTG TGC ACA AGA GGA TCG GGG TAC CAG TTC ATC CAT    960
Thr Glu Val Glu Leu Cys Thr Arg Gly Ser Gly Tyr Gln Phe Ile His
305                 310                 315                 320

GCT GCA GAC ATA CTT CAC TGT GCA GAA TCC CAC ATC CGC ATG ATT AAG    1008
Ala Ala Asp Ile Leu His Cys Ala Glu Ser His Ile Arg Met Ile Lys
                325                 330                 335

ACT GGA GAA AGT GGC ATG ACA GTT TTC CGG CTT CTT GCA AAA CAC AGT    1056
Thr Gly Glu Ser Gly Met Thr Val Phe Arg Leu Leu Ala Lys His Ser
                340                 345                 350

CGC TGG AGG TGG GTC CAG TCC AAT GCA CGC TTG ATT TAC AGA AAT GGA    1104
Arg Trp Arg Trp Val Gln Ser Asn Ala Arg Leu Ile Tyr Arg Asn Gly
            355                 360                 365

AGA CCA GAT TAC ATC ATC GCC ACT CAG AGA CCA CTG ACG GAT GAA GAA    1152
Arg Pro Asp Tyr Ile Ile Ala Thr Gln Arg Pro Leu Thr Asp Glu Glu
        370                 375                 380

GGA CGA GAG CAT TTA CAG AAG CGA AGT ACG TCG CTG CCC TTC ATG TTT    1200
Gly Arg Glu His Leu Gln Lys Arg Ser Thr Ser Leu Pro Phe Met Phe
385                 390                 395                 400

GCT ACC GGA GAG GCT GTG TTG TAC GAG ATC TCC AGC CCT TTC TCT CCC    1248
Ala Thr Gly Glu Ala Val Leu Tyr Glu Ile Ser Ser Pro Phe Ser Pro
                405                 410                 415

ATA ATG GAT CCC CTA CCA ATA CGC ACC AAA AGC AAC ACT AGC AGG AAA    1296
Ile Met Asp Pro Leu Pro Ile Arg Thr Lys Ser Asn Thr Ser Arg Lys
                420                 425                 430

GAC TGG GCT CCC CAG TCA ACC CCA AGT AAG GAT TCT TTC CAC CCC AGT    1344
Asp Trp Ala Pro Gln Ser Thr Pro Ser Lys Asp Ser Phe His Pro Ser
            435                 440                 445

TCT CTT ATG AGT GCC CTC ATC CAG CAG GAT GAG TCC ATC TAT CTG TGT    1392
Ser Leu Met Ser Ala Leu Ile Gln Gln Asp Glu Ser Ile Tyr Leu Cys
        450                 455                 460

CCT CCT TCA AGC CCT GCG CTG TTA GAC AGC CAT TTT CTC ATG GGC TCC    1440
```

-continued

```
          Pro Pro Ser Ser Pro Ala Leu Leu Asp Ser His Phe Leu Met Gly Ser
          465             470             475             480

GTG AGC AAG TGC GGG AGT TGG CAA GAC AGC TTT GCG GCC GCA GGA AGT      1488
Val Ser Lys Cys Gly Ser Trp Gln Asp Ser Phe Ala Ala Ala Gly Ser
                485             490             495

GAG GCT GCG CTG AAA CAT GAG CAA ATT GGC CAT GCT CAG GAC GTG AAC      1536
Glu Ala Ala Leu Lys His Glu Gln Ile Gly His Ala Gln Asp Val Asn
            500             505             510

CTT GCA CTC TCT GGC GGC CCC TCA GAG CTC TTT CCG GAT AAT AAA AAT      1584
Leu Ala Leu Ser Gly Gly Pro Ser Glu Leu Phe Pro Asp Asn Lys Asn
            515             520             525

AAT GAC TTG TAC AGC ATC ATG AGG AAC CTT GGG ATT GAT TTT GAA GAT      1632
Asn Asp Leu Tyr Ser Ile Met Arg Asn Leu Gly Ile Asp Phe Glu Asp
            530             535             540

ATC AGA AGC ATG CAG AAC GAG GAG TTC TTC AGA ACT GAC TCC ACC GCT      1680
Ile Arg Ser Met Gln Asn Glu Glu Phe Phe Arg Thr Asp Ser Thr Ala
545             550             555             560

GCT GGT GAG GTT GAC TTC AAA GAC ATC GAC ATA ACG GAC GAA ATC CTG      1728
Ala Gly Glu Val Asp Phe Lys Asp Ile Asp Ile Thr Asp Glu Ile Leu
                565             570             575

ACC TAC GTG CAG GAT TCC CTG AAC AAT TCA ACT TTG CTG AAC TCG GCT      1776
Thr Tyr Val Gln Asp Ser Leu Asn Asn Ser Thr Leu Leu Asn Ser Ala
            580             585             590

TGC CAG CAG CAG CCT GTG ACT CAG CAC CTA AGC TGT ATG CTG CAG GAG      1824
Cys Gln Gln Gln Pro Val Thr Gln His Leu Ser Cys Met Leu Gln Glu
            595             600             605

CGC CTG CAA CTA GAG CAA CAG CAA CAG CTT CAG CAG CCC CCG CCG CAG      1872
Arg Leu Gln Leu Glu Gln Gln Gln Gln Leu Gln Gln Pro Pro Pro Gln
            610             615             620

GCT CTG GAG CCC CAG CAG CAG CTG TGT CAG ATG GTG TGC CCC CAG CAA      1920
Ala Leu Glu Pro Gln Gln Gln Leu Cys Gln Met Val Cys Pro Gln Gln
625             630             635             640

GAT CTG GGT CCG AAG CAC ACG CAA ATC AAC GGC ACG TTT GCA AGT TGG      1968
Asp Leu Gly Pro Lys His Thr Gln Ile Asn Gly Thr Phe Ala Ser Trp
                645             650             655

AAC CCC ACC CCT CCC GTG TCT TTC AAC TGT CCC CAG CAG GAA CTA AAG      2016
Asn Pro Thr Pro Pro Val Ser Phe Asn Cys Pro Gln Gln Glu Leu Lys
            660             665             670

CAC TAT CAG CTC TTT TCC AGC TTA CAG GGG ACT GCT CAG GAA TTT CCC      2064
His Tyr Gln Leu Phe Ser Ser Leu Gln Gly Thr Ala Gln Glu Phe Pro
            675             680             685

TAC AAA CCA GAG GTG GAC AGT GTG CCT TAC ACA CAG AAC TTT GCT CCC      2112
Tyr Lys Pro Glu Val Asp Ser Val Pro Tyr Thr Gln Asn Phe Ala Pro
            690             695             700

TGT AAT CAG CCT CTG CTT CCA GAA CAT TCC AAG AGT GTG CAG TTG GAC      2160
Cys Asn Gln Pro Leu Leu Pro Glu His Ser Lys Ser Val Gln Leu Asp
705             710             715             720

TTC CCT GGA AGG GAT TTT GAA CCG TCC CTG CAT CCC ACT ACT TCT AAT      2208
Phe Pro Gly Arg Asp Phe Glu Pro Ser Leu His Pro Thr Thr Ser Asn
                725             730             735

TTA GAT TTT GTC AGT TGT TTA CAA GTT CCT GAA AAC CAA AGT CAT GGG      2256
Leu Asp Phe Val Ser Cys Leu Gln Val Pro Glu Asn Gln Ser His Gly
            740             745             750

ATA AAC TCA CAG TCC GCC ATG GTC AGT CCT CAG GCA TAC TAT GCT GGG      2304
Ile Asn Ser Gln Ser Ala Met Val Ser Pro Gln Ala Tyr Tyr Ala Gly
            755             760             765

GCC ATG TCC ATG TAT CAG TGC CAG CCA GGG CCA CAG CGC ACC CCT GTG      2352
Ala Met Ser Met Tyr Gln Cys Gln Pro Gly Pro Gln Arg Thr Pro Val
770             775             780

GAC CAG ACG CAG TAC AGC TCT GAA ATT CCA GGT TCT CAG GCA TTC CTA      2400
```

```
                 Asp Gln Thr Gln Tyr Ser Ser Glu Ile Pro Gly Ser Gln Ala Phe Leu
                 785                 790                 795                 800

AGC AAG GTG CAG AGT TGAGGTGTTT TCAATGAAAC CTATTCGTCC GACTTGAGCA         2455
Ser Lys Val Gln Ser
                805

GCATTGGCCA CGCTGCTCAG ACCACTGGCC ATCTCCATCA CTGCGGAAGC CCGGCCTCTT       2515

CCCGATATCA CACCCGGTGG ATTCCTGTAG CTCCCATGCC AGGATGAAAT TCATTCAGGA       2575

ACAGGATACC AGAACTGTGA GGGTTGGACA TCAGTACACT TTCTCCAAAA CAGATTTCGA       2635

TTCTTGTGTT TAGAGAAGGA GTTAAAACC CGTACCTGAG ATGCTCCCTA TACGATGGGA        2695

GAGCTCGGAC GGAGCACATG GGAGGAGTTC AGGCACCTCA GAGTGCACAG TGTTTACTGT       2755

GAAAAATTCT CGGGTTCCCT GCTCAGTAAC TTCAGCAGGA AAACAGGGA GGTATTTGGA        2815

GCTTTGAACT TCTGGATTCT TGTTAGTATA CCAAATACGG AGTTACAGGA CTAACCGATT       2875

TCCTATATTT TTAACCTCT GTTTTGTCC CAGAAGTTAA AGTAAATGGT TTGGTGCTTT         2935

TCTCAAAAGA AAATCTCAAT GCTTTCTTTC TGCACTGTTA ATATAAGTGC CTCACTTTTT       2995

GTTGTTGTTG TTGTTGTTTT CTGATTTTTT TCTTTTTTC TATCTACCTG TAACACAATA       3055

GGGTATGTAT TTTATATGAA ATATTTTTA TCTTTTTTGA ATTAATATTC TTTCTGCACA        3115

AAGAAAGTTT CCCGAATCCC AACCTTTCTA TGACCCCGCT GTGTGTGTGC ACTACTCATC      3175

CTTTCCTTCA GATAAAGAGT AATTGATAAC TC                                    3207
```

( 2 ) INFORMATION FOR SEQ ID NO:2:

( i ) SEQUENCE CHARACTERISTICS:
        ( A ) LENGTH: 805 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Ser Ser Gly Ala Asn Ile Thr Tyr Ala Ser Arg Lys Arg Arg Lys
 1               5                  10                  15

Pro Val Gln Lys Thr Val Lys Pro Ile Pro Ala Glu Gly Ile Lys Ser
                20                  25                  30

Asn Pro Ser Lys Arg His Arg Asp Arg Leu Asn Thr Glu Leu Asp Arg
            35                  40                  45

Leu Ala Ser Leu Leu Pro Phe Pro Gln Asp Val Ile Asn Lys Leu Asp
        50                  55                  60

Lys Leu Ser Val Leu Arg Leu Ser Val Thr Tyr Leu Arg Ala Lys Ser
65                  70                  75                  80

Phe Phe Asp Val Ala Leu Lys Ser Thr Pro Ala Asp Arg Asn Gly Gly
                85                  90                  95

Gln Asp Gln Cys Arg Ala Gln Ile Arg Asp Trp Gln Asp Leu Gln Glu
                100                 105                 110

Gly Glu Phe Leu Leu Gln Ala Leu Asn Gly Phe Val Leu Val Val Thr
            115                 120                 125

Ala Asp Ala Leu Val Phe Tyr Ala Ser Ser Thr Ile Gln Asp Tyr Leu
        130                 135                 140

Gly Phe Gln Gln Ser Asp Val Ile His Gln Ser Val Tyr Glu Leu Ile
145                 150                 155                 160

His Thr Glu Asp Arg Ala Glu Phe Gln Arg Gln Leu His Trp Ala Leu
                165                 170                 175

Asn Pro Asp Ser Ala Gln Gly Val Asp Glu Ala His Gly Pro Pro Gln
            180                 185                 190
```

-continued

| | | | | | | | | | | | | |
|---|---|---|---|---|---|---|---|---|---|---|---|---|
| Ala | Ala | Val 195 | Tyr | Tyr | Thr | Pro | Asp 200 | Gln | Leu | Pro | Pro 205 | Glu | Asn | Ala | Ser |
| Phe | Met 210 | Glu | Arg | Cys | Phe | Arg 215 | Cys | Arg | Leu | Arg | Cys 220 | Leu | Leu | Asp | Asn |
| Ser 225 | Ser | Gly | Phe | Leu | Ala 230 | Met | Asn | Phe | Gln | Arg 235 | Leu | Lys | Tyr | Leu 240 |
| His | Gly | Gln | Asn | Lys 245 | Lys | Gly | Lys | Asp | Gly 250 | Ala | Leu | Leu | Pro | Pro 255 | Gln |
| Leu | Ala | Leu | Phe 260 | Ala | Ile | Ala | Thr | Pro 265 | Leu | Gln | Pro | Pro | Ser 270 | Ile | Leu |
| Glu | Ile | Arg 275 | Thr | Lys | Asn | Phe | Ile 280 | Phe | Arg | Thr | Lys | His 285 | Lys | Leu | Asp |
| Phe | Thr 290 | Pro | Ile | Gly | Cys | Asp 295 | Ala | Lys | Gly | Gln | Leu 300 | Ile | Leu | Gly | Tyr |
| Thr 305 | Glu | Val | Glu | Leu | Cys 310 | Thr | Arg | Gly | Ser | Gly 315 | Tyr | Gln | Phe | Ile | His 320 |
| Ala | Ala | Asp | Ile | Leu 325 | His | Cys | Ala | Glu | Ser 330 | His | Ile | Arg | Met | Ile 335 | Lys |
| Thr | Gly | Glu | Ser 340 | Gly | Met | Thr | Val | Phe 345 | Arg | Leu | Leu | Ala | Lys 350 | His | Ser |
| Arg | Trp | Arg 355 | Trp | Val | Gln | Ser | Asn 360 | Ala | Arg | Leu | Ile | Tyr 365 | Arg | Asn | Gly |
| Arg | Pro 370 | Asp | Tyr | Ile | Ile | Ala 375 | Thr | Gln | Arg | Pro | Leu 380 | Thr | Asp | Glu | Glu |
| Gly 385 | Arg | Glu | His | Leu | Gln 390 | Lys | Arg | Ser | Thr | Ser 395 | Leu | Pro | Phe | Met | Phe 400 |
| Ala | Thr | Gly | Glu | Ala 405 | Val | Leu | Tyr | Glu | Ile 410 | Ser | Ser | Pro | Phe | Ser 415 | Pro |
| Ile | Met | Asp | Pro 420 | Leu | Pro | Ile | Arg | Thr 425 | Lys | Ser | Asn | Thr | Ser 430 | Arg | Lys |
| Asp | Trp | Ala 435 | Pro | Gln | Ser | Thr | Pro 440 | Ser | Lys | Asp | Ser | Phe 445 | His | Pro | Ser |
| Ser | Leu 450 | Met | Ser | Ala | Leu | Ile 455 | Gln | Gln | Asp | Glu | Ser 460 | Ile | Tyr | Leu | Cys |
| Pro 465 | Pro | Ser | Ser | Pro | Ala 470 | Leu | Leu | Asp | Ser | His 475 | Phe | Leu | Met | Gly | Ser 480 |
| Val | Ser | Lys | Cys | Gly 485 | Ser | Trp | Gln | Asp | Ser 490 | Phe | Ala | Ala | Ala | Gly 495 | Ser |
| Glu | Ala | Ala | Leu 500 | Lys | His | Glu | Gln | Ile 505 | Gly | His | Ala | Gln | Asp 510 | Val | Asn |
| Leu | Ala | Leu 515 | Ser | Gly | Gly | Pro | Ser 520 | Glu | Leu | Phe | Pro | Asp 525 | Asn | Lys | Asn |
| Asn | Asp 530 | Leu | Tyr | Ser | Ile | Met 535 | Arg | Asn | Leu | Gly | Ile 540 | Asp | Phe | Glu | Asp |
| Ile 545 | Arg | Ser | Met | Gln | Asn 550 | Glu | Glu | Phe | Phe | Arg 555 | Thr | Asp | Ser | Thr | Ala 560 |
| Ala | Gly | Glu | Val | Asp 565 | Phe | Lys | Asp | Ile | Asp 570 | Ile | Thr | Asp | Glu | Ile 575 | Leu |
| Thr | Tyr | Val | Gln 580 | Asp | Ser | Leu | Asn | Ser 585 | Thr | Leu | Leu | Asn | Ser 590 | Ala |
| Cys | Gln | Gln | Gln 595 | Pro | Val | Thr | Gln 600 | His | Leu | Ser | Cys | Met 605 | Leu | Gln | Glu |
| Arg | Leu | Gln | Leu | Glu | Gln | Gln | Gln | Gln | Leu | Gln | Gln | Pro | Pro | Pro | Gln |

|       |       |       |       |       | 610   |       |       |       |       | 615   |       |       |       |       | 620   |       |       |       |       |
|-------|-------|-------|-------|-------|-------|-------|-------|-------|-------|-------|-------|-------|-------|-------|-------|-------|-------|-------|-------|

Ala Leu Glu Pro Gln Gln Gln Leu Cys Gln Met Val Cys Pro Gln Gln
625                     630                 635                     640

Asp Leu Gly Pro Lys His Thr Gln Ile Asn Gly Thr Phe Ala Ser Trp
                645                 650                 655

Asn Pro Thr Pro Pro Val Ser Phe Asn Cys Pro Gln Gln Glu Leu Lys
            660             665             670

His Tyr Gln Leu Phe Ser Ser Leu Gln Gly Thr Ala Gln Glu Phe Pro
        675             680             685

Tyr Lys Pro Glu Val Asp Ser Val Pro Tyr Thr Gln Asn Phe Ala Pro
    690             695             700

Cys Asn Gln Pro Leu Leu Pro Glu His Ser Lys Ser Val Gln Leu Asp
705             710             715             720

Phe Pro Gly Arg Asp Phe Glu Pro Ser Leu His Pro Thr Thr Ser Asn
            725             730             735

Leu Asp Phe Val Ser Cys Leu Gln Val Pro Glu Asn Gln Ser His Gly
            740             745             750

Ile Asn Ser Gln Ser Ala Met Val Ser Pro Gln Ala Tyr Tyr Ala Gly
        755             760             765

Ala Met Ser Met Tyr Gln Cys Gln Pro Gly Pro Gln Arg Thr Pro Val
    770             775             780

Asp Gln Thr Gln Tyr Ser Ser Glu Ile Pro Gly Ser Gln Ala Phe Leu
785             790             795             800

Ser Lys Val Gln Ser
            805

( 2 ) INFORMATION FOR SEQ ID NO:3:

( i ) SEQUENCE CHARACTERISTICS:
        ( A ) LENGTH: 5261 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 383..2927

( x i ) SEQUENCE DESCRIPTION: SEQ ID NO:3:

```
AATTCCGCAC GGCCCAGACC CAGGATTCTT TATAGACGGC CCAGGCTCCT CCTCCGCCCG    60

GGCCGCCTCA CCTGCGGGCA TTGCGCGCCG CCTCCGCCGG TGTAGACGGC ACCTGCGCCG   120

CCTTGCTCGC GGGTCTCCGC CCTCGCCCAC CCTCACTGCG CCAGGCCCAG GCAGCTCACC   180

TGTACTGGCG CGGGCTGCGG AAGCTGCGTG ACGCGAGGCG TTGAGGCGCG GCGCCCACGC   240

CACTGTCCCG AGAGGACGCA GGTGGAGCGG GCGCGACTTC GCGAACCCGG CGCCGGCCGC   300

CGCAGTGGTC CCAGCCTACA CCGGGTTCCG GGACCCGGC  CGCCAGTGCC CGGGGAGTAG   360

CCGCCGCCGT CGGCTGGGCA CC ATG AAC AGC AGC AGC GCC AAC ATC ACC TAC   412
                        Met Asn Ser Ser Ser Ala Asn Ile Thr Tyr
                        1               5                   10

GCC AGT CGC AAG CGG CGG AAG CCG GTG CAG AAA ACA GTA AAG CCA ATC    460
Ala Ser Arg Lys Arg Arg Lys Pro Val Gln Lys Thr Val Lys Pro Ile
            15                  20                  25

CCA GCT GAA GGA ATC AAG TCA AAT CCT TCC AAG CGG CAT AGA GAC CGA    508
Pro Ala Glu Gly Ile Lys Ser Asn Pro Ser Lys Arg His Arg Asp Arg
                30                  35                  40
```

| | | | | | | | | | | | | | | | | |
|---|---|---|---|---|---|---|---|---|---|---|---|---|---|---|---|---|
| CTT | AAT | ACA | GAG | TTG | GAC | CGT | TTG | GCT | AGC | CTG | CTG | CCT | TTC | CCA | CAA | 556 |
| Leu | Asn | Thr | Glu | Leu | Asp | Arg | Leu | Ala | Ser | Leu | Leu | Pro | Phe | Pro | Gln | |
| | | 45 | | | | 50 | | | | | 55 | | | | | |
| GAT | GTT | ATT | AAT | AAG | TTG | GAC | AAA | CTT | TCA | GTT | CTT | AGG | CTC | AGC | GTC | 604 |
| Asp | Val | Ile | Asn | Lys | Leu | Asp | Lys | Leu | Ser | Val | Leu | Arg | Leu | Ser | Val | |
| | 60 | | | | 65 | | | | | 70 | | | | | | |
| AGT | TAC | CTG | AGA | GCC | AAG | AGC | TTC | TTT | GAT | GTT | GCA | TTA | AAA | TCC | TCC | 652 |
| Ser | Tyr | Leu | Arg | Ala | Lys | Ser | Phe | Phe | Asp | Val | Ala | Leu | Lys | Ser | Ser | |
| 75 | | | | | 80 | | | | | 85 | | | | | 90 | |
| CCT | ACT | GAA | AGA | AAC | GGA | GGC | CAG | GAT | AAC | TGT | AGA | GCA | GCA | AAT | TTC | 700 |
| Pro | Thr | Glu | Arg | Asn | Gly | Gly | Gln | Asp | Asn | Cys | Arg | Ala | Ala | Asn | Phe | |
| | | | | 95 | | | | 100 | | | | | 105 | | | |
| AGA | GAA | GGC | CTG | AAC | TTA | CAA | GAA | GGA | GAA | TTC | TTA | TTA | CAG | GCT | CTG | 748 |
| Arg | Glu | Gly | Leu | Asn | Leu | Gln | Glu | Gly | Glu | Phe | Leu | Leu | Gln | Ala | Leu | |
| | | | 110 | | | | | 115 | | | | | 120 | | | |
| AAT | GGC | TTT | GTA | TTA | GTT | GTC | ACT | ACA | GAT | GCT | TTG | GTC | TTT | TAT | GCT | 796 |
| Asn | Gly | Phe | Val | Leu | Val | Val | Thr | Thr | Asp | Ala | Leu | Val | Phe | Tyr | Ala | |
| | | 125 | | | | | 130 | | | | | 135 | | | | |
| TCT | TCT | ACT | ATA | CAA | GAT | TAT | CTA | GGG | TTT | CAG | CAG | TCT | GAT | GTC | ATA | 844 |
| Ser | Ser | Thr | Ile | Gln | Asp | Tyr | Leu | Gly | Phe | Gln | Gln | Ser | Asp | Val | Ile | |
| | 140 | | | | | 145 | | | | | 150 | | | | | |
| CAT | CAG | AGT | GTA | TAT | GAA | CTT | ATC | CAT | ACC | GAA | GAC | CGA | GCT | GAA | TTT | 892 |
| His | Gln | Ser | Val | Tyr | Glu | Leu | Ile | His | Thr | Glu | Asp | Arg | Ala | Glu | Phe | |
| 155 | | | | | 160 | | | | | 165 | | | | | 170 | |
| CAG | CGT | CAG | CTA | CAC | TGG | GCA | TTA | AAT | CCT | TCT | CAG | TGT | ACA | GAG | TCT | 940 |
| Gln | Arg | Gln | Leu | His | Trp | Ala | Leu | Asn | Pro | Ser | Gln | Cys | Thr | Glu | Ser | |
| | | | | 175 | | | | | 180 | | | | | 185 | | |
| GGA | CAA | GGA | ATT | GAA | GAA | GCC | ACT | GGT | CTC | CCC | CAG | ACA | GTA | GTC | TGT | 988 |
| Gly | Gln | Gly | Ile | Glu | Glu | Ala | Thr | Gly | Leu | Pro | Gln | Thr | Val | Val | Cys | |
| | | | 190 | | | | | 195 | | | | | 200 | | | |
| TAT | AAC | CCA | GAC | CAG | ATT | CCT | CCA | GAA | AAC | TCT | CCT | TTA | ATG | GAG | AGG | 1036 |
| Tyr | Asn | Pro | Asp | Gln | Ile | Pro | Pro | Glu | Asn | Ser | Pro | Leu | Met | Glu | Arg | |
| | | 205 | | | | | 210 | | | | | 215 | | | | |
| TGC | TTC | ATA | TGT | CGT | CTA | AGG | TGT | CTG | CTG | GAT | AAT | TCA | TCT | GGT | TTT | 1084 |
| Cys | Phe | Ile | Cys | Arg | Leu | Arg | Cys | Leu | Leu | Asp | Asn | Ser | Ser | Gly | Phe | |
| | | 220 | | | | 225 | | | | | 230 | | | | | |
| CTG | GCA | ATG | AAT | TTC | CAA | GGG | AAG | TTA | AAG | TAT | CTT | CAT | GGA | CAG | AAA | 1132 |
| Leu | Ala | Met | Asn | Phe | Gln | Gly | Lys | Leu | Lys | Tyr | Leu | His | Gly | Gln | Lys | |
| 235 | | | | | 240 | | | | | 245 | | | | | 250 | |
| AAG | AAA | GGG | AAA | GAT | GGA | TCA | ATA | CTT | CCA | CCT | CAG | TTG | GCT | TTG | TTT | 1180 |
| Lys | Lys | Gly | Lys | Asp | Gly | Ser | Ile | Leu | Pro | Pro | Gln | Leu | Ala | Leu | Phe | |
| | | | | 255 | | | | 260 | | | | | 265 | | | |
| GCG | ATA | GCT | ACT | CCA | CTT | CAG | CCA | CCA | TCC | ATA | CTT | GAA | ATC | CGG | ACC | 1228 |
| Ala | Ile | Ala | Thr | Pro | Leu | Gln | Pro | Pro | Ser | Ile | Leu | Glu | Ile | Arg | Thr | |
| | | | | 270 | | | | 275 | | | | | 280 | | | |
| AAA | AAT | TTT | ATC | TTT | AGA | ACC | AAA | CAC | AAA | CTA | GAC | TTC | ACA | CCT | ATT | 1276 |
| Lys | Asn | Phe | Ile | Phe | Arg | Thr | Lys | His | Lys | Leu | Asp | Phe | Thr | Pro | Ile | |
| | | 285 | | | | | 290 | | | | | 295 | | | | |
| GGT | TGT | GAT | GCC | AAA | GGA | AGA | ATT | GTT | TTA | GGA | TAT | ACT | GAA | GCA | GAG | 1324 |
| Gly | Cys | Asp | Ala | Lys | Gly | Arg | Ile | Val | Leu | Gly | Tyr | Thr | Glu | Ala | Glu | |
| | | 300 | | | | 305 | | | | | 310 | | | | | |
| CTG | TGC | ACG | AGA | GGC | TCA | GGT | TAT | CAG | TTT | ATT | CAT | GCA | GCT | GAT | ATG | 1372 |
| Leu | Cys | Thr | Arg | Gly | Ser | Gly | Tyr | Gln | Phe | Ile | His | Ala | Ala | Asp | Met | |
| 315 | | | | | 320 | | | | | 325 | | | | | 330 | |
| CTT | TAT | TGT | GCC | GAG | TCC | CAT | ATC | CGA | ATG | ATT | AAG | ACT | GGA | GAA | AGT | 1420 |
| Leu | Tyr | Cys | Ala | Glu | Ser | His | Ile | Arg | Met | Ile | Lys | Thr | Gly | Glu | Ser | |
| | | | | 335 | | | | | 340 | | | | | 345 | | |
| GGC | ATG | ATA | GTT | TTC | CGG | CTT | CTT | ACA | AAA | AAC | AAC | CGA | TGG | ACT | TGG | 1468 |
| Gly | Met | Ile | Val | Phe | Arg | Leu | Leu | Thr | Lys | Asn | Asn | Arg | Trp | Thr | Trp | |
| | | | | 350 | | | | | 355 | | | | | 360 | | |

```
GTC CAG TCT AAT GCA CGC CTG CTT TAT AAA AAT GGA AGA CCA GAT TAT       1516
Val Gln Ser Asn Ala Arg Leu Leu Tyr Lys Asn Gly Arg Pro Asp Tyr
    365                 370                 375

ATC ATT GTA ACT CAG AGA CCA CTA ACA GAT GAG GAA GGA ACA GAG CAT       1564
Ile Ile Val Thr Gln Arg Pro Leu Thr Asp Glu Glu Gly Thr Glu His
380                 385                 390

TTA CGA AAA CGA AAT ACG AAG TTG CCT TTT ATG TTT ACC ACT GGA GAA       1612
Leu Arg Lys Arg Asn Thr Lys Leu Pro Phe Met Phe Thr Thr Gly Glu
395                 400                 405                 410

GCT GTG TTG TAT GAG GCA ACC AAC CCT TTT CCT GCC ATA ATG GAT CCC       1660
Ala Val Leu Tyr Glu Ala Thr Asn Pro Phe Pro Ala Ile Met Asp Pro
            415                 420                 425

TTA CCA CTA AGG ACT AAA AAT GGC ACT AGT GGA AAA GAC TCT GCT ACC       1708
Leu Pro Leu Arg Thr Lys Asn Gly Thr Ser Gly Lys Asp Ser Ala Thr
            430                 435                 440

ACA TCC ACT CTA AGC AAG GAC TCT CTC AAT CCT AGT TCC CTC CTG GCT       1756
Thr Ser Thr Leu Ser Lys Asp Ser Leu Asn Pro Ser Ser Leu Leu Ala
        445                 450                 455

GCC ATG ATG CAA CAA GAT GAG TCT ATT TAT CTC TAT CCT GCT TCA AGT       1804
Ala Met Met Gln Gln Asp Glu Ser Ile Tyr Leu Tyr Pro Ala Ser Ser
460                 465                 470

ACT TCA AGT ACT GCA CCT TTT GAA AAC AAC TTT TTC AAC GAA TCT ATG       1852
Thr Ser Ser Thr Ala Pro Phe Glu Asn Asn Phe Phe Asn Glu Ser Met
475                 480                 485                 490

AAT GAA TGC AGA AAT TGG CAA GAT AAT ACT GCA CCG ATG GGA AAT GAT       1900
Asn Glu Cys Arg Asn Trp Gln Asp Asn Thr Ala Pro Met Gly Asn Asp
            495                 500                 505

ACT ATC CTG AAA CAT GAG CAA ATT GAC CAG CCT CAG GAT GTG AAC TCA       1948
Thr Ile Leu Lys His Glu Gln Ile Asp Gln Pro Gln Asp Val Asn Ser
            510                 515                 520

TTT GCT GGA GGT CAC CCA GGG CTC TTT CAA GAT AGT AAA AAC AGT GAC       1996
Phe Ala Gly Gly His Pro Gly Leu Phe Gln Asp Ser Lys Asn Ser Asp
        525                 530                 535

TTG TAC AGC ATA ATG AAA AAC CTA GGC ATT GAT TTT GAA GAC ATC AGA       2044
Leu Tyr Ser Ile Met Lys Asn Leu Gly Ile Asp Phe Glu Asp Ile Arg
540                 545                 550

CAC ATG CAG AAT GAA AAA TTT TTC AGA AAT GAT TTT TCT GGT GAG GTT       2092
His Met Gln Asn Glu Lys Phe Phe Arg Asn Asp Phe Ser Gly Glu Val
555                 560                 565                 570

GAC TTC AGA GAC ATT GAC TTA ACG GAT GAA ATC CTG ACG TAT GTC CAA       2140
Asp Phe Arg Asp Ile Asp Leu Thr Asp Glu Ile Leu Thr Tyr Val Gln
            575                 580                 585

GAT TCT TTA AGT AAG TCT CCC TTC ATA CCT TCA GAT TAT CAA CAG CAA       2188
Asp Ser Leu Ser Lys Ser Pro Phe Ile Pro Ser Asp Tyr Gln Gln Gln
            590                 595                 600

CAG TCC TTG GCT CTG AAC TCA AGC TGT ATG GTA CAG GAA CAC CTA CAT       2236
Gln Ser Leu Ala Leu Asn Ser Ser Cys Met Val Gln Glu His Leu His
        605                 610                 615

CTA GAA CAG CAA CAG CAA CAT CAC CAA AAG CAA GTA GTA GTG GAG CCA       2284
Leu Glu Gln Gln Gln Gln His His Gln Lys Gln Val Val Val Glu Pro
620                 625                 630

CAG CAA CAG CTG TGT CAG AAG ATG AAG CAC ATG CAA GTT AAT GGC ATG       2332
Gln Gln Gln Leu Cys Gln Lys Met Lys His Met Gln Val Asn Gly Met
635                 640                 645                 650

TTT GAA AAT TGG AAC TCT AAC CAA ATC GTG CCT TTC AAT TGT CCA CAG       2380
Phe Glu Asn Trp Asn Ser Asn Gln Ile Val Pro Phe Asn Cys Pro Gln
            655                 660                 665

CAA GAC CCA CAA CAA TAT AAT GTC TTT ACA GAC TTA CAT GGG ATC AGT       2428
Gln Asp Pro Gln Gln Tyr Asn Val Phe Thr Asp Leu His Gly Ile Ser
            670                 675                 680
```

| | | | | | | | | | | | | | | | | |
|---|---|---|---|---|---|---|---|---|---|---|---|---|---|---|---|---|
| CAA | GAG | TTC | CCC | TAC | AAA | TCT | GAA | ATG | GAT | TCT | ATG | CCT | TAT | ACA | CAG | 2476 |
| Gln | Glu | Phe 685 | Pro | Tyr | Lys | Ser | Glu 690 | Met | Asp | Ser | Met | Pro 695 | Tyr | Thr | Gln | |
| AAC | TTT | ATT | TCC | TGT | AAT | CAG | CCT | GTA | TTA | CCA | CAA | CAT | TCC | AAA | TGT | 2524 |
| Asn | Phe 700 | Ile | Ser | Cys | Asn | Gln 705 | Pro | Val | Leu | Pro | Gln 710 | His | Ser | Lys | Cys | |
| ACA | GAG | CTG | GAC | TAC | CCT | ATG | GGG | AGT | TTT | GAA | CCA | TCC | CCA | TAC | CCC | 2572 |
| Thr 715 | Glu | Leu | Asp | Tyr 720 | Pro | Met | Gly | Ser | Phe 725 | Glu | Pro | Ser | Pro | Tyr 730 | Pro | |
| ACT | ACT | TCT | AGT | TTA | GAA | GAT | TTT | GTC | ACT | TGT | TTA | CAA | CTT | CCT | GAA | 2620 |
| Thr | Thr | Ser | Ser | Leu 735 | Glu | Asp | Phe | Val | Thr 740 | Cys | Leu | Gln | Leu | Pro 745 | Glu | |
| AAC | CAA | AAG | CAT | GGA | TTA | AAT | CCA | CAG | TCA | GCC | ATA | ATA | ACT | CCT | CAG | 2668 |
| Asn | Gln | Lys | His 750 | Gly | Leu | Asn | Pro | Gln 755 | Ser | Ala | Ile | Ile | Thr 760 | Pro | Gln | |
| ACA | TGT | TAT | GCT | GGG | GCC | GTG | TCG | ATG | TAT | CAG | TGC | CAG | CCA | GAA | CCT | 2716 |
| Thr | Cys | Tyr 765 | Ala | Gly | Ala | Val | Ser 770 | Met | Tyr | Gln | Cys | Gln 775 | Pro | Glu | Pro | |
| CAG | CAC | ACC | CAC | GTG | GGT | CAG | ATG | CAG | TAC | AAT | CCA | GTA | CTG | CCA | GGC | 2764 |
| Gln | His | Thr 780 | His | Val | Gly | Gln | Met 785 | Gln | Tyr | Asn | Pro | Val 790 | Leu | Pro | Gly | |
| CAA | CAG | GCA | TTT | TTA | AAC | AAG | TTT | CAG | AAT | GGA | GTT | TTA | AAT | GAA | ACA | 2812 |
| Gln 795 | Gln | Ala | Phe | Leu | Asn 800 | Lys | Phe | Gln | Asn | Gly 805 | Val | Leu | Asn | Glu | Thr 810 | |
| TAT | CCA | GCT | GAA | TTA | AAT | AAC | ATA | AAT | AAC | ACT | CAG | ACT | ACC | ACA | CAT | 2860 |
| Tyr | Pro | Ala | Glu | Leu 815 | Asn | Asn | Ile | Asn | Asn 820 | Thr | Gln | Thr | Thr | Thr 825 | His | |
| CTT | CAG | CCA | CTT | CAT | CAT | CCG | TCA | GAA | GCC | AGA | CCT | TTT | CCT | GAT | TTG | 2908 |
| Leu | Gln | Pro | Leu 830 | His | His | Pro | Ser | Glu 835 | Ala | Arg | Pro | Phe | Pro 840 | Asp | Leu | |
| ACA | TCC | AGT | GGA | TTC | CTG | T AATTCCAAGC CCAATTTGA CCCTGGTTTT | | | | | | | | | | 2957 |
| Thr | Ser | Ser 845 | Gly | Phe | Leu | | | | | | | | | | | |

```
TGGATTAAAT TAGTTTGTGA AGGATTATGG AAAAATAAAA CTGTCACTGT TGGACGTCAG 3017
CAAGTTCACA TGGAGGCATT GATGCATGCT ATTCACAATT ATTCCAAACC AAATTTTAAT 3077
TTTTGCTTTT AGAAAAGGGA GTTAAAAAT  GGTATCAAAA TTACATATAC TACAGTCAAG 3137
ATAGAAGGG  TGCTGCCACG GAGTGGTGAG GTACCGTCTA CATTTCACAT TATTCTGGGC 3197
ACCACAAAAT ATACAAAACT TTATCAGGGA AACTAAGATT CTTTTAAATT AGAAAATATT 3257
CTCTATTTGA ATTATTTCTG TCACAGTAAA AATAAATAC  TTTGAGTTTT GAGCTACTGG 3317
ATTCTTATTA GTTCCCCAAA TACAAAGTTA GAGAACTAAA CTAGTTTTC  CTATCATGTT 3377
AACCTCTGCT TTTATCTCAG ATGTTAAAAT AAATGGTTTG GTGCTTTTA  TAAAAAGATA 3437
ATCTCAGTGC TTTCCTCCTT CACTGTTTCA TCTAAGTGCC TCACATTTTT TTCTACCTAT 3497
AACACTCTAG GATGTATATT TTATATAAAG TATTCTTTTT CTTTTTAAA  TTAATATCTT 3557
TCTGCACACA AATATTATTT GTGTTTCCTA ATCCAACCA  ATTTTCATTA ATTCAGGCAT 3617
ATTTAACTC  CACTGCTTAC CTACTTTCTT CAGGTAAAAG GGCAAATAAT GATCGAAAAA 3677
ATAATTATTT ATTACATAAT TTAGTTGTTT CTAGACTATA AATGTTGCTA TGTGCCTTAT 3737
GTTGAAAAAA TTTAAAAGTA AAATGTCTTT CCAAATTATT TCTTAATTAT TATAAAAATA 3797
TTAAGACAAT AGCACTTAAA TTCCTCAACA GTGTTTTCAG AAGAAATAAA TATACCACTC 3857
TTTACCTTTA TTGATATCTC CATGATGATA GTTGAATGTT GCAATGTGAA AAATCTGCTG 3917
TTAACTGCAA CCTTGTTTAT TAAATTGCAA GAAGCTTTAT TTCTAGCTTT TTAATTAAGC 3977
AAAGCACCCA TTTCAATGTG TATAAATTGT CTTTAAAAAC TGTTTTAGAC CTATAATCCT 4037
```

-continued

```
TGATAATATA TTGTGTTGAC TTTATAAATT TCGCTTCTTA GAACAGTGGA AACTATGTGT  4097
TTTTCTCATA TTTGAGGAGT GTTAAGATTG CAGATAGCAA GGTTTGGTGC AAAGTATTGT  4157
AATGAGTGAA TTGAATGGTG CATTGTATAG ATATAATGAA CAAAATTATT TGTAAGATAT  4217
TTGCAGTTTT TCATTTTAAA AAGTCCATAC CTTATATATG CACTTAATTT GTTGGGGCTT  4277
TACATACTTT ATCAATGTGT CTTTCTAAGA AATCAAGTAA TGAATCCAAC TGCTTAAAGT  4337
TGGTATTAAT AAAAAGACAA CCACATAGTT CGTTACCTT CAAACTTTAG GTTTTTTAA    4397
TGATATACTG ATCTTCATTA CCAATAGGCA AATTAATCAC CCTACCAACT TTACTGTCCT  4457
AACATGGACT TTCAAAAAGA AAAAATGACA CCATCTTTTA TTCTTTTTTT TTTTTTTTT  4517
TTGAGAGAGA GTCTTACTCT GCCGCCCAAA CTGGAGTGCA GTGGCACAAT CTTGGCTCAC  4577
TGCAACCTCT ACCTCCTGGG TTCAAGTGAT TCTCTTGCCT CAGCCTCCCG AGTTGCTGGG  4637
ATTGCGGGCA TGGTGGCGTG AGCCTGTAGT CCTAGCTACT CGGGAGGCTG AGGCAGGAGA  4697
ATAGCCTGAA CCTGGGAATC GGAGGTTGCA GGGCCAAGAT CGCCCCACTG CACTCCAGCC  4757
TGGCAATAGA CCGAGCTCCG TCTCCAAAAA AAAAAATACA ATTTTTATTT CTTTTACTTT  4817
TTTTAGTAAG TTAATGTATA TAAAAATGGC TTCGGACAAA ATATCTCTGA GTTCTGTGTA  4877
TTTTCAGTCA AAACTTTAAA CCTGTAGAAT CAATTTAAGT GTTGAAAAAA ATTTGTCTGA  4937
AACATTTCAT AATTTGTTTC CAGCATGAGG TATCTAAGGA TTTAGACCAG AGGTCTAGAT  4997
TAATACTCTA TTTTTACATT TAAACCTTTT ATTATAAGTC TTACATAAAC CATTTTGTT   5057
ACTCTCTTCC ACATGTTACT GGATAAATTG TTTAGTGGAA AATAGGCTTT TAATCATGA   5117
ATATGATGAC AATCAGTTAT ACAGTTATAA AATTAAAAGT TTGAAAAGCA ATATTGTATA  5177
TTTTTATCTA TATAAAATAA CTAAAATGTA TCTAAGAATA ATAAAATCAC GTTAAACCAA  5237
AAAAAAAAAA AAAAAAAAA AAAA                                         5261
```

( 2 ) INFORMATION FOR SEQ ID NO:4:

( i ) SEQUENCE CHARACTERISTICS:
        ( A ) LENGTH: 848 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Asn Ser Ser Ser Ala Asn Ile Thr Tyr Ala Ser Arg Lys Arg Arg
 1               5                  10                  15

Lys Pro Val Gln Lys Thr Val Lys Pro Ile Pro Ala Glu Gly Ile Lys
            20                  25                  30

Ser Asn Pro Ser Lys Arg His Arg Asp Arg Leu Asn Thr Glu Leu Asp
        35                  40                  45

Arg Leu Ala Ser Leu Leu Pro Phe Pro Gln Asp Val Ile Asn Lys Leu
    50                  55                  60

Asp Lys Leu Ser Val Leu Arg Leu Ser Val Ser Tyr Leu Arg Ala Lys
65                  70                  75                  80

Ser Phe Phe Asp Val Ala Leu Lys Ser Ser Pro Thr Glu Arg Asn Gly
                85                  90                  95

Gly Gln Asp Asn Cys Arg Ala Ala Asn Phe Arg Glu Gly Leu Asn Leu
            100                 105                 110

Gln Glu Gly Glu Phe Leu Leu Gln Ala Leu Asn Gly Phe Val Leu Val
        115                 120                 125

Val Thr Thr Asp Ala Leu Val Phe Tyr Ala Ser Ser Thr Ile Gln Asp
    130                 135                 140
```

```
Tyr  Leu  Gly  Phe  Gln  Gln  Ser  Asp  Val  Ile  His  Gln  Ser  Val  Tyr  Glu
145                 150                      155                     160

Leu  Ile  His  Thr  Glu  Asp  Arg  Ala  Glu  Phe  Gln  Arg  Gln  Leu  His  Trp
                    165                      170                     175

Ala  Leu  Asn  Pro  Ser  Gln  Cys  Thr  Glu  Ser  Gly  Gln  Gly  Ile  Glu  Glu
                    180                      185                     190

Ala  Thr  Gly  Leu  Pro  Gln  Thr  Val  Val  Cys  Tyr  Asn  Pro  Asp  Gln  Ile
               195                 200                      205

Pro  Pro  Glu  Asn  Ser  Pro  Leu  Met  Glu  Arg  Cys  Phe  Ile  Cys  Arg  Leu
          210                 215                      220

Arg  Cys  Leu  Leu  Asp  Asn  Ser  Ser  Gly  Phe  Leu  Ala  Met  Asn  Phe  Gln
225                 230                      235                     240

Gly  Lys  Leu  Lys  Tyr  Leu  His  Gly  Gln  Lys  Lys  Gly  Lys  Asp  Gly
                    245                      250                     255

Ser  Ile  Leu  Pro  Pro  Gln  Leu  Ala  Leu  Phe  Ala  Ile  Ala  Thr  Pro  Leu
               260                 265                      270

Gln  Pro  Pro  Ser  Ile  Leu  Glu  Ile  Arg  Thr  Lys  Asn  Phe  Ile  Phe  Arg
          275                 280                      285

Thr  Lys  His  Lys  Leu  Asp  Phe  Thr  Pro  Ile  Gly  Cys  Asp  Ala  Lys  Gly
          290                 295                      300

Arg  Ile  Val  Leu  Gly  Tyr  Thr  Glu  Ala  Glu  Leu  Cys  Thr  Arg  Gly  Ser
305                 310                      315                     320

Gly  Tyr  Gln  Phe  Ile  His  Ala  Ala  Asp  Met  Leu  Tyr  Cys  Ala  Glu  Ser
                    325                      330                     335

His  Ile  Arg  Met  Ile  Lys  Thr  Gly  Glu  Ser  Gly  Met  Ile  Val  Phe  Arg
               340                 345                      350

Leu  Leu  Thr  Lys  Asn  Asn  Arg  Trp  Thr  Trp  Val  Gln  Ser  Asn  Ala  Arg
          355                 360                      365

Leu  Leu  Tyr  Lys  Asn  Gly  Arg  Pro  Asp  Tyr  Ile  Ile  Val  Thr  Gln  Arg
          370                 375                      380

Pro  Leu  Thr  Asp  Glu  Glu  Gly  Thr  Glu  His  Leu  Arg  Lys  Arg  Asn  Thr
385                 390                      395                     400

Lys  Leu  Pro  Phe  Met  Phe  Thr  Thr  Gly  Glu  Ala  Val  Leu  Tyr  Glu  Ala
               405                 410                      415

Thr  Asn  Pro  Phe  Pro  Ala  Ile  Met  Asp  Pro  Leu  Pro  Leu  Arg  Thr  Lys
               420                 425                      430

Asn  Gly  Thr  Ser  Gly  Lys  Asp  Ser  Ala  Thr  Thr  Ser  Thr  Leu  Ser  Lys
          435                 440                      445

Asp  Ser  Leu  Asn  Pro  Ser  Ser  Leu  Leu  Ala  Ala  Met  Met  Gln  Gln  Asp
     450                 455                      460

Glu  Ser  Ile  Tyr  Leu  Tyr  Pro  Ala  Ser  Ser  Thr  Ser  Ser  Thr  Ala  Pro
465                 470                      475                     480

Phe  Glu  Asn  Asn  Phe  Phe  Asn  Glu  Ser  Met  Asn  Glu  Cys  Arg  Asn  Trp
                    485                      490                     495

Gln  Asp  Asn  Thr  Ala  Pro  Met  Gly  Asn  Asp  Thr  Ile  Leu  Lys  His  Glu
               500                 505                      510

Gln  Ile  Asp  Gln  Pro  Gln  Asp  Val  Asn  Ser  Phe  Ala  Gly  Gly  His  Pro
          515                 520                      525

Gly  Leu  Phe  Gln  Asp  Ser  Lys  Asn  Ser  Asp  Leu  Tyr  Ser  Ile  Met  Lys
          530                 535                      540

Asn  Leu  Gly  Ile  Asp  Phe  Glu  Asp  Ile  Arg  His  Met  Gln  Asn  Glu  Lys
545                 550                      555                     560

Phe  Phe  Arg  Asn  Asp  Phe  Ser  Gly  Glu  Val  Asp  Phe  Arg  Asp  Ile  Asp
```

|     |     |     |     |     | 565 |     |     |     |     | 570 |     |     |     |     | 575 |     |
| --- | --- | --- | --- | --- | --- | --- | --- | --- | --- | --- | --- | --- | --- | --- | --- | --- |
| Leu | Thr | Asp | Glu | Ile | Leu | Thr | Tyr | Val | Gln | Asp | Ser | Leu | Ser | Lys | Ser |
|     |     |     | 580 |     |     |     |     | 585 |     |     |     |     | 590 |     |     |
| Pro | Phe | Ile | Pro | Ser | Asp | Tyr | Gln | Gln | Gln | Gln | Ser | Leu | Ala | Leu | Asn |
|     |     | 595 |     |     |     |     | 600 |     |     |     |     | 605 |     |     |     |
| Ser | Ser | Cys | Met | Val | Gln | Glu | His | Leu | His | Leu | Glu | Gln | Gln | Gln | Gln |
|     | 610 |     |     |     |     | 615 |     |     |     |     | 620 |     |     |     |     |
| His | His | Gln | Lys | Gln | Val | Val | Glu | Pro | Gln | Gln | Gln | Leu | Cys | Gln |
| 625 |     |     |     |     | 630 |     |     |     |     | 635 |     |     |     | 640 |
| Lys | Met | Lys | His | Met | Gln | Val | Asn | Gly | Met | Phe | Glu | Asn | Trp | Asn | Ser |
|     |     |     |     | 645 |     |     |     |     | 650 |     |     |     |     | 655 |     |
| Asn | Gln | Ile | Val | Pro | Phe | Asn | Cys | Pro | Gln | Gln | Asp | Pro | Gln | Gln | Tyr |
|     |     |     | 660 |     |     |     |     | 665 |     |     |     |     | 670 |     |     |
| Asn | Val | Phe | Thr | Asp | Leu | His | Gly | Ile | Ser | Gln | Glu | Phe | Pro | Tyr | Lys |
|     |     | 675 |     |     |     |     | 680 |     |     |     |     | 685 |     |     |     |
| Ser | Glu | Met | Asp | Ser | Met | Pro | Tyr | Thr | Gln | Asn | Phe | Ile | Ser | Cys | Asn |
|     | 690 |     |     |     |     | 695 |     |     |     |     | 700 |     |     |     |     |
| Gln | Pro | Val | Leu | Pro | Gln | His | Ser | Lys | Cys | Thr | Glu | Leu | Asp | Tyr | Pro |
| 705 |     |     |     |     | 710 |     |     |     |     | 715 |     |     |     |     | 720 |
| Met | Gly | Ser | Phe | Glu | Pro | Ser | Pro | Tyr | Pro | Thr | Thr | Ser | Ser | Leu | Glu |
|     |     |     |     | 725 |     |     |     |     | 730 |     |     |     |     | 735 |     |
| Asp | Phe | Val | Thr | Cys | Leu | Gln | Leu | Pro | Glu | Asn | Gln | Lys | His | Gly | Leu |
|     |     |     | 740 |     |     |     |     | 745 |     |     |     |     | 750 |     |     |
| Asn | Pro | Gln | Ser | Ala | Ile | Ile | Thr | Pro | Gln | Thr | Cys | Tyr | Ala | Gly | Ala |
|     |     | 755 |     |     |     |     | 760 |     |     |     |     | 765 |     |     |     |
| Val | Ser | Met | Tyr | Gln | Cys | Gln | Pro | Glu | Pro | Gln | His | Thr | His | Val | Gly |
|     | 770 |     |     |     |     | 775 |     |     |     |     | 780 |     |     |     |     |
| Gln | Met | Gln | Tyr | Asn | Pro | Val | Leu | Pro | Gly | Gln | Gln | Ala | Phe | Leu | Asn |
| 785 |     |     |     |     | 790 |     |     |     |     | 795 |     |     |     |     | 800 |
| Lys | Phe | Gln | Asn | Gly | Val | Leu | Asn | Glu | Thr | Tyr | Pro | Ala | Glu | Leu | Asn |
|     |     |     |     | 805 |     |     |     |     | 810 |     |     |     |     | 815 |     |
| Asn | Ile | Asn | Asn | Thr | Gln | Thr | Thr | Thr | His | Leu | Gln | Pro | Leu | His | His |
|     |     |     | 820 |     |     |     |     | 825 |     |     |     |     | 830 |     |     |
| Pro | Ser | Glu | Ala | Arg | Pro | Phe | Pro | Asp | Leu | Thr | Ser | Ser | Gly | Phe | Leu |
|     |     | 835 |     |     |     |     | 840 |     |     |     |     | 845 |     |     |     |

(2) INFORMATION FOR SEQ ID NO:5:

(i) SEQUENCE CHARACTERISTICS:
        (A) LENGTH: 52 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: modified_base
        (B) LOCATION: 3
        (D) OTHER INFORMATION: /mod_base=i (ix) FEATURE:
        (A) NAME/KEY: modified_base
        (B) LOCATION: 6
        (D) OTHER INFORMATION: /mod_base=i (ix) FEATURE:
        (A) NAME/KEY: modified_base
        (B) LOCATION: 13
        (D) OTHER INFORMATION: /mod_base=i (ix) FEATURE:

( A ) NAME/KEY: modified_base
                    ( B ) LOCATION: 16
                    ( D ) OTHER INFORMATION: /mod_base=i ( i x ) FEATURE:
                    ( A ) NAME/KEY: modified_base
                    ( B ) LOCATION: 19
                    ( D ) OTHER INFORMATION: /mod_base=i ( i x ) FEATURE:
                    ( A ) NAME/KEY: modified_base
                    ( B ) LOCATION: 22
                    ( D ) OTHER INFORMATION: /mod_base=i ( i x ) FEATURE:
                    ( A ) NAME/KEY: modified_base
                    ( B ) LOCATION: 29
                    ( D ) OTHER INFORMATION: /mod_base=i ( i x ) FEATURE:
                    ( A ) NAME/KEY: modified_base
                    ( B ) LOCATION: 32
                    ( D ) OTHER INFORMATION: /mod_base=i ( i x ) FEATURE:
                    ( A ) NAME/KEY: modified_base
                    ( B ) LOCATION: 43
                    ( D ) OTHER INFORMATION: /mod_base=i ( i x ) FEATURE:
                    ( A ) NAME/KEY: modified_base
                    ( B ) LOCATION: 46
                    ( D ) OTHER INFORMATION: /mod_base=i ( x i ) SEQUENCE DESCRIPTION: SEQ ID NO:5:

TTNATCCTC TCNGCNGGNA TNGGTCTTNA CNGTTCTTTC TGNACNGGTC TT    52

( 2 ) INFORMATION FOR SEQ ID NO:6:

( i ) SEQUENCE CHARACTERISTICS:
                    ( A ) LENGTH: 20 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( i x ) FEATURE:
                    ( A ) NAME/KEY: modified_base
                    ( B ) LOCATION: 7
                    ( D ) OTHER INFORMATION: /mod_base=OTHER
                            / note= "Can be either adenine, thymine, guanosine,
                            or cytosine."

( i x ) FEATURE:
                    ( A ) NAME/KEY: modified_base
                    ( B ) LOCATION: 10
                    ( D ) OTHER INFORMATION: /mod_base=OTHER
                            / note= "Can be either adenine, thymine, guanosine,
                            or cytosine."

( x i ) SEQUENCE DESCRIPTION: SEQ ID NO:6:

AAAGCCNGTN CAAGAAAGAC    20

( 2 ) INFORMATION FOR SEQ ID NO:7:

( i ) SEQUENCE CHARACTERISTICS:
                    ( A ) LENGTH: 25 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:7:

```
GGATTTGACT  TAATTCCTTC  AGGGG                                             25
```

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

```
CCATCGATCT  CGAGAGATTG  CAGATAGCAA  GGTTTGGTGC                             40
```

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

```
CCATCGATCT  CGAGTGTAAT  GAGTGAATTG  AATGGTGC                               38
```

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

```
GAAGATCTTC  CAGTGGTCCC  AGCCTACACC                                         30
```

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:11:

```
GAAGATCTTC  ATGTGAACTT  GCTGACGTCC                                         30
```

( 2 ) INFORMATION FOR SEQ ID NO:12:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

```
GCTCTAGATG  ATCACCATGG  TGCAGAAGAC  CGTGAAGCCC  ATCCCGCTG  AAGGAATTAA      60
GTC                                                                       63
```

( 2 ) INFORMATION FOR SEQ ID NO:13:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

```
GCACTAGTTG ATCACCATGG CCAGCCGCAA GCGGCGCAAG CCGGTGCAGA AGACCGTGAA    60

GCC                                                                 63
```

( 2 ) INFORMATION FOR SEQ ID NO:14:

( i ) SEQUENCE CHARACTERISTICS:
        ( A ) LENGTH: 65 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

```
GCACTAGTTG ATCACCATGA GCAGCGGCGC CAACATCACC TATGCCAGCC GCAAGCGCCG    60

CAAGC                                                               65
```

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

```
GCAGAGTCTG GGTTTAGAGC    20
```

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

```
TCGAGTAGAT CACGCAATGG GCCCAGC    27
```

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

```
TCGAGCTGGG CCCATTGCGT GATCTAC    27
```

( 2 ) INFORMATION FOR SEQ ID NO:18:

( i ) SEQUENCE CHARACTERISTICS:
  ( A ) LENGTH: 28 base pairs
  ( B ) TYPE: nucleic acid
  ( C ) STRANDEDNESS: unknown
  ( D ) TOPOLOGY: unknown ( i i ) MOLECULE TYPE: DNA (genomic)

( x i ) SEQUENCE DESCRIPTION: SEQ ID NO:18:

GCGTCGACTG GGCACCATGA ACAGCAGC 28

( 2 ) INFORMATION FOR SEQ ID NO:19:

( i ) SEQUENCE CHARACTERISTICS:
    ( A ) LENGTH: 40 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:19:

CCCAAGCTTA CGCGTGGTTC TCTGGAGGAA GCTGGTCTGG 40

( 2 ) INFORMATION FOR SEQ ID NO:20:

( i ) SEQUENCE CHARACTERISTICS:
    ( A ) LENGTH: 36 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:20:

CCCAAGCTTA CGCGTGGAAG TCTAGCTTGT GTTTGG 36

( 2 ) INFORMATION FOR SEQ ID NO:21:

( i ) SEQUENCE CHARACTERISTICS:
    ( A ) LENGTH: 36 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:21:

CCCAAGCTTA CGCGTGAAGC CGGAAAACTG TCATGC 36

( 2 ) INFORMATION FOR SEQ ID NO:22:

( i ) SEQUENCE CHARACTERISTICS:
    ( A ) LENGTH: 49 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:22:

CCCAAGCTTA CGCGTGCAGT GGTCTCTGAG TGGCGATGAT GTAATCTGG 49

( 2 ) INFORMATION FOR SEQ ID NO:23:

( i ) SEQUENCE CHARACTERISTICS:
    ( A ) LENGTH: 37 base pairs
    ( B ) TYPE: nucleic acid
    ( C ) STRANDEDNESS: unknown (D) TOPOLOGY: unknown (i i) MOLECULE TYPE: DNA (genomic)

(x i) SEQUENCE DESCRIPTION: SEQ ID NO:23:

CCCAAGCTTA CGCGTGGTCT TTGAAGTCAA CCTCACC 37

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:24:

GAATTGTAAT ACGACTCACT ATAGGG 26

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:25:

CGCTCGAGAA CTAGTGGATC 20

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:26:

AGCTGCTTAA TTAATTAAGC A 21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:27:

AGCTTGCTTA ATTAATTAAG C 21

(2) INFORMATION FOR SEQ ID NO:28:

(i) SEQUENCE CHARACTERISTICS:
        (A) LENGTH: 34 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:28:

GCGTCGACTG ATGAGCAGCG GCGCCAACAT CACC    34

( 2 ) INFORMATION FOR SEQ ID NO:29:

( i ) SEQUENCE CHARACTERISTICS:
    ( A ) LENGTH: 20 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:29:

CATTACTTAT CTAGAGCTCG    20

( 2 ) INFORMATION FOR SEQ ID NO:30:

( i ) SEQUENCE CHARACTERISTICS:
    ( A ) LENGTH: 19 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:30:

GATTTAGGTG ACACTATAG    19

( 2 ) INFORMATION FOR SEQ ID NO:31:

( i ) SEQUENCE CHARACTERISTICS:
    ( A ) LENGTH: 49 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:31:

GATAAGAATG CGGCCGCACG GATCCAGCAG CAACAGCAAA CAGAATTGG    49

( 2 ) INFORMATION FOR SEQ ID NO:32:

( i ) SEQUENCE CHARACTERISTICS:
    ( A ) LENGTH: 38 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:32:

ATAAGAATGC GGCCGCAGCC CCCCGACCG ATGTCAGC    38

( 2 ) INFORMATION FOR SEQ ID NO:33:

( i ) SEQUENCE CHARACTERISTICS:
    ( A ) LENGTH: 37 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:33:

ATAGTTTAGC GGCCGCCCCA CCGTACTCGT CAATTCC    37

( 2 ) INFORMATION FOR SEQ ID NO:34:

( i ) SEQUENCE CHARACTERISTICS:
    ( A ) LENGTH: 37 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:34:

GCCGTCGACG CGGCCGCGAA GTCTAGCTTG TGTTTGG 37

( 2 ) INFORMATION FOR SEQ ID NO:35:

( i ) SEQUENCE CHARACTERISTICS:
    ( A ) LENGTH: 36 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:35:

ATAAGAATGC GGCCGCACCC TCAATGTTGT GTCGGG 36

( 2 ) INFORMATION FOR SEQ ID NO:36:

( i ) SEQUENCE CHARACTERISTICS:
    ( A ) LENGTH: 40 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO:36:

CGGGATCCTC GCGGCCGCAG AGAATTTCAG GAATAGTGGC 40

BIOLOGICAL ASSAY FOR DETECTING AGONISTS TO THE AH RECEPTOR

This application is a continuation-in-part application of U.S. Ser. No. 08/045,806, filed Apr. 8, 1993, now U.S. Pat. No. 5,378,822.

This invention was made with Government support under Grant Number: ES-05703 awarded by the National Institute of Environmental Health Sciences, and NIH grant E505703. The Government has certain rights in the invention.

FIELD OF INVENTION

This invention relates to cDNA molecules encoding the murine and human Ah-receptors ($Ah^{b-1}$ allele) that have been isolated and characterized. More specifically, the cDNAs of this invention can be used to make Ah-receptors which can be used inserted into cells for use in bioassays to detect environmental pollutants. Additionally, these cDNAs can be used in the generation of recombinant organisms that serve as biomonitors for environmental pollutants and as probes for detecting human and wildlife populations that have high susceptibility to environmental pollutants and polycyclic aromatic hydrocarbons.

BACKGROUND OF THE INVENTION

The Ah-receptor is a soluble protein which mediates an individuals response to a variety of drugs, carcinogens and toxic agents. Chemicals which interact with the Ah-receptor, include a variety of environmental contaminants (dioxins, PCBs, PBBs, benzo(a)pyrene and a variety of natural products (flavones, carbazoles etc). One of the most potent agonists of the Ah-receptor is 2,3,7,8-tetrachlorodibenzo-p-dioxin (TCDD or "dioxin"). TCDD is the prototype for a large family of highly toxic carcinogenic and teratogenic environmental contaminants. Poland A., Knutson, J. C., *Ann. Rev. Pharmacol. Toxicol.* 22:517–554 (1982). Members of this family include a number of halogenated dibenzo-p-dioxin, dibenzofuran, and biphenyl isomers which induce a variety of receptor-mediated toxic responses, including a severe wasting syndrome, epidermal hyperplasia and metaplasia, tumor promotion and thymic involution.

The Ah receptor is believed to reside primarily in the cytosol. While in the cytosol, the Ah receptor is associated with a dimer of the 90 kDa heat shock protein (hsp 90). It is believed that hsp 90 holds the Ah receptor in a conformation capable of binding ligand, but unable to bind to DNA. Upon binding of a ligand, the Ah receptor undergoes a temperature dependent activation, dissociates from the hsp 90, translocates from the cytosol to the nucleus, displays an increased affinity for specific DNA enhancer elements, known as the dioxin responsive elements (DRE) found in the nucleus. Enhancer elements increase transcriptional efficiency, often independent of their orientation and distance with respect to the promoter.

Once translocated to the nucleus, the Ah receptor dimerizes with the Ah receptor nuclear translocator (ARNT) protein. The Ah receptor-ARNT complex exhibits enhanced affinity for the DREs. The binding of the Ah receptor-ARNT complex to the DRE initiates transcription of the mRNA for the CYP1A1 gene. See Durrin, L. K., Jones, P., B. C., Fisher, J. M. Galeazzi, D. R., and Whitlock, J. P., Jr., *J. of Cell. Biochem.* 35:153–160 (1987); citing Adesnick, M., Atchison, M., *Crit. Rev. Biochem.* 19:247–305 (1985) and Lu Ayh, Wet SB., *Pharmacol. Rev.* 31:277–295 (1979). The CYP1A1 gene encodes an isozyme of the cytochrome P450 enzyme family. Cytochrome P450 enzymes catalyze the oxygenation of many endogenous and exogenous lipophilic substrates and are involved in a variety of metabolic activities.

The photoaffinity ligand, [$^{125}$I]-2-azido-3-iodo-7,8-dibromodibenzo-p-dioxin, covalently labels the Ah-receptor from a number of species, tissues and cell types. Poland, A., Glover, E., Ebetino, F. H. & Kende, A. S., *J. Biol. Chem.* 261:6352–6365 (1986). These photoaffinity labeling studies demonstrated that the Ah-receptor exhibits significant polymorphism, both between species and within different strains of the same species. For example, four different allelic forms of the Ah-receptor have been identified in inbred strains of mice: $Ah^{b-1}$ allele (C57 strains)=95 kD, $Ah^{b-2}$ allele (e.g., C3H strain)=104 kD, $Ah^{b-3}$ allele (Mus spretus)=105 kD, and $Ah^d$ allele (e.g., DBA strain)=104 kD. The $Ah^d$ allele encodes a receptor with a 10–100-fold lower affinity for agonist than the $Ah^{b-1}$ or $Ah^{b-2}$ alleles. Poland, A. & Glover, E., *Mol. Pharm.* 11:389–398 (1975); Okey, A. B., Vella, L. M. & Harper, P. A., *Mol. Pharm.* 35:823–830 (1989); Poland, A., Palen, D., Glover, E., *Mol. Pharm.* 46:915–921 (1994).

The purification of the Ah-receptor from C57BL/6J mouse liver has been described. Bradfield, C. A., Glover, E. & Poland, A., *Mol. Pharm.* 39:13–9 (1991). To confirm the identity of this purified protein, its N-terminal amino acids has been sequenced and the corresponding peptide synthesized. Poland, A., Glover, E. & Bradfield, C. A., *Mol. Pharmacol.* 39:20–6 (1991).

SUMMARY OF THE INVENTION

The present invention involves the isolation and characterization of cDNA sequences which encode the murine rat and human Ah receptors. These Ah receptor cDNAs have the sequences set out in Sequence ID. Nos. 1 and 3 and can be used to generate large quantities of the Ah receptor for use in assays and for insertion in yeast and animal cell systems.

The present invention also involves genetically engineered viable cells. According to this invention, two types of genetically engineered cells can be formulated. The first type of cells that can be transformed are yeast cells, such as *Saccharomyces cerevisiae* and *Saccharomyces pombe*. The yeast may be genetically transformed with plasmids expressing the Ah receptor, the Ah receptor nuclear translocator, and a reporter gene driven by a the dioxin responsive element. Additionally, the yeast may be transformed with a plasmid expressing a chimeric Ah receptor and a plasmid expressing a reporter gene driven by a suitable operator. The chimeric Ah receptor is constructed by replacing the binding and dimerization region of the Ah receptor with an analogous domain from a protein capable of binding DNA sequences. The operator sequence contains the binding sites from the binding domain of the protein used to replace the binding and dimerization domain of the Ah receptor.

The second type of cells that can be transformed are mammalian cells, such as COS-1 cells. As with the yeast cells, the mammalian cells can be transformed with a plasmid expressing a chimeric Ah receptor and a plasmid expressing a reporter gene driven by a suitable operator.

The genetically engineered cells of this invention can be used in an assay to detect agonists to the Ah receptor. The assay can be used to detect agonists in environmental samples such as air, water and soil. Such an assay can be conducted on agar plates or in a liquid media. Such an assay would involve preparing a culture of the genetically engineered viable cells, incorporating the sample to be tested into the culture, growing the culture for several hours, determining Ah receptor activation by defecting reporter gene expression and monitoring agonists based on Ah receptor activation.

BRIEF DESCRIPTION OF THE DRAWINGS

FIG. 6B shows the amino acid sequence of the human Ah-receptor (Hu) and comparison with the murine Ah-receptor.

FIG. 14A shows the structure of ligands used in the dose-response assay and the key to symbols. The square refers to βNF, the triangle, αNF, and the diamond, dexamethasone. FIG. 14B shows the dose-response curves for AHR/ARNT/DRE-2 system. Cultures containing strain A303 tranformed with plasmids pCWhuAHR, pY2ARNT, and pDRE23-Z were exposed to agonist for 16–18 hours and β-galactosidase assays performed to measure reporter activity; β-Galactosidase units were converted to precent of the maximal activity of βNF and plotted against concentration. FIG. 14C shows the dose-response curve for the chimeric AHR-LexA signaling system. Strain GRS4 transformed with plasmids pEGAYRNΔ166 and pSH18–34 were grown in 2% galactose selection media containing agonists for 16–18 hours. β-Galactosidase activity was measured to determine reporter gene expression. β-Galactosidase units for all ligands were compared to the maximum response of βNF and plotted against agonist concentrations.

DETAILED DESCRIPTION OF THE INVENTION

For purposes of clarity of disclosure, and not by way of limitation, the detailed disclosure is divided into the following subsections:

(i) Cloning the Murine Ah-receptor;
 (a) Cloning the Murine Ah-Receptor
 (b) Cloning the Human Ah-Receptor
(ii) The Genes and Proteins of this invention;
(iii) Expression of the Ah receptor;
(iv) The Utility of the invention; and
(v) Genetically Engineered Cell Systems and Assays for Detecting Agonists to the Ah receptor.

(i) Cloning the Ah-receptor (a) Cloning the Murine Ah-Receptor

The Ah receptor gene is defined herein as the nucleic acid sequences encoding the Ah receptor proteins and may be identified according to the invention by cloning cDNA transcripts of Ah protein and identifying clones containing full length Ah receptor protein-encoding sequences or using oligonucleotide probes designated as Sequence ID. NOS. 5, 6, & 7.

Three oligonucleotide probes are used to obtain cDNA from a purified Ah receptor. These oligonucleotides were obtained from the N-terminal of a purified Ah receptor. The three oligonucleotides probes are referred to as OL-18, OL-2, and OL-27. OL-18 is designed from the amino acid sequence lysine 16-lysine 31 and was represented by the DNA sequence:

5'TTNATNCCT/CTCNGCNGGNATNGGT/CTTNACNGTT/CTTT/CTGNACNGGTCTT 3' (SEQUENCE ID. NO. 5)

wherein A=Adenine, T=Thymine, C=Cytosine, G=Guanine, N=Inosine. OL-2 was designed from amino acid sequence lysine-16-threonine and is represented by the DNA sequence:

5' AAA/GCCNGTNCAA/GAAAGAC 3' (SEQUENCE ID. NO. 6)

wherein A=Adenine, T=Thymine, C=Cytosine, G=Guanine, N=A, C, G, and T. OL-27 was derived from the open reading frame of a genomic clone. OL-27 corresponds to the nucleotides encoding proline 26–34 and is represented by the DNA sequence:

5' GGATTTGACTTAATTCCTTCAGGGG 3' (SEQUENCE ID. NO. 7)

wherein A=Adenine, T=Thymine, C=Cytosine, G=Guanine.

The Ah-receptor is purified from C57BL/6J mouse liver that is covalently labeled with [$^{125}$I]-2-azido-3-iodo-7,8-dibromodibenzo-p-dioxin. While mouse liver is probably the best source for Ah-receptor, other rodent tissues, such as murine thymus, kidney, lung can be utilized. To obtain the cDNA molecule, the OL-18 oligonucleotide, designed from the N-terminal amino acid sequence, is used as a probe to screen a mouse genomic DNA library. After screening 4×10$^5$ recombinant plaques, the OL-18 oligonucleotide is used as a hybridization probe to isolate a clone. This clone is further analyzed using the second oligonucleotide, OL-2.

Figure 2:
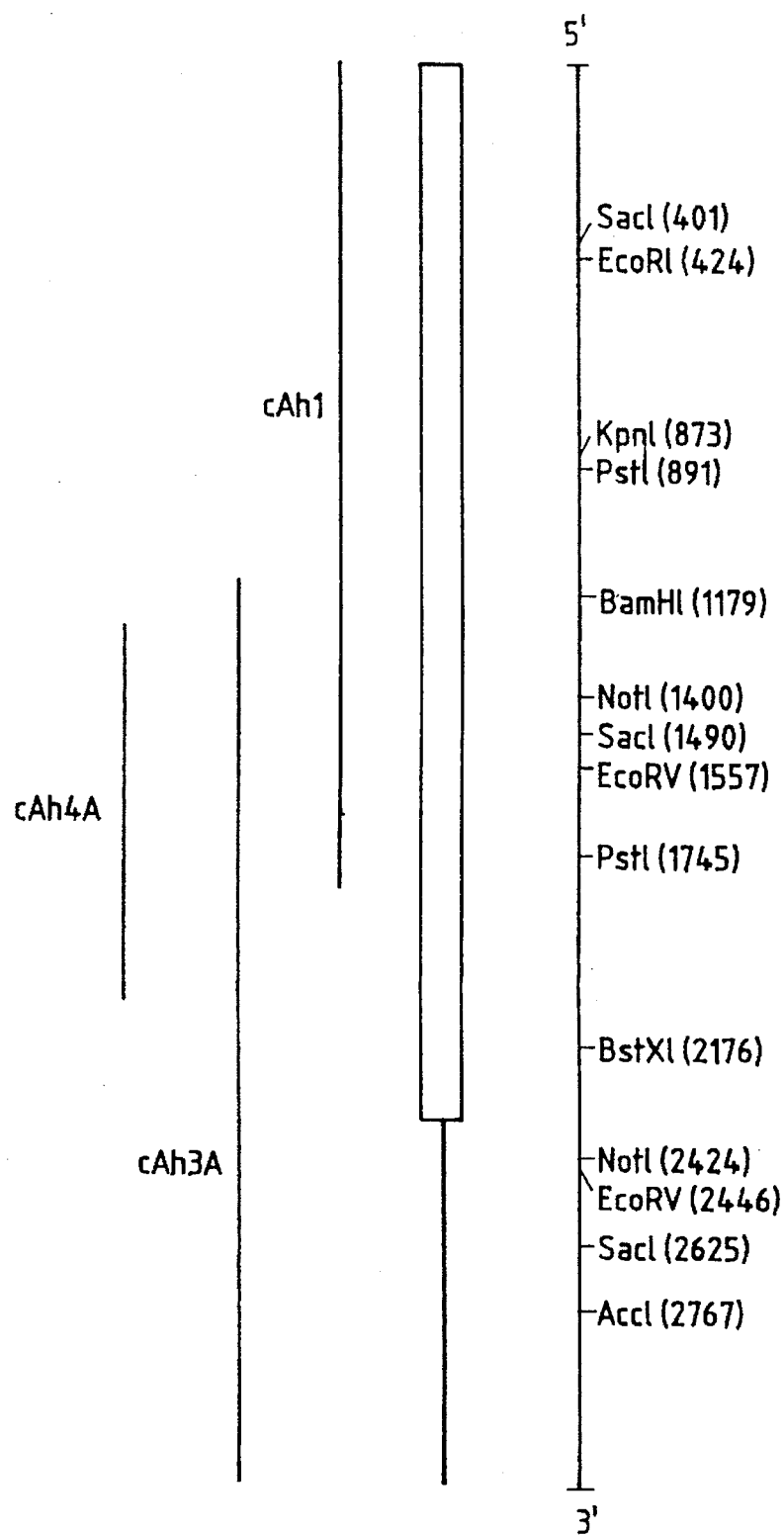
FIG. 2 shows a restriction map and location of cDNA clones.

The third oligonucleotide, OL-27, is designed from the downstream open reading frame (ORF) of the above genomic clone. OL-27 is used to screen 6×10$^5$ recombinants under high stringency conditions (65° C. 2×SSC) to isolate a single clone, cAh1. See FIG. 2. The cAh1 clone is used as a probe to rescreen the mouse cDNA library. After rescreening an additional 1×10$^6$ recombinants, two overlapping clones, cAh3A and cAh4a are obtained. The cAh3A overlaps with the 3' end of cAh1. The cAh4A overlaps with the 3' end of cAh1 and the 5' end of cAh3A See FIG. 2.

The genomic sequence 5' to the upstream open reading frame was analyzed and a putative upstream initiating methionine within a consensus sequence for translational initiation identified. Kozak, M., *Nuc. Acids Res.* 15:8125–8132 (1987). Polymerase chain reaction (PCR) was used to amplify this sequence out of Poly(A)RNA. The amplified fragment is subcloned into pBSK (clone cAhPCR1, FIG. 2) and sequenced to confirm its presence in the full length cDNA (mRNA).

(b) Cloning the Human Ah-receptor

The Ah-receptor's structure and the pattern of toxic responses that it induces vary significantly both within and across species. Poland, A., Knustson, J. C., *Ann. Rev. Pharmacol. Toxicol.* 22:517–554 (1982); Poland, A., Glover, E., *Biochem. Biophys. Res. Comm.* 146:1439–1449 (1987); Safe, S., *Critical Reviews in Toxicology* 21:51–88 (1990). This variability among animal models and target populations makes it difficult to confidently assess the risks associated with exposure to TCDD. "Research News", *Science* 252:911 (1991); "News and Comment", *Science* 251:624–626 (1991); Hanson, D. J., *Chemical and Engineering News*, 7–14 (1991). In order to perform functional comparisons of the Ah-receptor from two important animal targets, the murine cDNA was used as a probe to isolate the corresponding human clone. See Sequence ID. NO. 1.

Figure 6A:
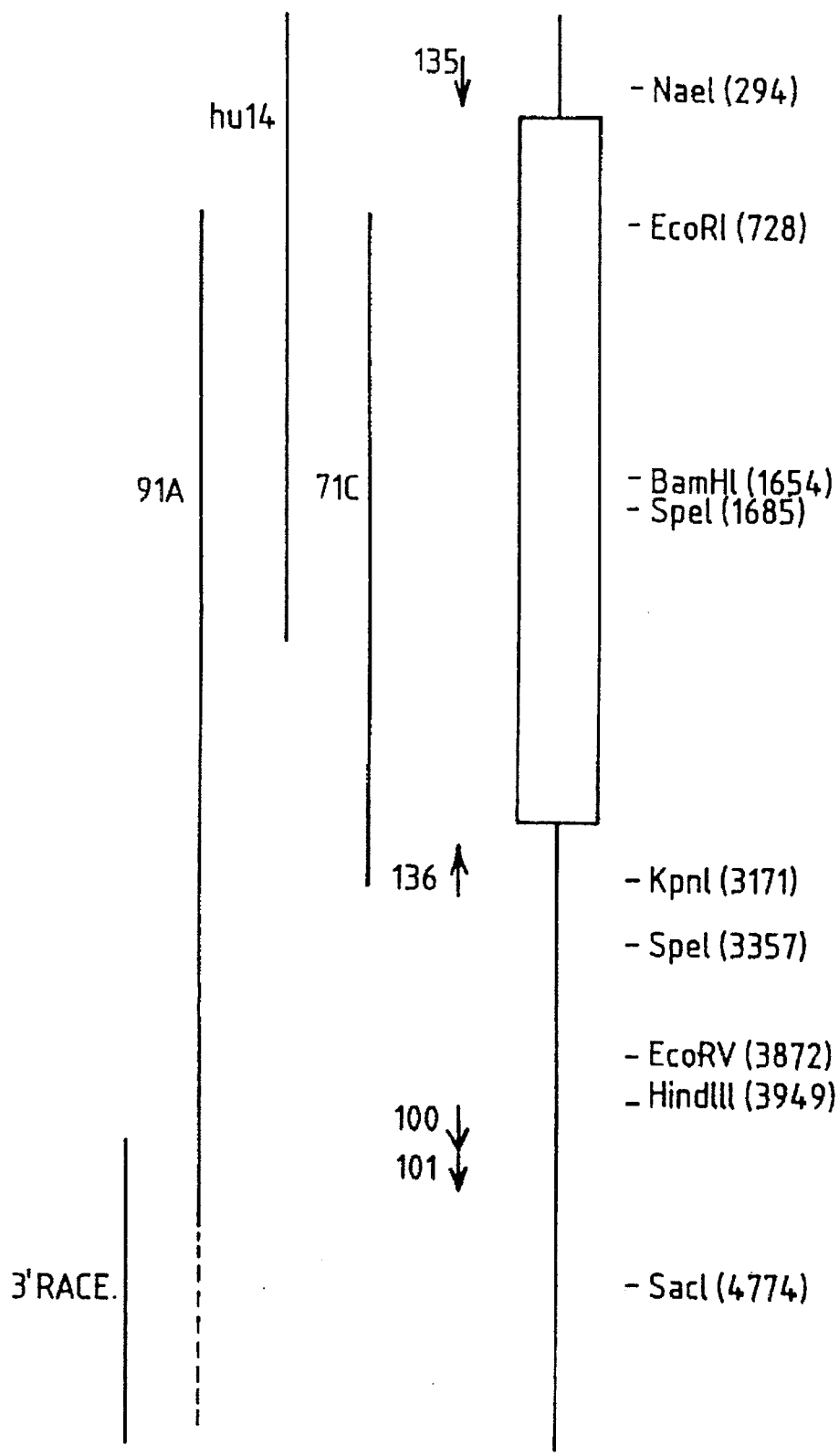
FIG. 6A shows a partial restriction map and location of human Ah-receptor cDNA clones.

The 1.4 bp EcoRI fragment from the murine Ah-receptor cDNA clone, cAh1 (See FIG. 2), was used as a probe to screen a commercially made human cDNA library constructed from oligo dT primed mRNA of the hepatoma cell line, HepG2 (Lambda Zap Vector, STRATAGENE). 5×10$^5$ Recombinants were screened (50% formamide, 37° C.) yielding two overlapping cDNA clones, 91A and 71C. See FIG. 6A. Clone 91A contained a 4.47 kb insert which began with a continuous open reading frame (ORF) coding for 732 amino acids before reaching an in-frame termination codon (TAA). Clone 71C contained a 2.45 kb insert which began at the same site as 91A and extended 264 nucleotides beyond the termination codon. The ORF of the human Ah-receptor clones begins at amino acid 15 of the murine Ah-receptor. An additional 4×10$^5$ recombinants were screened (50% formamide, 42° C.) using the 0.92 kb BamHi fragment of 91A as a probe. See FIG. 6A. One positive clone, hu14, was isolated which contained a 2.28 kb insert. The 3' end of this clone overlapped 1.56 kb with the 5' ends of 91A and 71C. Sequence analysis of hu14 extended the ORF described for 91A and 71C an additional 116 amino acids at the N-terminus to a proposed initiation methionine. This methionine aligns with the initiation methionine previously described for the murine Ah-receptor (Kozak, M. *Nuc. Acids Res.* 15:8125–8132 (1987)), and has a stop codon 171 nucleotides immediately upstream. Clone 91A contains 2.27 kb of the 3' untranslated region (3' UTR) of the human Ah-receptor cDNA. To complete the 3' UTR, the rapid amplification of cDNA ends (RACE) method was used on HepG2 mRNA (Frohman, M. A., in *PCR Protocols: A Guide to Methods and Applications*, M. A. Innis, D. H. Gelfand, J. J. Sninsky, T. J. White, Eds. (Academic Press, Inc., San Diego, 1990), pp. 28–38.). Using two primers, OL-100 and OL-101, specific to the 3' end of 91A, a single species of 1.1 kb was amplified. These two primers read as follows:

OL-100: 5' CCATCGATCTCGAGAGATTGCAGATAG-CAAGGTTTGGTGC 3' (SEQUENCE ID. NO. 8).

OL-101: 5' CCATCGATCTCGAGTGTAATGAGT-GAATTGAATGGTGC 3' (SEQUENCE ID. NO. 9).

wherein A is adenine, T is thymine, G is guanine and C is cytosine.

The 5' end of this clone aligned with 91A for 0.48 kb to nucleotide 4640 where the two sequences diverged.

(ii) The Genes and Proteins of the Invention

The nucleic acid sequence for the murine Ah receptor is shown in Sequence ID. NO. 1. Additionally, the nucleic acid sequence for the human Ah receptor is shown in Sequence ID. No. 3. These nucleic acid sequences can be altered, and substitutions, additions, or deletions that provide functionally equivalent molecules can be made.

In addition, the recombinant Ah receptor protein encoding the nucleic acid sequences of this invention may be engineered so as to modify processing or expression of the Ah receptor protein.

The four murine clones of the Ah-receptor encode 805 amino acids (See Sequence ID. NOS. 1 & 2). Based upon knowledge of the N-terminal amino acid sequence of this protein, it was concluded that the Ah-receptor, as found in vivo (i.e. after cleavage of a leader peptide and the initiation methionine) is a 796 amino acid protein with a calculated molecular weight of 89,426 daltons and an isoelectric poing of 5.98. This calculated molecular weight is within 6% of the 95 kD predicted by analysis of the Ah-receptor by SDS-PAGE (Poland, A., Glover, E., & Bradfield, C. A., *Mol. Pharmacol.*, 39:20–6 (1991)) and the predicted PI is similar to that recently reported by two-dimensional gel electrophoresis of the protein 5.2–5.7. The more acidic nature of the protein as found in vivo may be attributable to receptor phosphorylation, a phenomenon which has experimental support. Perdew, G. H., & Hollenback, C. E., *Biochemistry*, 29:6210–4 (1990); Pongratz, I., Stromstedt, P. E., Mason, G. G. F., & Poellinger, L., *J. Biol. Chem.* 266:16813–16817 (1991).

Figure 1:
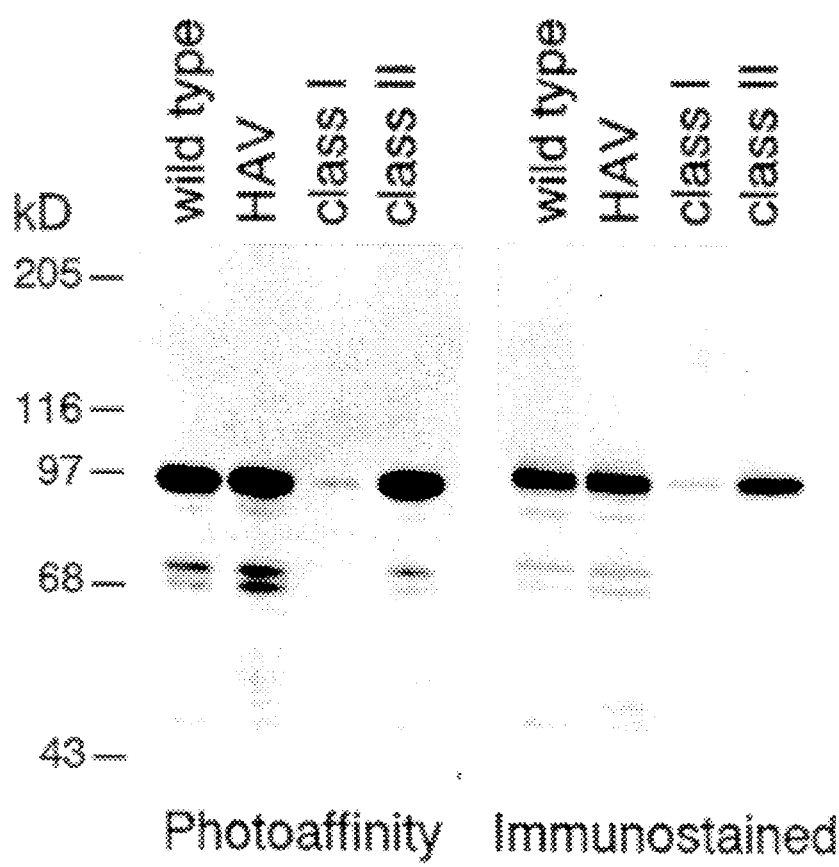
FIG. 1 shows detection of the Ah receptor in Wild-Type and Mutant Hepa-1c1c7 cells.
Figure 3:
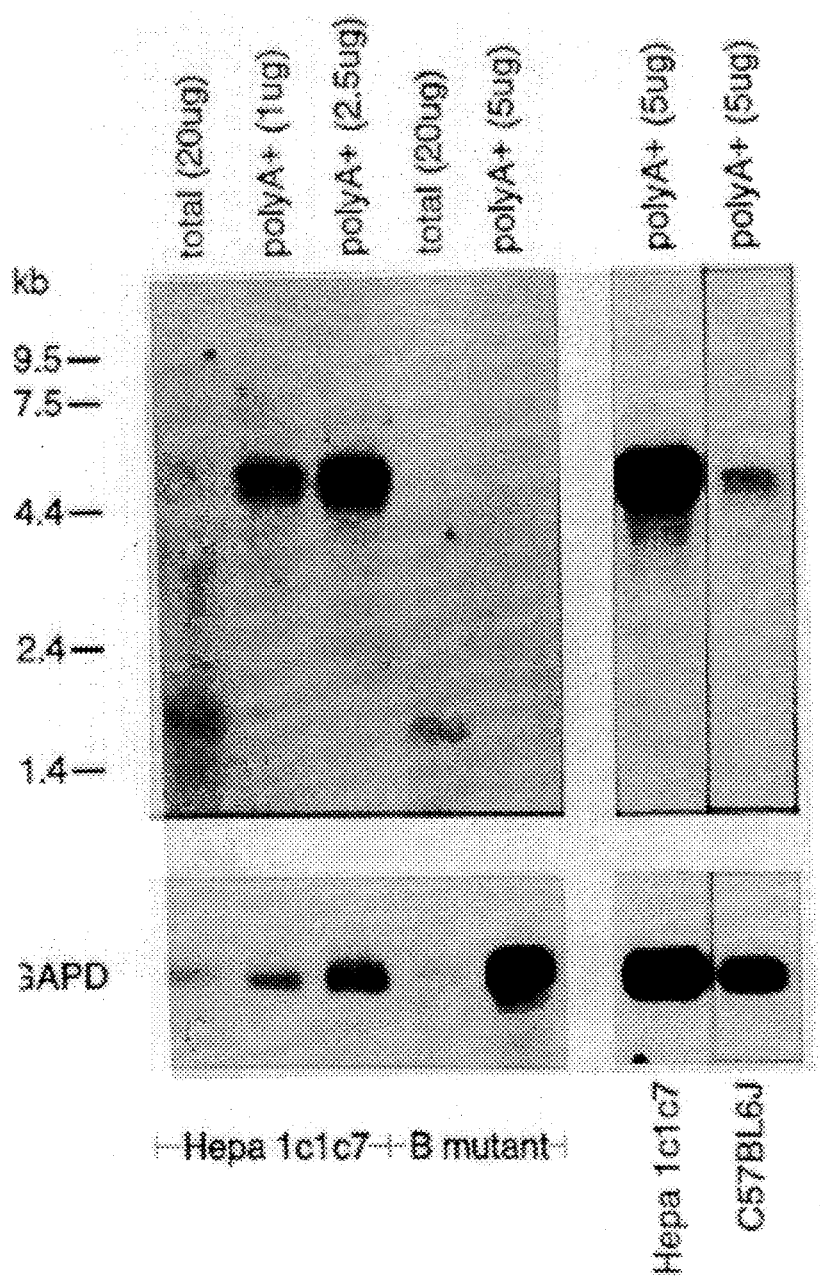
FIG. 3 shows Northern blot analysis of wild type and class I mutant Hepa 1c1c7 cells.

To estimate the size of the Ah-receptor mRNA, Northern analysis was performed on both total and poly(A) RNA isolated from Hepa 1c1c7 cells and the class I mutants. Using either the 0.42 kb (See FIG. 3) or the 1.4 kb EcoRI fragments of cAh1 as the hybridization probe, an mRNA species of approximately 5.4 kb was detected in the Hepa 1c1c7 cells. A minor band of approximately 5.2 kb was present in all cells and tissue samples and may represent an alternatively spliced transcript. The class I mutants, which expressed a very low level of the Ah-receptor protein (See FIG. 1), had an undetectable expression of this 5.4 kb (or 5.2 kb) message under these same analysis conditions (See FIG. 3). Thus, the patter of mRNA expression detected using the isolated cDNA as a probe is in agreement with what is seen at the protein level for the Ah-receptor.

Figure 5:
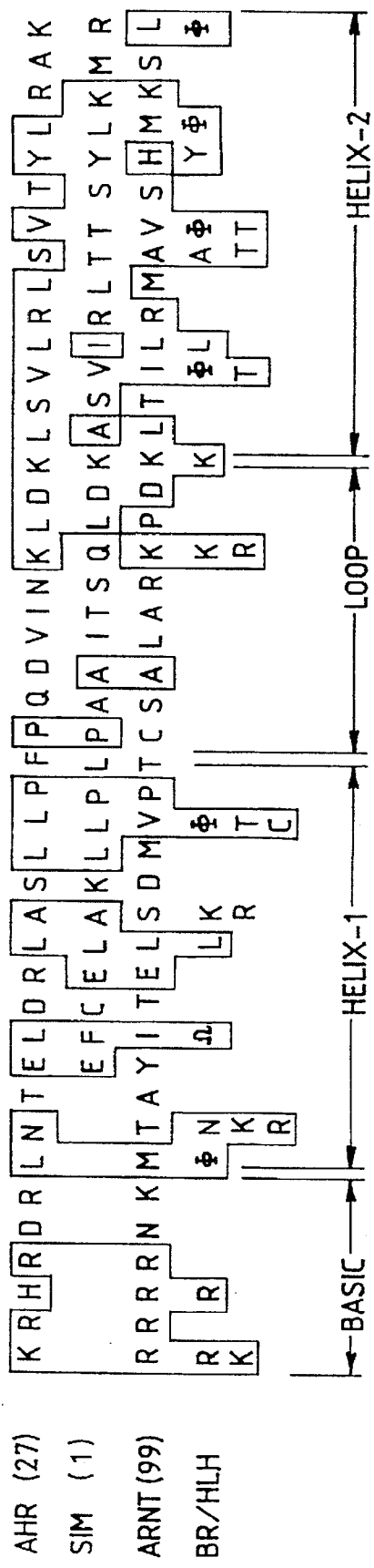
FIG. 5 shows the alignment of the basic helix-loop-helix domains of Ah-receptor (AHR), Sim, and ARNT.

Analysis of the primary amino acid sequence along with sequence comparison of the murine Ah-receptor was compared with proteins such as the Drospholia single-minded protein, Sim, and circadian rhythm protein, Per, and the human Ah-receptor nuclear translocator (ARNT) protein. This comparison provided insights into potential functional domains of the Ah protein. All of these protein contain a homologous region of approximately 200 amino acids termed the PAAS domain (Per, ARNT, Ah-receptor, Sim). Nambu, J. R., Lewis, J. O., Warton Jr., K. A., Cres, S. T., *Cell* 67:1157–1167 (1991). Adjacent to this domain in Sim, ARNT and the Ah-receptor is a basic region/helix-loop-helix motif (BR/HLH) similar to that found in many heterodimeric transcription factors. Weintraub, H., et al., *Science* 251:761–766 (1991); Blackwood, E. M., Eisenman, R. N., *Science* 251:1211–1217 (1991). See FIG. 5. The Ah-receptor and ARNT contain domains involved in the formation of heterodimeric DNA binding complexes and both proteins appear to be part of the TCDD induced complex that binds to DRE sequences which suggests that these two proteins are dimeric partners which act coordinately to regulated the expression of a number of genes.

In addition to the high sequence homology at their N-termini, the Ah-receptor, Sim, and ARNT all have glutamine-rich C-termini. Glutamine-rich sequences have been described in several transcription factors (e.g., Sp1 and OTF-2) and have been characterized as activation domains. Courey, A. J. & Tjian, R., *Cell* 55:887–98 (1988); Gerster, T., Balmaceda, C. & Roeder, R. G., *EMBO J.* 9:1635–1643 (1990); Laurent, B. C., Treitel, M. A. & Carlson, M., *Mol. Cell. Biol.* 10:5616–5625 (1990). The presence of this domain in the Ah-receptor and ARNT suggests that both proteins may be involved in the transcriptional activation of dioxin-responsive genes. Within the glutamine rich segments of the Ah-receptor and Sim is a concentrated cluster of glutamine residues in which 12 of 21 amino acids in Sim and 11 of 21 in the Ah-receptor are glutamine. Similar glutamine-rich regions have been described in several developmentally regulated and tissue specific gene products from Drosophila to humans. These regions have been termed opa repeats and are defined at the nucleotide level as CAX repeats where X=G,A (encoding glutamine) or C (encoding histidine). Wharton, K. A., Yedvobnick, B., Finnerty, V. G. & Artavanis, T. S., *Cell* 40:55–62 (1985).

Figure 4:
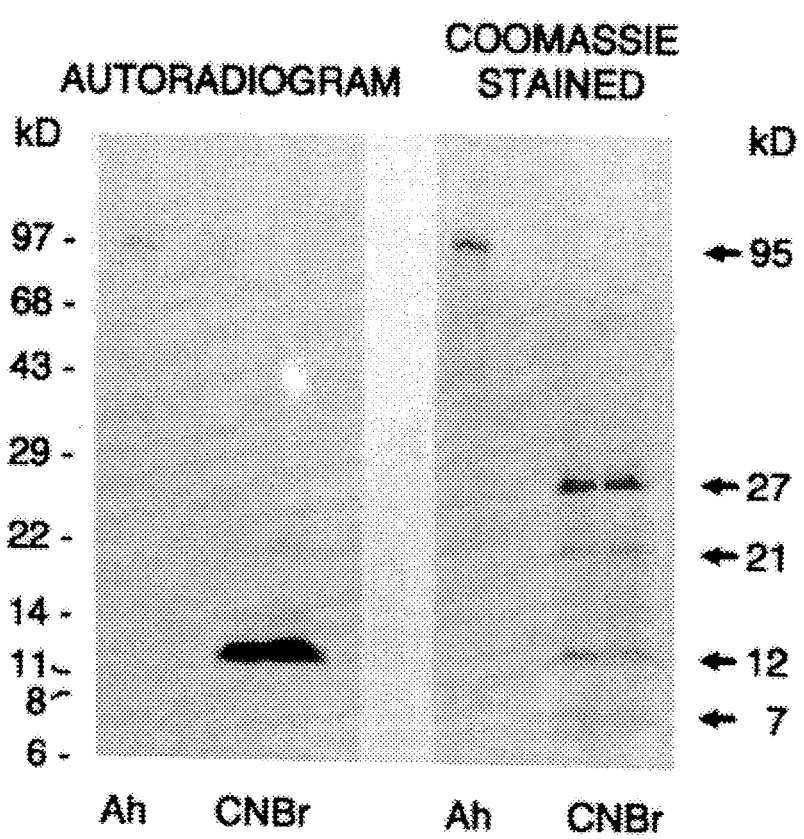
FIG. 4 shows peptide mapping and amino acid sequencing of internal fragments generated by CNBr.

Cyanogen bromide cleavage (CNBr) provides additional information regarding cDNA. CNBr fragmentation experiments provide insights into the domain structure of the Ah-receptor. By photaffinity labeling the Ah-receptor prior to cleavage with CNBr, the region of the protein which was covalently bound by radioligand was identified. The autoradiogram of the CNBr fragments (See FIG. 4) identifies the 12 kd band as the major photaffinity labeled fragment (>95% of radiolabel after purification). This locates the photoaffinity ligand bound residue(s) of the Ah-receptor to amino acids 232–334 as defined by the sequence known to follow methionine 231 and the predicted C-terminal cleavage site, methionine 334.

Figure 6B:
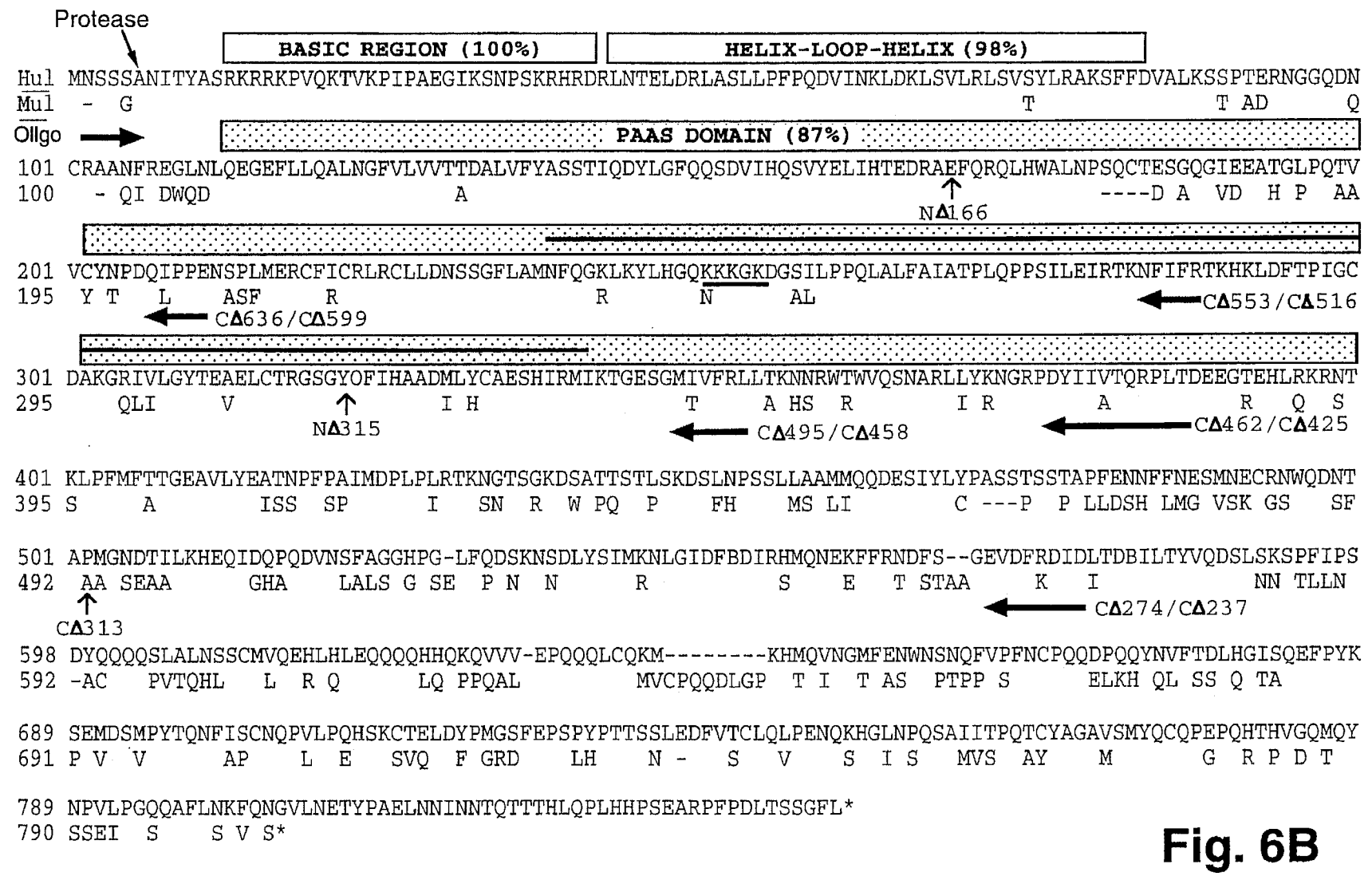

A comparison of the deduced amino acid sequence of the human and murine Ah-receptor cDNAs revealed that the N-terminal half of the two proteins are highly conserved with 100% sequence identity in the basic region, 98% in the helix-loop-helix domain, and 87% in the PAAS domain. See FIG. 6B. In contrast, the C-terminal amino acid sequence of the two proteins is highly variable, displaying only 60% sequence identity.

Figure 9:
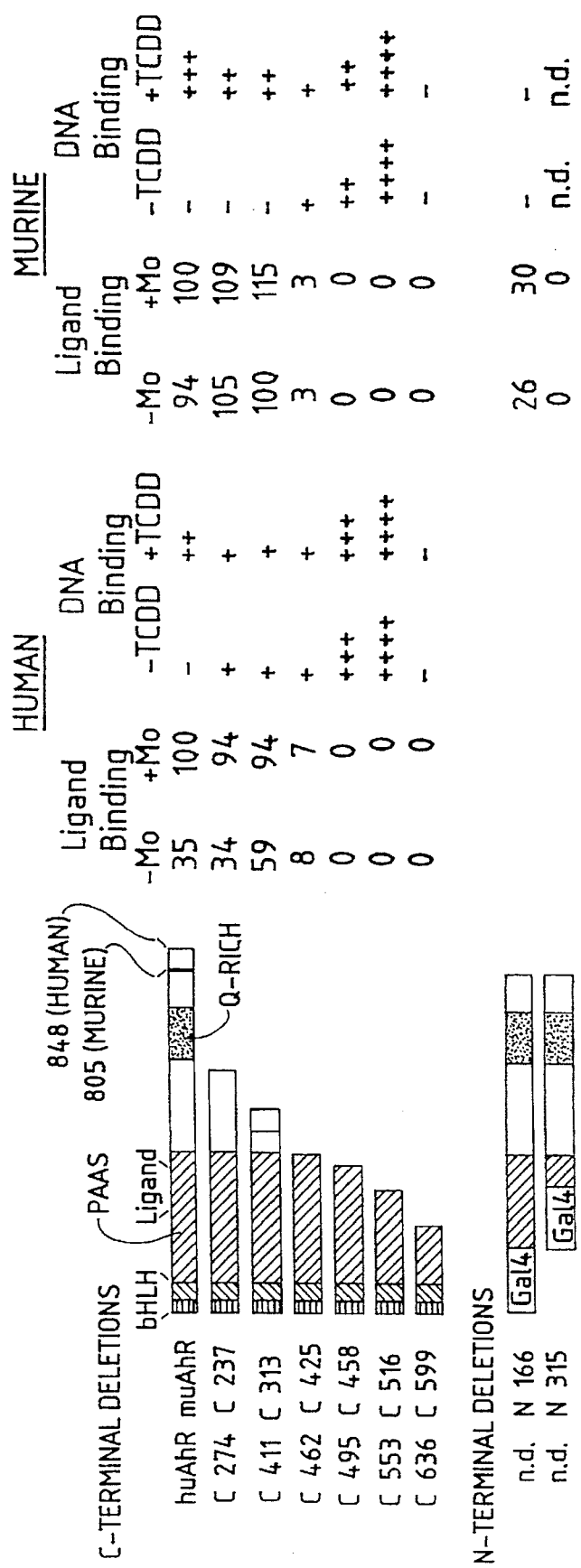
FIG. 9 shows deletion analysis of the human and murine Ah-receptors.
Figure 9:
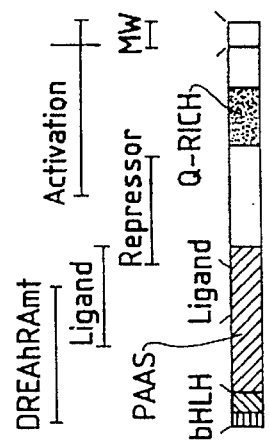

To characterize the functional domain map of the Ah-receptor, a series of deletion mutants were constructed and their capacity to bind ligand and the DRE was analyzed (See FIG. 9). For the murine receptor, C-terminal deletions of up to 313 amino acids (CΔ313) did not significantly affect ligand binding function. However, the CΔ425 mutant displayed decreased ligand binding by about 95%. Since this mutant retains the ability to bind ligand (about 10-fold over background), and the truncation of 33 additional amino acids from the C-terminus (CΔ458) completely abolished ligand binding activity, CΔ425 can be used to define the approximate C-terminal boundary of the domain required for ligand binding. To define the N-terminal boundary of this domain, N-terminal deletion mutants/chimeras containing the DNA binding domain of the Gal4 protein were used. A fusion protein missing 166 amino acids from the N-terminus (NΔ166) retained the capacity to bind ligand, while the deletion of 315 amino acids from the N-terminus (NΔ315) abolished ligand binding. Therefore, NΔ166 defined the approximate N-terminal boundary of the ligand binding domain.

Once the ligand binding domain was identified, characterization of the domains required for DRE binding was described. It was predicted that mutations in a number of functionally distinct domains, such a those required for ligand activation, Hsp90 association and dimerization with ARNT would have an impact on DRE binding. Because none of the Ah-receptor constructs bound the DRE in the absence of ARNT and ARNT did not bind the DRE alone, only Ah-receptor/ARNT heterodimers are able to bind to the DRE. It was discovered that the Gal4/Ah-receptor chimera, NΔ166, which was missing in the bHLH domain, does not bind to the DRE. The deletion mutant CΔ516 appeared to define the C-terminal boundary of a domain required for DRE binding suggesting that residues in the PAAS domain as far as 245 residues form the N-terminal basic domain play a role in DRE/Ah-receptor-ARNT complex formation (See FIG. 9). Finally, it was discovered that the domain involved in receptor activation to a DRE binding form is located within the C-terminal 313 amino acids of the protein. This domain is defined by the CΔ237 and CΔ313 mutants which display decreasing ligand-activated DRE binding when compared to the full length receptor, but did not exhibit decreased ligand binding. (See FIG. 9).

Both CΔ458 and CΔ516 bound the DRE without ligand activation. This suggested that the C-terminal delection of 458 amino acids removed a domain with a role in repressing the DRE binding activity of the receptor. Many laboratories have observed that the presence of oxyanions, such as molybdate lead, results in dramatic improvements in ligand binding while inhibiting ligand activated receptor binding to DNA. Meshinchi, S., Grippo, J. F., Sanchez, E. R., Bresnick, E. H., Pratt, W. B., *J. Biol. Chem.* 263:16809–16817 (1988); Hutchison, K. A., et al., *J. Biol. Chem.* 267:2902–2908 (1992). Molybdate appears to act via stabilization of an Ah-receptor-Hsp90 complex. Manchester, D. K., Gordon, S. K., Golas, C. L., Roberts, E. A., Okey, A. B., *Cancer Res.*, 47:4861–4868 (1987). The effects of molybdate are observed on receptor isolated from essentially all species and murine strains except the receptor isolated from the C57BL/6J mouse. Cuthill, S., Poellinger, L., Gustafsson, J., *J. Biol. Chem.* 262:3477–3481 (1987). It was observed that ligand binding to the human receptor can be improved (consistently 3-fold) and DRE inhibited by the presence of sodium molybdate, while no changes were observed for the murine form. (See FIG. 9.) Since the effect of molybdate on the human Ah-receptor's capacity to bind lignad was highly reproducible, an attempt to map this domain as made. The human deletion mutant CΔ274 exhibited the same molybdate-induced enhancement of ligand binding as the full length numan receptor, while the deletion of 411 amino acids (CΔ411) weakened the ability of molybdate to stabilize the receptor. Finally, the deletion of 462 (CΔ462) amino acids from the C-terminus completely abolished the molybdate effect. These results allowed the mapping of the molybdate stabilization domain between mutants CΔ274 and CΔ462 (See FIG. 9). It was observed that the human receptor mutants CΔ274, CΔ411, and CΔ462 begin to acquire ligand-independent DRE binding. This supports the hypothesis that this domain is involved in the association of the receptor with Hsp90 which acts as a repressor of DRE binding activity.

(iii) Expression of the Ah receptor

The cDNA molecule can be expressed by a variety of means including in a eukaryotic cell. Also, the Ah receptor and polypeptide derivatives of the Ah receptor can be expressed by recombinant techniques when a DNA sequence encoding the relevant molecule is functionally inserted into a vector. By "functionally inserted" is meant in proper reading frame and orientation, as is well understood by those skilled in the art. Typically, the Ah receptor gene will be inserted downstream from a promoter and will be followed by a stop codon, although production as a hybrid protein followed by cleavage may be used, if desired. In general host-cell-specific sequences improving the production yield of Ah receptor and Ah receptor polypeptide derivatives will be used and appropriate control sequences will be added to the expression vector, such as enhancer sequences, polyadenylation sequences, and ribosome binding sites.

Once the appropriate coding sequence is isolated, it can be expressed in a variety of different expression systems, or it can be inserted into the genome for transgenic expression. WO 9203471 is partially set out to provide general background information regarding gene expression in different systems.

Mammalian Expression Systems

A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, typically located within 100 to 200 bp upstream of the TATA box. An upstream promoter element determines the rate at which transcription is initiated and can act in either orientation (Sambrook et al., (1989) Expression of Cloned Genes in Mammalian Cells," in *Molecular Cloning: A Laboratory Manual*, 2nd ed.).

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated (inducible), and depending on the promoter can be induced with glucocorticoid in hormone-responsive cells.

The presence of an enhancer element (enhancer), combined with the promoter elements described above, will typically increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotide from the promoter (Maniatis et al., (1989) *Molecular Biology of the Cell*, 2nd ed.). Enhancer elements derived from viruses may be particularly useful, because they typically have a broader host range. Examples include the SV40 early gene enhancer (DiJkema et al. (1985) *EMBO J.* 4:761) and the enhancer/promoters derived from the long terminal repeat (LTR) of the Rous Sarcoma Virus (Gormal et al., (1982b) *Proc. Natl. Acad. Sci.* 79:6777) and from human cytomegalovirus (Boshart et al., (1985) *Cell* 41:521). Additionally, some enhancers are regulatable and become active only in the presence of an inducer, such as a hormone or metal ion (Sassone-Corsi and Borelli (1986) *Trends Genet.* 2:215; Maniatis et al., (1987) *Science* 236:1237).

A DNA molecule may be expressed intracellularly in mammalian cells. A promoter sequence may be directly linked with the DNA cloned upstream of a cDNA of interest and that cDNA expressed.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell. The adenovirus tripartite leader is an example of a leader sequence that provides for secretion of a foreign protein in mammalian cells.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birnstiel et al., (1985) *Cell* 41:349; Proudfoot and Whitelaw (1988) "Termination And 3' end processing of eukaryotic RNA." In *Transcription and splicing* (ed. B. D. Hames and D. M. Glover); Proudfoot (1989) *Trends Biochem. Sci.* 14:105).

These sequences direct the transcription of an mRNA which can be translated into the polypeptide encoded by the DNA. Examples of transcription terminator/polyadenylation signals include those derived from SV40 (Sambrook et al (1989) "Expression of cloned genes in cultured mammalian cells." In *Molecular Cloning: A Laboratory Manual*).

Some genes may be expressed more efficiently when introns (also called intervening sequences) are present. Several cDNAs, however, have been efficiently expressed from vectors that lack splicing signals (also called spliced donor and acceptor sites) (see e.g., Gothing and Sambrook (1981) *Nature* 293:620). Intrans are intervening noncoding sequences within a coding sequence that contain spliced donor and acceptor sites. They are removed by a process called "splicing" following polyadenylation of the primary transcript (Nevins (1983) *Ann. Rev. Biochem,* 52:441; Green (1986) *Annu. Rev. Genet.* 20:671; Padgett et al., (1986) *Annu. Rev. Biochem.* 55:1119; Krainer and Maniatis (1988) "RNA splicing." In *Transcription and solicina* (ed. B. D. Hames and D. M. Glover)).

Typically, the above described components, comprising a promoter, polyadenylation signal, and transcription termination sequence are put together into expression constructs. Enhancers, introns with functional splice donor and acceptor sites, and leader sequence also be included in an expression construct, if desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 (Gluzman (1981) *Cell* 2523:175) or polyomavirus, replicate to extremely high copy number in the presence of the T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2 (Kaufman et al., (1989) *Mol. Cell. Biol.* 9:946 and pHEBO (Shimizu et al., (1986) *Mol. Cell. Biol.* 6:1074).

Alternatively, foreign proteins can also be targeted to the membrane of a mammalian cell. If the cDNA expression construct includes an amino-terminal hydrophobic leader sequence, and one or more additional internal hydrophobic domains of sufficient size to span the cell membrane (typically −20 amino acids), the resulting protein can be targeted to the cell membrane and retained there in a conformation dependent on the nature and characteristics of the internal hydrophobic domains. (Wickner W. T. and Lodish H. F., *Multiple Mechanisms of Protein Insertion into and Across Membranes,* Science 300:400–407 (1985)). (Hereby incorporated by reference).

Baculovirus Expression System

A baculovirus promoter is any DNA sequence capable of binding a baculovirus RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Expression may be either regulated or constitutive.

Sequences encoding genes abundantly transcribed at late times in the infection cycle provide particularly useful promoter sequences. Examples include sequences derived from the polyhedrin (Friesen et al., (1986) "The Regulation of Baculovirus Gene Expression," in: *The Molecular Biology of Baculoviruses* (ed. Walter Doerfler); E.P.O. Pub. Nos. 127,839 and 155,476) and pl0 (Vlak et al., (1988) *J. Gen. Virol.* 69:765) genes. A DNA molecular may be expressed intracellularly. A promoter sequence may be directly linked with the DNA molecule, in which the case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative to direct expression. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the N-terminus of the polyhedrin gene may be linked at the 5' terminus of a foreign gene and expressed in yeast. The DNA sequence at the junction of the two amino acid sequences may or may not encode a cleavable site. See e.g., Luckow et al., (1988) *Bio/technology* 6:47.

Alternatively, foreign proteins can also be secreted from the cell by creating chimeric DNA molecules that encode a fusion protein comprised of a leader sequence fragment that provides for secretion of the foreign protein in insects. The leader sequence fragment typically encodes a signal peptide comprised of hydrophobic amino acids which direct the secretion of the protein from the cell.

DNA encoding suitable signal sequences can be derived from genes for secreted insect or baculovirus proteins, such as the baculovirus polyhedrin gene (Carbonell et al., (1988) *Gene* 73:409). Alternatively, leaders of non-baculovirus origin, such as those derived from genes encoding human alpha-interferon (Maeda et al., (1985) *Nature* 315:592), human gastrin-releasing peptide (Lebacq-Verheyden et al., (1988) *Molec. Cell. Biol.* 8:3129), human IL-2 (Smith et al., (1985) *Proc. Natl. Acad. Sci. USA* 82:8404), mouse IL-3 (Miyajima et al., (1987) *Gene* 58:273), and human glucocerebrosidase (Martin et al., (1988) *DNA* 7:99) also provide for secretion in insects.

Typically, transcription termination sequences recognized by insects are regulatory regions located 3' to the translation stop codon, and thus together with the promoter flank the coding sequence. These sequences direct the transcription of an mRNA which can be translated into the polypeptide encoded by the DNA. Examples include transcription termination sequences derived from the polyhedrin gene (Miller et al., (1988) *Ann. Rev. Microbiol.* 42:177). Prior to insertion of the foreign gene into the baculovirus genome, the above described components, comprising a promoter, leader (if desired), coding sequence of interest, and transcription termination sequence, are typically put together into an intermediate transplacement construct. Intermediate transplacement constructions are often maintained in a replicon, such as an extrachromosomal element (e.g., plasmids) capable of stable maintenance in a host, such as bacteria. The replicon will have a replication system, thus allowing it to be maintained in a prokaryotic host for cloning and amplification. The promoter and transcription termination sequence of the construct will typically comprise a 2.5 kb section of the baculovirus genome for integration of the foreign gene into the baculovirus genome by double crossover recombination events, producing a baculovirus expression vector (Miller et al., (1989) *Bioessays* 4:91). The baculovirus expression vector is typically packaged into an infectious recombinant baculovirus.

When using baculovirus expression vectors, selectable markers are, such as antibiotic resistance genes, are generally not used. Selection is typically by visual inspection for occlusion bodies. Examples are given elsewhere in this specification of the use of selectable markers.

Recombinant baculovirus expression vectors have been developed for infection into several insect cells. For example, recombinant baculoviruses have been developed for inter alia: *Aedes aegytpi, Autographa californica, Bombyx mori, Drosophila melangaster, Heliothis zea,* Spodopters Frugiperda, and Trichoplusiain (P.C.T. WO 89/046699; Carbonell et al., (1985) *J. Virol.* 56:153: Smith et al., (1983) *Mol. Cell. Biol.* 3:2156; Wright (1986) *Nature* 321:718; See generally, Fraser et al., (1989) *In Vitro Cell. Dev. Biol.* 25:225).

Methods of introducing exogenous DNA into insect hosts are well-known in the art, and typically include either the transfection of host insect cells with DNA or the infection of insect cells or live insects, usually larvae, with virus. Transfection procedures are based on the calcium phosphate procedure originally developed for mammalian cells (Graham et al., (1973) *Virology* 52:456). DNA transfection and viral infection procedures usually vary with the insect genus to be transformed. See e.g. Autograph (Carstens et al., (1980) *Virology* 101:311), Heliothis (virescens) (P.C.T. Pub. No. W088/02030), Spodoptera (Kang (1988) "Baculovirus Vectors for Expression of Foreign Genes," in *Advances in Virus Research,* vol. 35).

Bacterial Expression Systems

A bacterial promoter is any DNA sequence capable of binding bacterial RNA polymerase and initiating the downstream (3') transcription of a coding sequence (e.g., structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli* (Raibaud et al., (1984) *Annu. Rev. Genet.* 18:173). Regulated expression may therefore be either positive or negative, thereby either enhancing or reducing transcription.

Sequences encoding metabolic pathway enzymes provide particularly useful promoter sequences. Example include promoter sequences derived from sugar metabolizing enzymes, such as galactose, lactose (lac) (Chang et al., (1977) *Nature* 198:1056), and maltose. Additional examples include promoter sequences derived from biosynthetic enzymes such as tryptophan (trp) (Goeddel et al., (1980) *Nuc. Acids Res.,* 8:4057; Yelverton et al., (1981) *Nucl. Acids Res.* 9:731; U.S. Pat. No. 4,738,921; E.P.O. Pub. Nos. 36,776 and 121,775). The y-lactamase (bla) promoter system (Weissmann (1981) "The cloning of interferon and other mistakes." In *Interferon* 15 3 (ed. I. Gresser), bacteriophage lambda PL (Shimatake et al., (1981) *Nature* 292:128) and T5 (U.S. Pat. No. 4,689,406) promoter systems also provide useful promoter sequences. In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both tro promoter and lac operon sequences that is regulated by the lacrepressor (Amann et al., (1983) *Gene* 25:167; de Boer et al., (1983) *Proc. Natl. Acad. Sci.* 80:21). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to product high levels of expression of some genes in prokaryotes. The bacteriophage T7 RNA polymerase/promoter system is an example of a coupled promoter system (Studier et al., (1985) *Proc. Natl. Acad. Sci.* 82:1074). In addition, a hybrid promoter can also be comprised of a bacteriophage promoter and an *E. coli* operator region (E.P.O. Pub. No. 267,851).

In addition to a functioning promoter sequence, an efficient ribosome binding site is also useful for the expression of foreign genes in prokaryotes. In *E. coli,* the ribosome binding site is called the Shine-Dalgarno (SD) sequence and includes an initiation codon (ATG) and a sequence 3–9 nucleotides in length located 3–11 nucleotides upstream of the initiation codon (Shine et al., (1975) *Nature* 254:34). The SD sequence is thought to promote binding of mRNA to the ribosome by the pairing of bases between the SD sequence and the 3' and of *E. coli* 16S rRNA (Steitz et al., (1979) "Genetic signals and nucleotide sequences in messenger RNA." In *Biological Regulation and Development: Gene Expression* (ed. R. F. Goldberger)). To express eukaryotic genes and prokaryotic genes with weak ribosome-binding site (Sambrook et al., (1989) Expression of Cloned genes in *Escherichia coli."* In *Molecular Cloning: A Laboratory Manual*).

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo or in vitro incubation with a bacterial methionine N-terminal peptidase (E.P.O. Pub. No. 219,237).

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene (Nagai et al., (1984) *Nature* 309:810). Fusion proteins can also be made with sequences from the lac Z (Jia et al., (1987) *Gene* 60:197), trpE (Allen et al., (1987) *J. Biotechnol.* 5:93; Makoff et al., (1989) *J. Gen. Microbiol.* 135:11), and CheY (E.P.O. Pub. No. 324, 647) genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated (Miller et al., 91989) *Bio/Technology* 7:698).

Alternatively, foreign proteins can also be secreted from the cell by creating chimeric DNA molecules that encode a fusion protein comprised of a signal peptide sequence fragment that provides for secretion of the foreign protein in bacteria (U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell(gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the E. coli outer membrane protein gene (ompA) (Masui et al., (1983), in: *Experimental Manipulation of Gene Expression;* Ghrayeb et al., (1984) *EMBO J.* 3:2437) and the *E. coli* alkaline phosphatase signal sequence (phoA) (Oka et al., (1985) *Proc. Natl. Acad. Sci.* 82:7212). As an additional example, the signal sequence of the alphaamylase gene from various Bacillus strains can be used to secrete heterologous proteins from *B. subtilis* (Palva et al., (1982) *Proc. Natl. Acad. Sci. USA* 79:5582; E.P.O. Pub. No. 244,042).

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromosomal element (e.g., plasmids) capable of stable maintenance in a host, such—as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (E.P.O. Pub. No. 127, 328). Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline (Davies et al., (1978) *Annu. Rev. Microbiol.* 32:469). Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: Bacillus subtilis (Palva et al., (1982) *Proc. Natl. Acad. Sci. USA* 79:5582; E.P.O. Pub. Nos. 36,259 and 63,953; P.C.T. WO 84/04541), *escherichia coli* (Shimatake et al., (1981) *Nature* 292:128; Aman et al., (1985) *Gene* 40:183; Studier et al., (1986) *J. Mol. Biol.* 189:113; E.P.O. Pub. Nos. 36,776, 136,829 and 136,907; U.K. Patent Application Serial No. 8418273), Streptococcus cremoris (Powell et al., (1988) *Appl. Environ. Microbiol.* 54:655); Streptococcus liyidans (Powell et al., (1988) *Appl. Environ. Microbiol.* 54:655), Streptomyces lividans (U.S. Pat. No. 4,745,056).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., (Masson et al., (1989) *FEMS Microbiol. Lett.* 60:273; Palva et al., (1982) *Proc. Natl. Acad. Sci. USA* 79:5582; E.P.O. Pub. Nos. 36,259 and 63,953; P.C.T. WO 84/04541, Bacillus), (Miller et al., (1988) *Proc. Natl. Acad. Sci.* 85:856; Wange et al., (1990) *J. Bacteriol.* 172:949, Campylobacter), (Cohen et al., (1973) *Proc. Natl. Acad. Sci.* 69:2110; Dower et al., (1988) *Nucleic Acids Res.* 16:6127; Kushner (1978) "An improved method for transformation of *Escherichia coli* with EolEl-derived plasmids." In *Genetic Engineering: Proceedings of the International Symposium on Genetic Engineering* (eds. H. W. Boyer and S. Nicosia); Mandel et al., (1970) *J. Mol. Biol.* 53:159; Taketo (1988) *Biochem. Biophys. Acta* 949:318; Escherichia) (Chassy et al., (1987) *FEMS Microbiol. Lett.* 44:173 Lactobacillus); (Fiedler et al., (1988) *Anal. Biochem.* 170:38, Pseudomonas); (Augustin et al., (1990) *FEMS Microbiol. Lett* 66:203, Staphylococcus), (Barany et al., (1980) *Bacteriol.* 144:698; Harlander (1987) "Transformation of Streptococcus lactis by electroporation," in: *Streptococcal Genetics* (ed. J. Ferretti and R. Curtiss III); Perry et. al., (1981) *Infec. Immun.* 32:1295; Powell et al., (1988) *Anal. Environ. Microbiol.* 54:655; Somkuti et al., (1987) *Proc. 4th Evr. Cona. Biotechnology* 1:412, Streptococcus. Alternatively, foreign proteins can also be targeted to the membrane of a bacterial cell. If the cDNA expression construct includes an amino-terminal hydrophobic leader sequence, and one or more additional internal hydrophobic domains of sufficient size to span the cell membrane (typically −20 amino acids), the resulting protein can be targeted to the cell membrane and retained there in a conformation dependent on the nature and characteristics of the internal hydrophobic domains. (Wicknet W. T. and Lodish H. F., *Multiple Mechanisms of Protein Insertion into*

*and Across Membranes,* Science 300:400–407 (1985)). (Hereby incorporated by reference).

Description: Yeast Expression System

A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydorgenase (ADH) (E.P.O. Pub No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO gene, encoding acid phosphatase, also provides useful promoter sequences (Myanohara et al., (1983) Proc. Natl. Acad. Sci.USA 80:1).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (E.P.O. Pub No. 164556). Furthermore, a yeast promoter can include naturally occurring promoters of non-yeast origin that have the ability to bind yease RNA polymerase and initiate transcription. Examples of such promoters include inter alia, (Cohen et al., (1980) *Proc. Natl. Acad. Sci. USA* 77:1078; Henikoff et al., (1981) *Nature* 283:835; Hollenberg et al., (1981) *Curr. Topics Microbiol. Immunol.* 96: 119; Hollenberg et al., (1979) "The Expression of Bacterial Antibiotic Resistance Genes in the Yeast Saccharomyces cerevisiae," in *Plasmids of Medical, Environmental and Commercial Importance* (eds. K. N. Timmis and A. Puhler; Mercerau-Puigalon et al., (1980) *Gene* 11:163; Panthier et al., (1980) *Curr. Genet.* 2:109).

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative to direct expression. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g. E.P.O. Pub. No. 196056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein.

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (E.P.O. Pub. No. 13873; J.P.O. Pub. No. 62,096,086) and the A-factor gene (U.S. Pat. No. 4,588, 684). Alternatively, leaders of non-yeast origin, such as an interferon leader, exist that also provide for secretion in yeast (E.P.O. Pub. No. 60057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008; E.P.O. Pub. No. 324274). Additional leaders employing an alpha-factor leader fragment that provides for secretion include hybrid alpha-factor leaders made with a presequence of a first yeast, but a pro-region from a second yeast slphafactor. (See e.g., P.C.T. WO 89/02463).

Typically, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Typically, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al. (1979) *Gene* 8:17–24), pCl/1 (Brake et al., (1984) *Proc Natl. Acad. Sci. USA* 81:4642–4646), and YRp17 (Stinchcomb et al., (1982) *J. Mol. Biol.* 158:157). In addition, a replicon may be either a high or low copy number plasmid. A high copy number plasmid will generally have a copy number ranging from about 5 to about 200, and typically about 10 to about 150.

A host containing a high copy number plasmid will preferably have at least about 10, and more preferably at least about 20. Either a high or low copy number vector may be selected, depending upon the effect of the vector and the foreign protein on the host. See e.g. Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome (Orr-Weaver et al., (1983) *Methods in Enzymol.* 101:228–245). An integrating vector may be directed to a specific locus in yeast by selecting the appropriate homologous sequence for inclusion in the vector. See Orr-Weaver et al., supra. One or more expression construct may integrate, possibly affecting levels of recombinant protein produced (Rine et al., (1983) *Proc. Natl. Acad. Sci. USA* 80:6750). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRPI, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUPI allows yeast to grow in the presence of copper ions (Butt et al., (1987) *Microbiol. Rev.* 51:351).

Alternatively, some of the above described components can be put together into transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: Candida albicans (Kurtz, et al., (1986) *Mol. Cell. Biol.* 6:142), Candida maltosa (Kunze, et al., (1985) *J. Basic Microbiol.* 25:141). Hansenula polymorpha (Gleeson, et al., (1986) *J. Gen. Microbiol.* 132:3459; Roggenkamp et al., (1986) *J. Gen. Genet.* 202:302), Kluyveromyces fragilis (Das, et al., (1984) *J. Bacteriol.* 158:1165), Kluyveromyceslactis (De Louvencourt et al. (1983) *J. Bacterial..* 154:737; Van den Berg et al., (1990) *Bio/Technology* 8:135), Pichia guillerimondii (Kunze et al., (1985) *J. Basic Microbiol.* 25:141), Pichia pastoris (Cregg, et al., (1985) *Mol. Cell. Biol.* 5:3376; U.S. Pat. Nos. 4,827, 148 and 4,929,555), Saccharomyces cerevisiae (Hinnen et al., (1978) *Proc. Natl. Acad. Sci. USA* 75:1929; Ito et al., (1983) *J. Bacteriol.* 153:163) Schizosaccharomyces pombe (Beach and Nurse (1981) *Nature* 300:706), and Yarrowia lipolytica (Davidow, et al., (1985) *Curr. Genet.* 10:380471 Gaillardin, et al., (1985) *Curr. Genet.* 10:49).

Methods of introducing exogenous DNA into yeast hosts are well-known in the art, and typically include either the transformation of spheroplasts or of intact yeast cells treated with alkali cations. Transformation procedures usually vary with the yeast species to be transformed. See e.g., (Kurtz et al. (1986) *Mol. Cell. Biol* 6:142; Kunze et al., (1985) *J. Basic Microbiol.* 25:141; Cardida); (Gleeson et al., (1986) *J. Gen. Microbiol.* 132:3459; Roggenkamp et al., (1986) *Mol. Gen. Genet.* 202:302; Hansenula; (Das et al., (1984) *J. Bacteriol.* 158:1165; De Louvencourt et al., (1983) *J. Bacteriol* 154:1165; Van den Berg et al., (1990) *Bio/Technology* 8:135; Kluyveromyces); (Cregg et al., (1985) *Mol. Cell. Biol.* 5:3376; Kunze et al., (1985) *J. Basic Microbiol.* 25:141; U.S. Pat. Nos. 4,837,48 and 4,929,555; Pichia/(Hinnen et al., (1978) *Proc. Natl. Acad. Sc. USA* 75:1929; Ito et al., (1983) *J. Bacteriol.* 153:163 Saccharomyces); (Beach and Nurse (1981) *Nature* 300:706; Schizosaccharomces); (Davidow et al., (1985) *Curr. Genet.* 10:39; Gaillardin et al. (1985) *Curr. Genet.* 10:49; Yarrowia. Alternatively, foreign proteins can also be targeted to the membrane of a yeast cell. If the cDNA expression construct includes an amino-terminal hydrophobic leader sequence, and one or more additional internal hydrophobic domains of sufficient size to span the cell membrane (typically ~20 amino acids), the resulting protein can be targeted to the cell membrane and retained there in a conformation dependent on the nature and characteristics of the internal hydrophobic domains. (Wickner w. T. and Lodish H. F., Multiple *Mechanisms of Protein Insertion* into and Across *Membranes,* Science 300:400–407 (1985)). (Hereby incorporated by reference).

(iv) The Utility of the Invention

Figure 10:
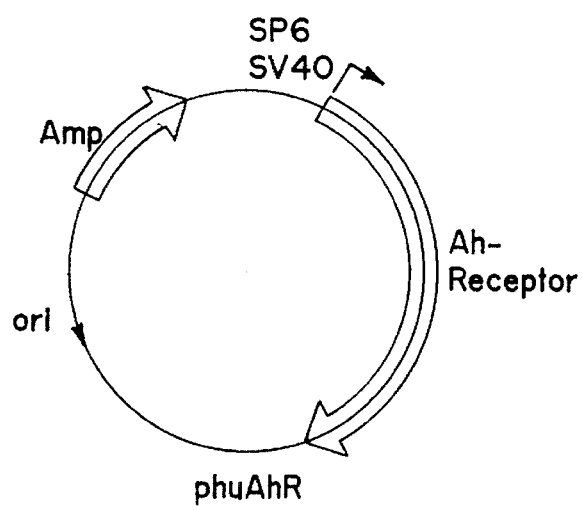
FIG. 10 shows an example of a mammalian expression vector for human AhR.

Assays that recognize the presence of aromatic halogenated toxins such as those in the dioxin family have been developed. Poland et al., U.S. Pat. No. 5,128,244 ('244) hereby incorporated by reference. This patent provides a method of detecting environmental pollutants that are related to 2,3,7,8-tetrachlorodibenzo-p-dioxin (TCDD). The Ah recceptor is used in '244 as a reagent to specifically bind the radiolabeled agonist, [$^{125}$I]-2-iodo-7,8-dibromodibenzo-p-dioxin. Chemicals and environmental samples that compete with this compound for receptor occupancy are assumed to be a receptor agonist and thereby potential toxicants. One of the problems in applying this method lies in the availability of receptor preparations for the assay, especially preparations for human cells. The human and murine cDNA clones can be used to generate significant concentrations of purified Ah-receptor for use in the assay described in the '244 patent or in other assays as well. This can be accomplished by cloning the cDNAs into vectors which allow expression of the protein. An example of a mammalian vector that can be used to generate human AhR is provided in FIG. 10. Other expression systems include, but are not limited to: 1) in vitro expression in reticulocyte lysates, 2) baculovirus, 3) vaccinia virus, 4) yeast, 5) mammalian cells and 6) bacteria.

The Ah-receptor cDNA can be used to generate probes to detect individuals or populations that have altered susceptibility to the toxicity of TCDD and related compounds. Strains of mice exist that have markedly different sensitivities to the effects of receptor agonists. The molecular mechanisms underlying this differential sensitivity are related to subtle sequence differences in the gene that encodes the Ah-receptor. These mutations lead to minor structural differences in receptor function, such that resistant strains of mice have receptors that do not bind agonist as tightly and thereby do not respond as easily. See Poland, A., Palen, D., and Glover, E., *Mol. Pharm.* 46:915–921 (1994). Similar mutations can be identified in human populations. Populations may be screened using PCR to amplify genomic DNA to sequence and identify the target region. Sequence primers for these assays will be derived from the cDNA and genomic clones of the Ah-receptor.

The invention can also be used to generate polyclonal or monoclonal antibodies. The fusion of mouse myeloma cells and spleen cells from immunized mice by Kohler and Milstein in 1975 (*Nature* 256:495–497 (1975)) demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations. In order to produce a monoclonal antibody, a hybridoma clone will have to be produced. The hybridoma can be produced by standard techniques. The hybridoma is produced from the fusion of mouse myeloma cells with splenocytes obtained from a mouse hyperimmunized with single cell suspension containing the Ah-receptor. Next, the hybridoma would be transferred to a growth solution that kills off the unfused cancer cells; the unfused spleen cells will die by themselves. The hybridoma would then begin producing antibodies to the antigen initially injected into the mouse.

(v) Genetically Engineered Cell Systems and an Assays for Detecting Agonists to the Ah Receptor.

Genetically engineered cells, such as yeast and mammalian cells, can be manufactured to express the Ah receptor. Such genetically engineered cells can respond to the presence of agonists like dioxin, thereby activating the Ah receptor. The activation of the Ah receptor can be monitored by the insertion of a reporter gene into the cells.

The yeast cells that can be used in this invention are *Saccharomyces cerevisiae* and *Saccharomyces pombe*. Any strain of *Saccharomyces cerevisiae* or *Saccharomyces pombe* can be transformed as long as the yeast contains heat shock protein 90 or its homologues. Typically, *Saccharomyces cerevisiae* carry two genes which encode heat shock protein homologues. Lindquist, S., and Craig, E. A. (1988). *Annu. Rev. Genet.*, 22, 631–677. One of these homologues, hsc 82, is expressed at high levels and is only moderately heat inducible. The second homologue, hsp 82, is expressed at relatively low levels and is highly heat inducible. Yeast deleted for either gene are viable, while a double mutation is lethal. Id.

For example, a *Saccharomyces cerevisiae* strain known as A303 (Mata, ura 3-52, trp 1A1, his 3Δ200, leu 2Δ1, (obtained from Rick Gaber, Northwestern University), can be used. Strains equivalent to A303 are commercially available. Additionally, strains containing disruptions in the two yeast heat shock protein genes can be used so long as these strains are transformed with a plasmid containing either the hsc 82 or hsp 82 or both. For example, the strain GRS4, (obtained from Susan Lindquist, University of Chicago), contains disruptions in its two heat shock protein genes but can be transformed with the plasmids described in this invention if prior to such transformation, the yeast is first transformed with the plasmid pTT8. Plasmid pTT8, (obtained from Susan Lindquist, University of Chicago), contains the hsp 82 driven by a GAL1 promoter. Plasmid pTT8 is described, although not named as such in Picard, D., Khuraheed, B., Garabedian, M. J., Fortin, M. G., Lindquist, S., and Yamamoto, K. R., (1990), in *Nature* 348: 166–168, hereby incorporated by reference. The result of this genetic manipulation is that the levels of the heat shock protein can be regulated by the presence or absence of galactose in the growth media. When grown in media containing 2% galactose, hsp 82 is expressed at levels comparable to the combined wild-type levels of hsc 82 and hsp 82. Id.

Figure 11:
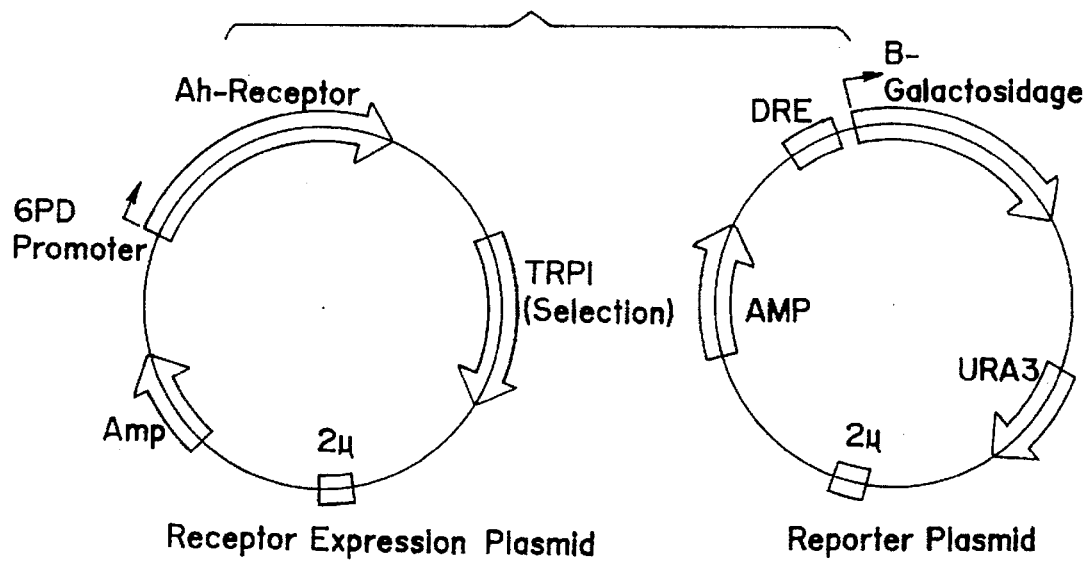
FIG. 11 shows an example of a receptor expression plasmid and a reporter plasmid.

In one embodiment, the yeast strain can be transformed with an expression plasmid(s) expressing the full-length Ah receptor and its dimerization partner, ARNT. The yeast is also transformed with a reporter plasmid expressing a reporter gene, such as lac Z, which is driven by the dioxin responsive element (DRE). The DRE lies upstream of a reporter gene (such as β-galactosidase of luciferase) and is the site where the Ah receptor binds. See FIG. 11. If an agonist, such as dioxin, β-napthoflavone (BNF), α-naphthoflavone (αNF), etc., is present, say in a water, soil or air sample, the agonist will bind to the Ah receptor-ARNT complex generated by the plasmid. The ligand-bound complex will then interact with the DRE expressed by the reporter plasmid. The interaction of the Ah receptor with the DRE will activate transcription of the reporter gene. The reporter gene can then be assayed to determine if an agonist is present.

Figures 14A, 14B, 14C:
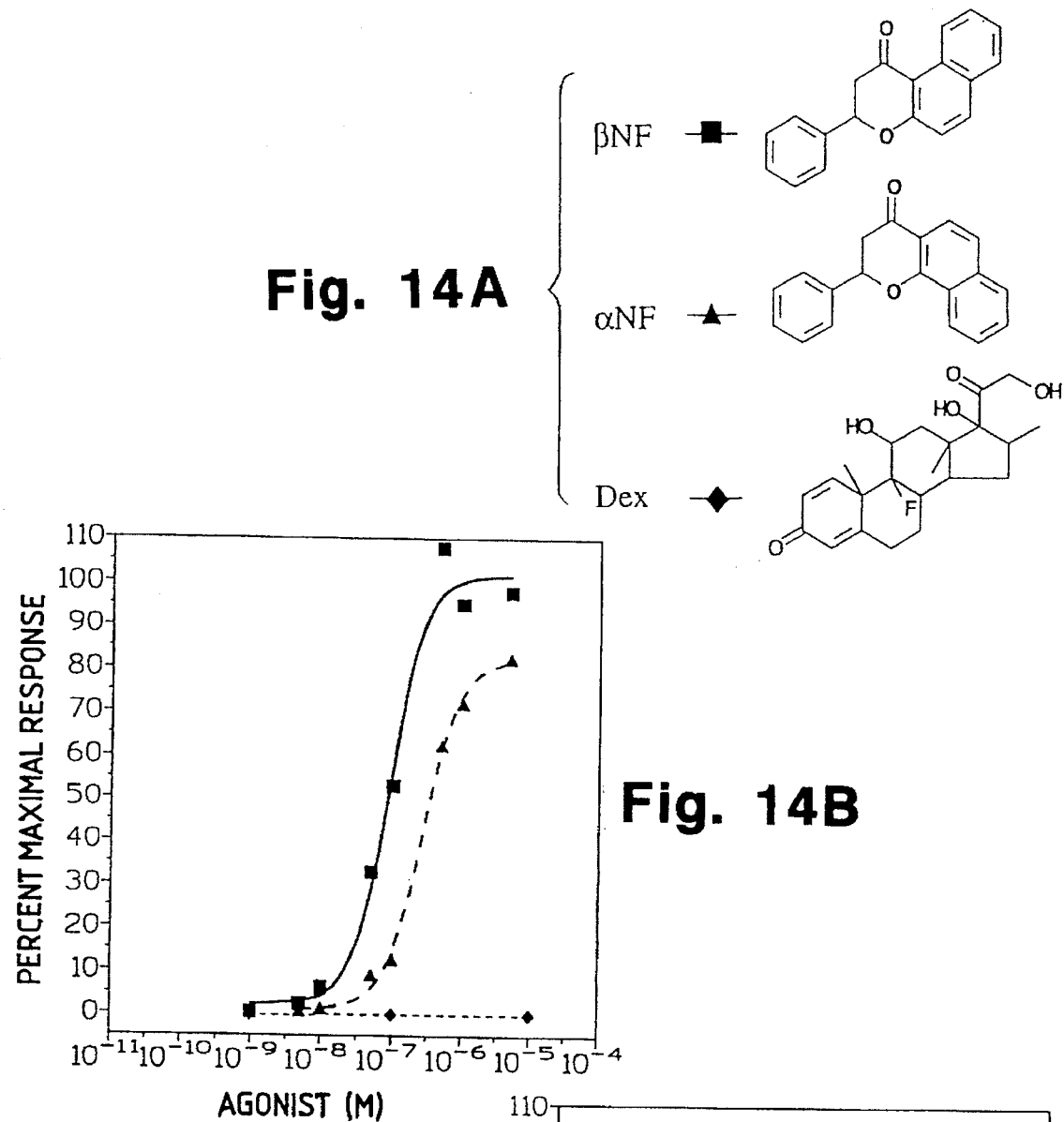
FIGS. 14A, 14B, and 14C show the pharmacology of the Ah Receptor expressed in yeast.

For example, the yeast strain A303 can be genetically transformed with plasmids expressing the the Ah receptor, ARNT, a lac Z gene driven by DRE. The DRE used in the plasmid can be derived from the CYP1A1 promoter or made synthetically. See Denison, M. S., Fisher, J. M., and Whitlock, J. P. J. (1988), *Proc. Natl. Acad. Sci. USA*, 85: 2528–2532. More specifically, strain A303 can be transformed with the plasmid pCWhuAHR, which contains the human Ah receptor, the plasmid pY2ARNT, which contains the AHR nuclear translocator, and a reporter plasmid, pDRE23-Z, which contains DRE and a lac Z gene. When a genetically transformed A303 strain was exposed for 16 to 18 hours to an agonist, a β-galactosidase assay confirmed reporter gene expression. See FIGS. 14A, 14B, and 14C.

In the second embodiment, a yeast strain is transformed with an expression plasmid(s) expressing a a chimeric Ah receptor and a reporter plasmid expressing a reporter gene which is driven by a suitable operator.

The chimeric Ah receptor is prepared by replacing the DNA binding and primary dimerization domains (known as the basic helix-loop-helix domain) of the Ah receptor with the analogous domain from another protein. A fusion protein protocol can be used. In this protocol, the DNA or cDNA of the Ah receptor is fused to the DNA binding domain of another protein, often referred to as a fusion protein. Any fusion protein domain capable of binding specific DNA sequences can be used so long as the target DNA sequences are located upstream of a reporter gene. The result of such manipulation is a chimeric Ah receptor that is able to dimerize with itself and does not require ARNT.

For example, the binding domain of the fusion protein LexA can be used. LexA is a protein found in *E. Coli* that binds as a dimer to specific DNA sequences upstream of target genes such as the bacterial gene RecA involved in DNA repair. Since LexA is void of any transcriptional activity, it normally acts as a repressor of transcription until such time that it is cleared and the repression is relieved allowing the expression of this regulated genes. LexA is often fused to heterologous proteins containing a transactivation domain thus reconstituting a complex transcription factor that can activate expression of genes located downstream of LexA DNA binding sites (LexA operatives). Another protein which can be used is the Gal4 protein. Gal4 normally regulates the expression of genes involved in the pathway for utilizing galactose as a food source.

The reporter plasmid expresses a reporter gene. In order for the reporter gene to function, it must be driven by a suitable operator. The operator contained in the reporter plasmid should contain the binding sites from the binding domain of the fusion protein used to replace the binding domain of the Ah receptor. For example, if the binding domain of a LexA protein is used to form the chimeric Ah receptor, then a LexA operator should be inserted in the reporter plasmid.

In addition to the operator, the reporter plasmid must contain a suitable promoter. There are various types of promoters such as strong promoters which can sustain a high rate of transcription, and weak promoters which are relatively inefficient. With *Saccharomyces cerevisiae*, the GAL promoter is frequently used for expression of foreign genes. However, other suitable promoters known in the art can be used.

For example, *Saccharomyces cerevisiae* strain GRS4, deleted for the hsp 82 and hsc 82 alleles, but which contains the low copy number plasmid pTT8 carrying hsp 82 can be used. GRS4 can be transformed with plasmid pEGAHRNΔ166, which contains the AHR with amino acids 1–167 replaced by residues 1–202 of LexA. The yeast is also transformed with the reporter plasmid, pSH18–34, which is a 2 μ, URA 3-selectable vector containing the GAL1 promoter fused to the bacterial lac Z gene in which the GAL1 upstream activating sequence ($UAS_G$) has been replaced with 8 LexA binding sites.

The inventors have discovered that cells transformed with an expression plasmid(s) containing a chimeric Ah receptor detects agonists in the same manner as the yeast transformed with expression plasmids containing the Ah receptor and ARNT. However, the inventors have discovered that yeast transformed with the chimeric LexA Ah receptor are more sensitive than the Gal4-AHR, and can achieve greater than 100 fold increases in β-galactosidase activity for certain agonists, such as α-NF and β-NF. Yeast transformed with expression plasmids containing the Ah receptor and ARNT activates with 12 fold over background for certain agonists.

In addition to yeast cells, mammalian cells can be transformed. Again, a chimeric Ah receptor is created. A system similar to that used to express the chimeric Ah receptor in yeast cells can be used. The Ah receptor and ARNT or the chimeric Ah receptor can be expressed in mammalian cells by transfection. For example the Gal4 fusion approach can be used. See Kakidani, H., and Ptashne, M. (1988) *Cell* 50, 137–142; Morin, P. J., and Gilmore, T. D. (1992), *Nucleic Acids Res.* 20, 2453–248, Fields, S., and Jang, S. K. (1990) *Science* 29, 1046–10; Giguere, V., Hollenberg, S. M., Rosenfeld, M. G., and Evans, R. M. (1986) *Cell* 46, 645–652. In this protocol, regions of the DNA or cDNA of interest are fused to the DNA binding domain of the yeast Gal4 protein (amino acids 1–147), and the capacity of these chimeras to drive CAT expression from a minimal promoter downstream of the upstream activating sequences that bind Gal4 ($UAS_G$) elements is monitored. See Sadowski, and Ptashne, M. (1989) *Nucleic Acids Res.* 1, 7539.

In order to create the chimeric molecules, any fusion protein can be used. The binding domain of the fusion protein is placed into the plasmid. For example, if Gal4 is used, the binding domain encompasses amino acids 1–147.

After creation of the fusion plasmid, a plasmid containing the full-length Ah receptor or the full-length Ah receptor having deletions at its amino or carboxy-terminal ends is subcloned into compatible sites in the fusion plasmid. Next, a plasmid containing ARNT or ARNT containing deletions is subcloned into compatible sites in another fusion plasmid. A reporter plasmid is then prepared. The reporter plasmid contains the activating and binding sequences of the fusion protein (the operator sequences) and a reporter gene. An example of a suitable operator is $UAS_G$. Once construction of the plasmids is completed, they are transfected into mammalian cells, such as COS-1 cells. However, one skilled in the art would recognize that mammalian cells, other than COS-1 cells could be used.

For example, if the fusion protein Gal4 is used, a pSG4 vector as described in Sadowski and Ptashne, M. (1989) *Nucleic Acids Res.* 17, 7539, hereby incorporated by reference, could be used. The pSG42 vector contains the amino-terminal 147 amino acids of the yeast Gal4 protein under the control of a SV40 promoter, followed by a multiple cloning site that allows in-frame cloning of sequences derived from a second cDNA. Subcloned into this vector is the plasmid pGAHRNΔ166. Plasmid pGAHRNΔ166 contains the Ah receptor containing 166 deletions at its amino terminus. The plasmid pGAHRNΔ166 was generated from the EcoRI, KpnI, BglII, and SacI restriction enzyme fragments of the murine AHR derived from the plasmid pcAHR, and subcloned into the compatible sites of pSG4. Also subcloned into this a fusion protein vector is a plasmid containing ARNT. The plasmid pGARNT can be used. Plasmid pGARNT was constructed by cloning the BamHI fragment from phuARNT (See Dolwick, K. M., Schmidt, J. V., Carver, L. A., Swanson, H. I., and Bradfield, C. A. (1993) *Mol. Pharmacol.* 44, 911–917). The reporter plasmid can be pG5bCAT which is a chloramphenicol acetyltransferase plasmid containing five $USA_G$ elements upstream of the adenovirus E1B Tata box core promoter. Little, J. W. and Green, M. R. (1989) *Nature* 338, 39–44. All of these plasmids can be transfected into COS-1 cells and the COS-1 cells exposed to agonists. If the Ah receptor is activated, then choramphenicol acetyltransferase assays will detect the reporter gene expression.

Regardless of the cell system, any reporter gene can be used. For example, the following reporter genes and their appropriate assays can be used:

| GENE | GENE PRODUCT | ASSAY |
| --- | --- | --- |
| lac Z | β-Galactosidase | Histochemical test |
| neo | Neomycin phosphotransferase | Kanamycin reistance |
| cat | Choloramphenicol acetyltransferase | Chloramphenicol resistance |
| dhfr | Dihydrofolate reductase | Methotrexate resistance |
| aph IV | Hygromycin phosphotransferase | Hygromycin resistance |
| lux | Luciferase | Bioluminescence |
| uid A | β-Glucoronidase | Histochemcial test[1] |

[1]Brown, T. A., Gene Cloning: An Introduction, 2d Edition, pg.213 (1990).

The genetically transformed cells of this invention can be used in an assay to test or detect agonists in environmental samples such as soil, air, and water. The genetically transformed cells of this invention can also be used in an assay to detect agonists in tissue samples. A culture containing the genetically tranformed cells is prepared. The samples to be tested can either be incorporated into agar plates or to a liquid media in which the genetically transformed cells are being propagated. The culture is allowed to grow for approximately 4 to 18 hours to allow for reporter gene expression. Testing for Ah receptor activation can be done by pouring the substrate for the reporter gene directly onto the plate and observing whether there is a colormetric change or whether the cells continue to grow, or, in the case of the liquid assay, by placing the cells in a buffer solution containing the substrate and measuring color change by absorbance on a spectrophometer. Assays can be prepared for use with yeast cells or mammalian cells.

For purposes of explanation and not limitation, the following examples are presented.

EXAMPLE 1: PURIFICATION OP THE Ah RECEPTOR FORM THE C57BL/6J MOUSE

Materials and Methods

Chemicals. Activated charcoal, grade PX-21, was a gift from Amoco Research Corp. (Chicago, Ill.). Bacto-Gelating was from Difco laboratories (Detroit, Mich.). Glacial acetic acid, trichloroacetic acid, and isopropyl alcohol (all reagent grade) were from Fisher Scientific (Fair Lawn, N.J.). Formaldehyde solution (37% v/v), stabilized with 10% methanol (v/v), was from Mallincrodt (St. Louis, Mo.). Silver nitrate was from Amend Drug and Chemical Co. (Irvington, N.J.). HPLC-grade acetonitrile, methanol, and n-propyl alchohol were from Burdick and Jackson Laboratories, Inc. (Muskegon, Mich.). Lithium dodecyl sulfate was from Gallard-Schlessinger Industries Inc. (New York, N.Y.). DEAE-cellulose (DE53) was from Whatman (Clifton, N.J.). Glycerol and formic acid 88%, v/v) were from J. T. Baker (Phillipsburg, N.J.). SDS and ammonium persulfate were from Bethesda Research Laboratories (Gaithsburg, Md.). SDS-PAGE molecular weight standards, bromophenol blue, N, N'-methylene-bis-acrylamide, and acrylamide (99% pure) were from Bio-Rad (Richmond, Calif.). Soybean trypsin inhibitor, Coomassie blue-R250, EGTA, EDTA, Tris (free acid and sodium salt), dithiothreitol, β-mercaptoethanol, phosphocellulose (50–150 μM), sodium azide, CAPS (free acid), MOPS (free acid and sodium salt), and Nonidet P-40 were purchased from Sigma Chemical Co. (St. Louis, Mo.). TFA (99% pure) and dimethyl sulfoxide (anhydrous, 99% pure) were from Aldrich Chemical Co. (Milwaukee, Wis.). Water used in preparation of buffers was deionized; water used in HPLC and straining of gels was deionized and passed through a Milli-Q reaent water system (Millipore, Bedford, Mass.).

Buffers. MN represents the stock buffer, which contains 25 mM MOPS and 0.02% sodium azide (W/v), pH 7.5 at 4°. MβENG is the stock buffer plus 10 mM β-mercaptoethanol, 1 mM EDTA, and 10% (v/v) glycerol. Electrophoresis sample buffer was 2% lithium dodecyl sulfate (w/V), 62.5 mM Tris, 12.5% glycerol (v/v), 2 mM EDTA, 0.001% bromphenol blue (w/v), and 20 mM dithiothreitol, pH 6.8 at 4°. CM buffer is 10 mM CAPS and 10% (v/v) methanol, pH 11.0 at 20°.

Synthesis of Radioligands. The photoaffinity ligand 2-azido-3-[$^{125}$I]iodo-7, 8-dibromodibenzo-p-dioxin and the reversible radioligand of the Ah receptor 2-[$^{125}$I]iodo-7, 8-dibromodibenzo-p-dioxin were sythesized as described previously. Kumar, V., and Chambon, P., Cell 55:145–156 (1988); Poland, A., Glover, E., Ebitino, F. H., and Kende, A. S., J. Biol. Chem. 261:6352–6356 (1986). These radioligands were prepared at specific radioactivities of 2176 Ci/mmol and were essentially pure, as indicated by RP-HPLC.

Animals and cytosol preparation. C57BL/6J mice were purchased from The Jackson Laboratory (Bar Harbor, Me.) and bred in our laboratory. Adult male and female mice were killed by cervical dislocation and their livers were removed, rinsed with ice-cold KCl (150 mM), homogenized in 9 volumes of MβENG buffer plus 5 mM EGTA, and subjected to centrifugation at 10,000×g for 20 minutes at 4° C. The postmitochondrial supernatant was carefully removed to avoid contamination by the surface lipid layer, and the membrane fraction was pelleted by centrifugation at 105,000×g for 1 hour at 4° C. The cytosolic fraction (supernatant) was separated from the surface lipids and microsomal pellet and was stored at −80° until processed further.

Photoaffinity labeling. Cytosol prepared from 300 grams of liver (total volume, 2 liters, 8–9 mg of protein/ml) was thawed in a warm water bath (37° C.) for approximately 1 hour. One twentieth of the cytosol (approximately 100 ml) was then removed and diluted with MENG buffer to 2 mg of protein/ml. The photoaffinity ligand was then added to the diluted cytosolic fraction to a final concentration of 3×10$^6$ dpm/ml, and the sample was incubated for 30 minutes at 20° C. After incubation, the unbound radioligand was removed by the addition of 10 ml of charcoal/gelatin (final concentration, 1:0.1% w/v) in MN buffer, followed by mixing with a vortex mixer (5 seconds) and incubation at 20° C. for 10 minutes. The charcoal was then removed from suspension by centrifugation at 2000×g or 10 minutes at 4° C. The supernatant was then transferred to clean tubes and the remaining fine particulate charcoal was removed by centrifugation at 10,000×g for 10 minutes at 4° C. The supernatant containing the receptor-radioligand complex was transferred to a 150-ml beaker and irradiated at 310 nm, 80 W, at 4 cm, for 1 minute, to generate the covalently labeled radioligand-receptor complex. After photolysis, β-mercaptoethanol was added to a final concentration of 10 mM to quench any remaining free radicals. The photoaffinity-labeled fraction was then pooled with the bulk of the cytosol.

Phosphocellulose chrmoatography. All ion exchange chromatography was performed in a room maintained at 4° C. The photoaffinity-labeled pooled cytosol was brought to 80 mM NaCl andloaded onto a phosphocellulose column (10-cm i.d.×14 cm; column volume, approximately 1 liter), with a flow rate of 15 cm/hr. After sample loading was complete, the flow rate was increased to 30 cm/hr and the column was washed with MβENG buffer plus 225 NaCl, with a flow rate of 30 cm/hr. The enriched fraction had a volume of 500 ml.

RP-HPLC. All RP-HPLC was performed at 56° C., using C4 silica-based columns (Vydac 214TP series; The Separations Group, Hesperia, CA) in line with cartridge precolumns (Hi-Pore Guard C4, 4.6×30 mm; Bio-Rad). The HPLC hardware consisted of two model 510 pumps interfaced with a microprocessor gradient control unit (Waters, Milford, Mass.).

SDS-PAGE, staining, and autoradlography. The efficiency of photoaffinity labeling and estimation of recoveries and purification factors were determined as follows: 100 μg of soybean trypsin inhibitor, as carrier protein, were mixed with the labeled sample and precipitated with 9 volumes of ice-cold acetone overnight at 4° C. The protein pellet was collected by centrifugation (2000×g for 10 minutes), washed with 1 ml of ice-cold acetone/water (9:1), and dissolved in electrophoresis sample buffer. The samples were then subjected to denturing electrophoresis on discontinuous slab gels (3% stacking gel, 7.5% separating gel; acrylamide/ bisacrylamide ratio=37.5:1), at 0.7 mA/cm$^2$ for 16 hours at 4° C. Laemmli, U. K., Nature (Lond). 227:680–685 (1970). The gels were routinely fixed with methanol/acetic acid stained with Commassie blue R250 (Chrambach, A., Reisfeld, R. A., Wyckoff, M., Zaccari, J., Anal. Biochem. 20:150–154 (1967)) or silver (Heukeshoven, J., and Dernick, R., *Electophoresis* 6:103–112 (1985)), dried, and placed on top of a sheet of preflashed XAR-5 film (Kodak Chemical Co., Rochester, N.Y.) backed by an intensifying screen (Cronex Lightning Plus, E.I. Dupont de Nemours Inc., Wilmington, Del.), and the film was exposed for a period of 5 to 24 hours at –60° C. before developing. The 95- and 70-kDa bands were identified in the dried gels by autoradiography and excised, and the radioactivity was quantified by a γ scintillation counting.

Protein determination. Protein concentrations were determined by the method of Warburg and Christian (Warburg, O., and Christian, W., *Biochem. Z.* 310:382–421 (1942)). The protein concentration after electrophoresis and brilliant blue-R staining was quantified by laser scanning densitometry, using phosphorylase b from the molecular weight standard mix as reference protein.

Purification. Photoaffinity labeling of the Ah receptor average 6400 dpm/mg of protein for the 95 kDa protein and 3800 dpm/mg from the 70-kDa proteolytic product (Approximately 2 fmol of photoaffinity ligand bound to receptor/mg of cytosolic protein). Assuming 100 fmol of receptor/mg or protein, this is equivalent to labeling 2% of total receptor. A fraction of the cytosolic protein (1/20th) was routinely labeled and then added back to the bulk of the cytosolic protein, to yield a preparation with a specific activity of 320 to 190 dpm/mg for the 95- and 70-kDa proteins, respectively. After phosphocellulose and DEAE-cellulose chromatography, the specific activity was increased 100-fold, with a recovery of 46%.

Because attempts at further purification of this 100-fold enriched fraction using nondenaturing means were unsuccessful, purification was continued using denaturing conditions. To reduce the protein mass, the 100-fold-enriched material on a preparative RP-HPLC column (2.2-cm i.d.×25 cm) with a large particle size (15–20 μm) was chromatographed. Using a linear gradient of acetonitrile in aqueous TFA (rate of change for acetonitrile=0.18%/cm/min), the 95-kDa receptor species eluted at 51.2% acetonitrile and the 70-kDa species eluted at 52% acetonitrile. Although resolution was inferior to that obtained with smaller particle size columns, use of the preparative column reduced protein approximately 20-fold and provided nearly complete resolution of the 95- and 70-kDa species. After multiple runs on the preparative HPLC column, fractions containing the 95-kDa species were pooled and purified further on a semipreparative column (1-cm i.d.×25 cm) with a particle size of 5 μm. Using a linear gradient of water/n-propanol, with formic acid as a modifier (rate of change for n-propanol=0.1%/cm/min), the 95-kDa receptor eluted as a sharp peak at 26.3% n-propanol.

The final HPLC step was performed on an analytical column (4.6-mm i.d.×25 cm) column with a particle size of 5 μm, using a shallow linear gradient of acetonitrile in aqueous TFA (rate of acetonitrile change=0.06%/cm/min). The elution of the 95-kDa receptor was monitored by counting the radioactivity present in the fractions and by subjecting an aliquot of each fraction to SDS-PAGE and analysis by silver staining and autoradiography. Fraction 19 contained a peak of radioactivity, but fraction 16 contained the most intense silver-straining ban at 95 kDa. For those fractions that had silver-staining material and significant radioactivity, the autoradiographic signal superimposed exactly over the silver-stained band at 95 kDa. Therefore, it was concluded that the unliganded receptor could be separated from the photoaffinity-labeled Ah receptor under the conditions employed in this final chromatography step.

HPLC fractions that contained the peak of the 95-kDa protein (as determined by silver staining) were pooled, subjected to SDS-PAGE, and electrotransferred to a PVDF membrane. The 95-kDa band was visualized on the membrane by staining with Coomassie blue R250, and the quantity of this protein was estimated by a comparison of staining intensities with known quantities of phosphorylase b. A typical experiment yielded 3–5 μg of th 95-kDa receptor from 10 grams of cytosolic protein. Final recoveries and purification factors were calculated by estimation of the protein in the 95-kDa Coomassie-stained band using laser densitometry. This method indicated a purification factor of 180,000-fold, with an overall recovery of 5%.

The above purification scheme was completed in 3 to 5 working days and yielded a purified Ah receptor of 3 to 5%.

EXAMPLE 2: NUCLEOTIDE SEQUENCE OF MURINE Ah RECEPTOR

Materials and Methods

General Methods: Cell lines (Hepa 1c1c7) were obtained from James P. Whirlock Jr. (Stanford University). Equivalent cell lines are available from the ATCC, catalogue number DRL1830. The Ah-receptor was photoaffinity labeled with [$^{125}$I]-2-azido-3-iodo-7,8-dibromodibenzo-p-dioxin. Poland, A., Glover, E., Ebetino, F. H. & Kende, A. S., *J. Biol. Chem.*, 261:6352–6365 (1986). Rabbit immunoglobulins raised against synthetic peptides corresponding to residues 12–31 and residues 233–250 were prepared and affinity purified. Poland, A., Glover, E. & Bradfield, C. A., *Mol. Pharmacol.* 39:20–6 (1991). The numbering of amino acid residues was determined by counting from the putative initiation methionine, not the true N-terminal residue of the protein (alanine #10) as determined from the amino acid sequencing. Bradfield, C. A., Glover, E. & Poland, A. *Mol. Pharmacol.* 39:13–9 (1991) .

Detection of the Ah-receptor by Immunechemical Staining and Photoaffinity Labeling.

100 μg of [$^{125}$I]-photoaffinity-labeled cytosolic protein was subjected to denaturing gel electrophoresis (SDS-PAGE) and blotted to nitrocellulose. Blots were immunostained after incubation with anti-N-terminal specific immunoglobulins (μg/ml) and goat anti-rabbit IgG linked to alkaline phosphatase. Poland, A., Glover, E. & Bradfield, C. A., Mol. Pharmacol 39:20–6 (1991). The quantity of the photoaffinity labeled receptor was determined after autoradiography by gamma-scintillation counting of the specifically labeled 95 kD bands.

DNA Cloning.

The oligonucleotide probe OL-18 was designed from the amino acid sequence lysine 16-lysine 31. See Sequence ID. NO. 1. the sequence was in the antisense direction and reads 5'TTN ATN CCT CTC N GCN GGN ATN GGT/ CTTN ACNGTT/CTTT/CTGN ACNGGT/CTT3' (SEQUENCE ID. NO. 5).

The probe OL-2 was designed from amino acid sequence lysine 16-threonine 21 reads AAA/GCCNGTNCAA/GAAA/GAC (SEQUENCE ID. NO. 6). The probe OL-27 was derived from the open reading frame (ORF) of genomic clone described below. OL-27 corresponds to the nucleotides encoding proline 26-proline 34 and reads 5'GGATTTGACTTAATTCCTTCAGGGG 3' (SEQUENCE ID. NO. 7). A genomic library was constructed in the Lambda FIX II vector and was obtained from STRATAGENE (San Diego, Calif.). The cDNA libraries were constructed in the Lambda ZAP II vector from random primed mRNA obtained from murine Hepa 1c1c7 cells. Short, J. M., Fernandez, J. M., Sorge, J. A. & Huse, W. D., *Nucleic Acids Res.* 16:7583–7600 (1988); Chirgwin, J. M., Przybyla, A. E., MacDonal, R. J. & Rutter, W. J., *Biochem.* 18:5294–5299 (1979). Library screening with degenerate oligonucleotides and cDNAs was performed. Sambrook, J., Fritsch, E. F., Maniatis, T. *Molecular Cloning: A Laboratory Manual/second edition* (Cold Spring Harbor Laboratory Press, 1989). Nucleotide sequence analysis was performed by the dideoxy-chain termination method. Sanger, F., Nicklen, S and Coulson, A. R., *Proc. Natl. Acad. Sci. USA* 74:5463–5467 (1977).

Northern Blot Analysis. RNA was located by the method of Chirgwin (Chirgwin, J. M., Przybyla, A. E., MacDonal, R. J. & Rutter, W. J., *Biochem.* 18:5294–5299 (1979)) and samples were run on 0.8% formaldehyde-agarose gels. RNA was transferred to nitrocellulose membranes and hybridized for 16 hours using either the 0.42 kb or the 1.4 kb EcoRI fragment of cAh1 at a specific activity of $1\times10^7$ cpm/µg. Sambrook, J., Fritsch, E. F., Maniatis, T. *Molecular Cloning: A Laboratory Manual/second edition* (Cold Spring Harbor Laboratory Press, 1989). Autoradiograms were routinely exposed for 4 days and then stripped and reprobed with a glyceraldehyde phosphate dehydrogenase (GAPD) probe as an internal loading control.

Characterization of the Ah-receptor in Hepa1c1c7 cells and mutants. Mutants of a murine hepatoma cell line (Hepa 1c1c7) (From James p. Whirlock, Jr.), defective in the Ah-receptor signaling pathway, were independently isolated and characterized by two research groups. Miller, A. G., Israel, D. & Whitlack, J. P., J. P., *J. Biol. Chem.* 258:3523–3527 (1983); Hankinson, O. *Somatic Cell Genet.* 9:497–514 (1983). These mutant cell lines displayed resistance or altered responses in cytochrome P450IA1 induction after exposure to Ah-receptor agonists. "Class I" mutants have a decreased level of the Ah-receptor. "Class II" mutants have normal Ah-receptor levels, but the Ah-receptor-ligand complex has a lower affinity for the nucleus. Jones, P. B. C., Miller, A. G., Israel, D. I., Galeazzi, D. R. & Whitlock, J. P., *J. Biol. Chem.*, 259:12357–12363 (1984). High activity variant (HAV) cells were also isolated. These cells appeared to have normal levels of the Ah-receptor, but the induction of the cytochrome P450IA1 gene is enhanced due to an altered cis-acting element in the promoter.

To extend proof that the photoaffinity-labeled protein was the Ah-receptor and that the N-terminal amino acid sequence data was specific to that protein, the Hepa 1c1c7 cells and derived mutants were used. See FIG. 1. The wild type, HAV cells and class II mutants show a similar amount of receptor by both methods of detection. In contrast, the class I mutants have a greater than 7-fold reduction in the levels of the Ah-receptor as compared to wild-type cells (quantitated by counting the [$^{125}$I]-photoaffinity label in the 95 kD bands). This result agreed with previous characterizations of these mutant cells in which the level of the Ah-receptor, as measured by radioligand binding, was shown to be decreased. Isreak, D. I., Whitlock, J. P., *J. Biol. Chem.* 258–1039–10394 (1983). This data demonstrates that the photoaffinity ligand specifically binds to the Ah-receptor, it confirms the identity of the purified protein as the Ah-receptor, and provided the N-terminal amino acid sequence for use in the present cloning studies.

CNBr Cleavage and Amino Acid Sequence Analysis of the Purified Ah-Receptor.

500 pmol of the purified Ah-receptor which had been purified from C57BL/6J mouse liver and covalently labeled with [$^{125}$I]-2-azido-3-iodo-7,8-dibromodibenzo-p-dioxin, was dissolved in 100 µl of 70% formic acid. CNBr was added and the cleavage reaction was carried out at room temperature, in the dark, under nitrogen, for 24 hours. The cleavage products were separated by 12% Tricine-SDS-PAGE (Schagger, G. & von Jagow, G., *Anal. Biochem.*, 166:368–379 (1987), electroblotted onto PVDF membranes, and stained with Coomassie blue dye. The major fragments were subjected to N-terminal sequencing on a pulsed liquid phase sequenator. Hewick, R. M., Hunkapillar, M. W., Hood, L. E. & Dryer, W. J., *J. Biol. Chem.*, 256:7990–7997 (1981).

EXAMPLE 3: NUCLEOTIDE SEQUENCE OF THE HUMAN Ah RECEPTOR

Methods and Materials

General Materials and Methods:

Ligand Binding of the Murine and Human Ah-receptors. Photoaffinity labeling using the ligand, [$^{125}$I]-2-azido-3-iodo-7,8-dibromodibenzo-p-dioxin (specific activity=0.5 µCi/µl), was carried out in 50 µl reactions in MENG buffer. Samples were incubated with 0.25 µCi of ligand (0.1 pmoles)+/−100 nM β-naphthoflavone 30 minutes at room temperature, cooled on ice and incubated with one fifth of charcoal/gelatin (3%/0.3% w/v) for 30 minutes on ice. The charocal/gelatin was subjected to centrifugation at 14,000 rpm for 5 minutes at 4° C. and the supernatant was irradiated with ultraviolet light at 0.8 $J/cm_2$ followed by addition of 300 mM β-mercaptoethanol. Acetone precipitates were resuspended in 1×Laemmli sample buffer and subjected to 7.5% SDS-PAGE and autoradiograph as described in Sambrook, J., Fritsch, E. F., Maniatis, T., *Molecular Cloning: A Laboratory Manual/second edition* (Cold Spring Harbor Laboratory Press, 1989).

Photoaffinity Labeling of Murine Derived Hepa 1c1c7 and Human Derived Hela Cells. Cytosolic extracts were prepared from nearly confluent cells. The cells were washed twice with PBS, scraped in 10 ml PBS, pelleted at 4° C., and resuspended in 500 µl of labeling buffer with (Hela) or without (Hepa) 10 mM sodium molybdate. The cells were homogenized with 30 strokes in a glass homogenizer and subjected to centrifugation at 14,000 rpm for 20 minutes at 4° C. The supernatants were centrifuged at 55,000 rpm for 1 hour at 4° C. 10 µg of Hepa and 60 µg of Hela cytosol were photoaffinity labeled.

Figure 12:
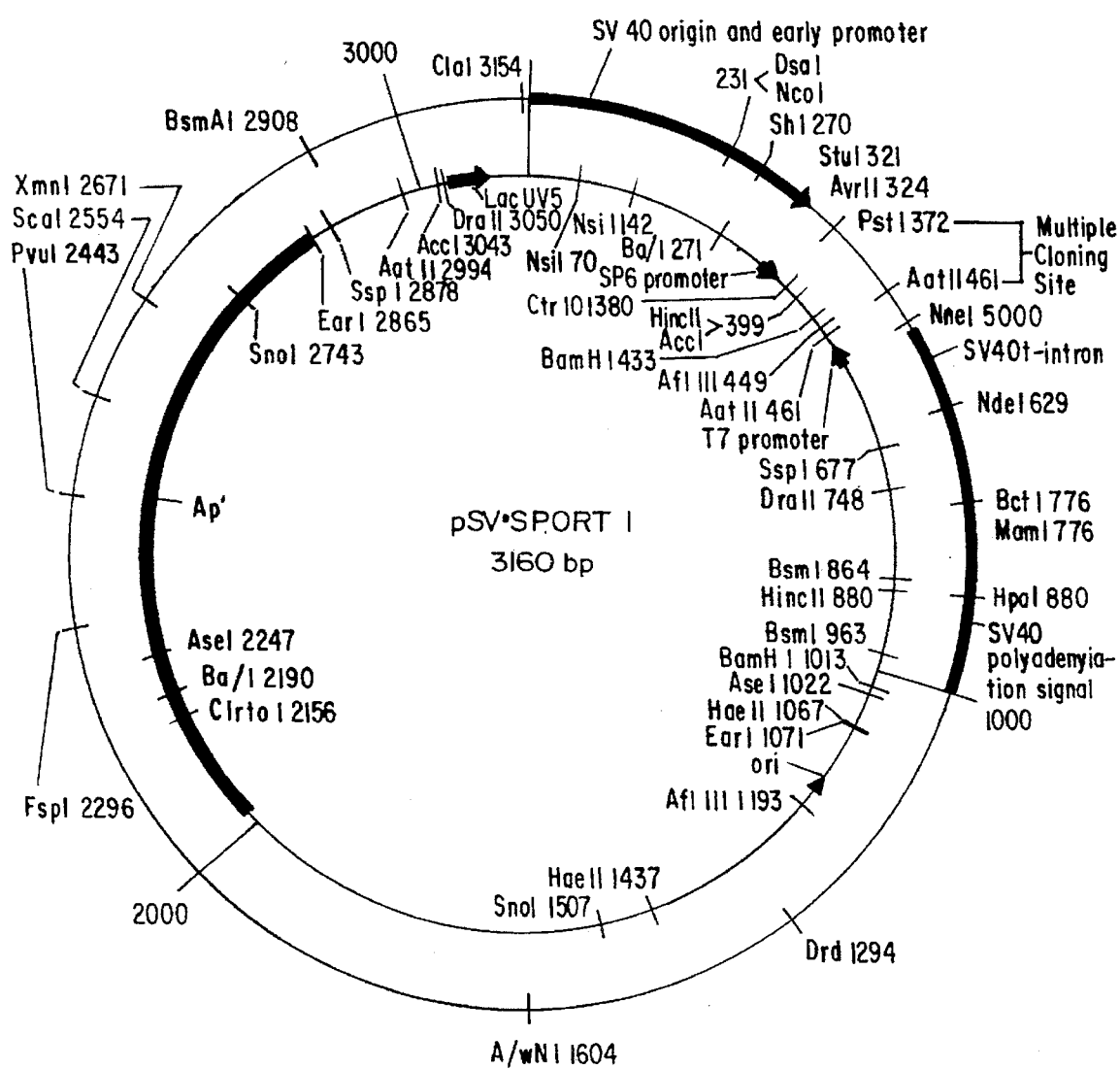
FIG. 12 shows a plasmid map of pSV.Sport1.
Figure 13:
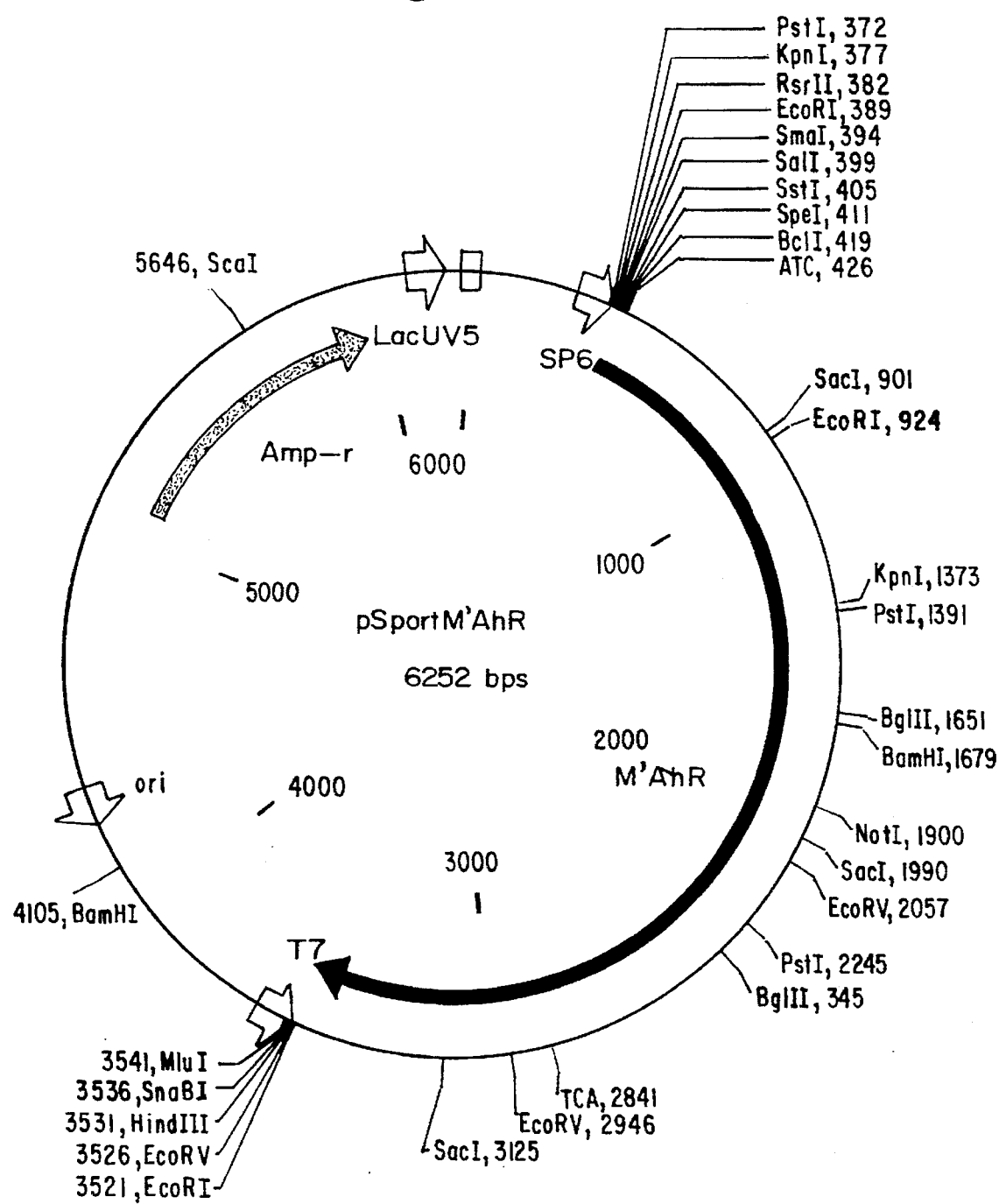
FIG. 13 shows a palsmid map of pSport M'Ahr.

Photoaffinity labeling of murine (muAhR) and human (huAhR) Ah-receptors expressed in COS-1 cells. The cells were trypsinized, pelleted, and resuspended in DME at a concentration of $4\times10^6$ cells/ml. 20 µg of pmuAhR (See FIG. 11 and SEQUENCE ID NO. 1 from 1 to 3060) or phuAhR (See FIG. 13 and SEQUENCE ID NO. 3 from 383 to 2640) plasmid DNA, plus 1.0 µg of pGL-C (luciferase transfection efficiency control, Promga) were added to 700 µl of the cell suspension in 2 mm electropotation cruvettes and incubated 5 minutes on ice. The cells were electroporated at settings of V=150 volts, C=1200 µf, and R=48 ohms and incubated 5 minutes on ice. The cells were added to 20 ml DME. At 24 hours fresh media was added to the cells. At 72 hours the cells were harvested and cytosolic extracts were prepared as above in the presence of 10 mM sodium molybdate. 60 µg of transfected COS-1 cytosols were used for photoaffinity labeling. 20 µg of the parent vector, pSV-Sport1, See FIG. 12, were used in control transfections.

Construction of the phuAhR and pmuAhR plasmids. The plasmid phuAhR was constructed by PCR using OL-135 (5'-GAAGATCTTCCAGTGGTCCCAGCCTACACC-3' Sequence ID. NO. 10) 81 nucleotides upstream of the initiation methionine and OL-136 (5'-GAAGATCTTCATGTGAACTTGCTGACGTCC-3' Sequence ID. NO. 11) 102 nucleotides downstream of the stop codon of the full length human Ah-receptor cDNA clone. The PCR-generated human Ah-receptor was then subcloned into the KpnI and SalI sites of the expression vector, pSV-Sport1 (GIBCO/BRL) and confirmed by DNA sequence analysis. The plasmid pmuAhR was constructed by sequential PCR on the murine clone, cAh1, using OL-55 (5'-GCTCTAGATGATCACCATGGTGCAGAAG-ACCGTGAAGCCCATCCCCGCTGAAGGAATTAAG-TC-3' Sequence ID. NO. 12), OL-67 (5'-GCACTAGTTGATCACCATGGCCAGCCGCAAGCGG-CGCAAGCCGGTGCAGAAGACCGTGAAGCC-3' Sequence ID. NO. 13), and OL-68 (5'-GCACTAGTTGATCACCATGAGCAGCGGCGCCAAC-ATCACCTATGCCAGCCGCAAGCGCCGCAAGC-3' Sequence ID. NO. 14) as the 5' primers add the codons for the 25 amino acids (including the initiation methionine) missing from the N-terminus of this clone. The 3' primer, OL-57 (5'GCAGAGTCTGGGTTTAGAGC-3' Sequence ID NO. 15), was downstream of the internal EcoRI site. The PCR product was then subcloned into the SpeI and EcoRI sites of the pBluescript vector (STRATAGENE) and the 2.6 kb EcoRI fragment containing the remainder of the 3' sequence of the mouse Ah-receptor was cloned into the EcoRI site. The resulting full length murine Ah-receptor clone was then subcloned into the SpeI and HindIII sites of pSV-Sport1.

In vitro transcription and translation of pmuAhR and phuAhR. Experiments were carried out using the TNT Coupled Reticulocyte Lysate System (PROMEGA). Briefly, 1 µg of plasmid DNA was added to a 50 µl reaction containing 50% TNT rabbit reticulocyte lysate, reaction buffer, 20 µM amino acid mixture minus methionine, 20 µM amino acid mixture minus leucine, 40 units RNasin, 20 units SP RNA polymerase and incubated at 30° C. for 90 minutes. pSV-Sport1 was used as a labeling control. One fifth of an in vitro reaction was used for photoaffinity labeling. The efficiency of expression was analyzed in parallel experiments utilizing $^{35}$S-methionine labeling and autoradiography and Western blot analysis using affinity-purified goat antibody raised against an N-terminal peptide derived from the murine Ah-receptor. Poland, A., Glover, E., Bradfield, C. A., *Mol. Pharmacol.* 39:20–6 (1991).

Gel shift assays demonstrating binding of Ah-receptor (AhR)-ARNT Heterodimers to DRE3. A complementary pair of synthetic oligonucleotides, 5'-TCGAGTAGATCACGCAATGGGCCCAGC-3' (SEQUENCE ID. NO. 16) and 5'-TCGAGCTGGGCCCATTGCGTGATCTAC-3' (SEQUENCE ID. NO. 17) (containing DRE3) were annealed and end-labeled with gamma $^{32}$P-labeled deoxyadenosine triphosphate as described. Sambrook, J., Fritsch, E. F., Maniatis, T., *Molecular Cloning: A Laboratory Manual/second edition* (Cold Spring Harbor Laboratory Press, 1989). Cytosolic extracts (35 µg of protein) obtained from either human SCC cells or murine Hepa 1c1c7 cells were incubated in the presenceof DMSO (−) or 20 nM TCDD (+) for 2 hours at either room temperature (human) or 30° C. (murine). Nonspecific competitor, poly dIdC, was added and incubated 15 minutes at room temperature. The radiolabeled probe was then added and incubated 15 minutes at room temperature followed by nondenaturing gel electrophoresis. In vitro translated human AhR and ARNT proteins were incubated with either DMSO (−) or 20 nM TCDD (+) for 2 hours at room temperature followed by gel shift assays as described above. In vitro translated mouse AhR and human ARNT proteins were incubated with either DMSO (−) or 20 nM TCDD (+) for 2 hours at 30° C. followed by electrophoretic mobility shift assays. Addition of excess competitor wild-type DRE3 (wt) or mutant DRE3 (m), containing two nucleotide substitutions in the core region (Neuhold, L. A., Shirayoshi, Y., Ozato, K., Jones, J. E., Nebert, D. W., *Mol. Cell. Biol.* 9:2378–86 (1989)) demonstrates specificity of complex formation.

Deletion analysis of the human and murine Ah-receptors. C-terminal deletions were constructed by PCR (CΔ313 and CΔ411 were restriction enzyme fragments utilizing internal NOtI and SpeI sites, respectively) and cloned into the pSV-Sport1 (GIBCO/BRL) expression vector. The oligonucleotides used in PCR for the construction of the deletion mutants were as follows: the human 5' primer was OL-126, 5'-GCGTCGACTGGGCACCATGAACAGCAGC-3' (SEQUENCE ID. NO. 18), which primed over the initiation methionine; the murine 5' primer was OL-68 (Sambrook, Fritsch, E. F., Maniatis, T., *Molecular Cloning: A Laboratory Manual/second edition* (Cold Spring Harbor Laboratory Press, 1989)); the 3' primers for both human and murine deletion mutants were OL-122, 5'-CCCAAGCTTACGCGTGGTTCTCTGGAGGAAGC-TGGTCTGG-3' (SEQUENCE ID. NO. 19)(CΔ636/CΔ599); OL-123, 5'-CCCAAGCTTACGCGTGGAAGTCTAG-CTTGTGTTTGG-3' (SEQUENCE ID. NO. 20)(CΔ553/CΔ516); OL-125, 5'-CCCAAGCTTACGCGTGAAGCC-GGAAAACTGTCATGC-3' (SEQUENCE ID. NO. 21) (CΔ495/CΔ458); OL-163, 5'-CCCAAGCTTACGCGTG-CAGTGGTCTCTGAGTGGCGATGATGTAATCTGG-3' (SEQUENCE ID. NO. 22) (CΔ462/CΔ425); OL-124, 5'-CCCAAGCTTACGCGTGGTCTTTGAAGTCAACCT-CACC-3' (SEQUENCE ID. NO. 23) (CΔ274/CΔ237). All PCR was carried out using the high fidelity Pfu DNA polymerase (STRATAGENE) and the sequencing of more than 4.0 kb has yielded no PCR-induced mutations. In addition, the fact that two separate clones of each deletion mutant (human and murine) produced similar results supports the fidelity of the PCR-generated deletion mutants.

All 3' primers were designed against the murine cDNA. Position of primers was based on preliminary structural analysis of protein encoded by murine Ah-receptor cDNA. N-terminal deletions representing chimeric proteins consisting of the Ah-receptor and the DNA binding domain of the yeast Gal4 protein were constructed first in the pSG424 vector (Sadowski, I., Ptashne, M., *Nucleic Acids Research* 17:7539 (1989)) and then subcloned into the pGEM-7Zf vector (PROMEGA).

EXAMPLE 4: USE OF cDNA Ah RECEPTOR IN AN ASSAY

Figure 7:
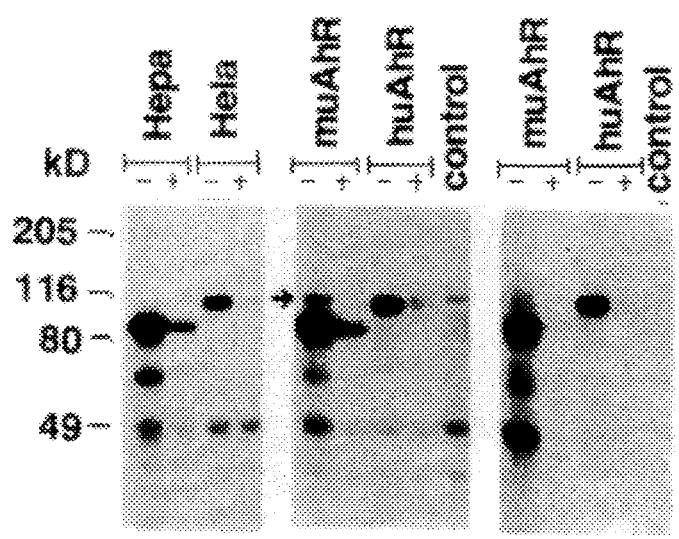
FIG. 7 shows the ligand binding of the murine and Ah receptors.
Figure 8A:
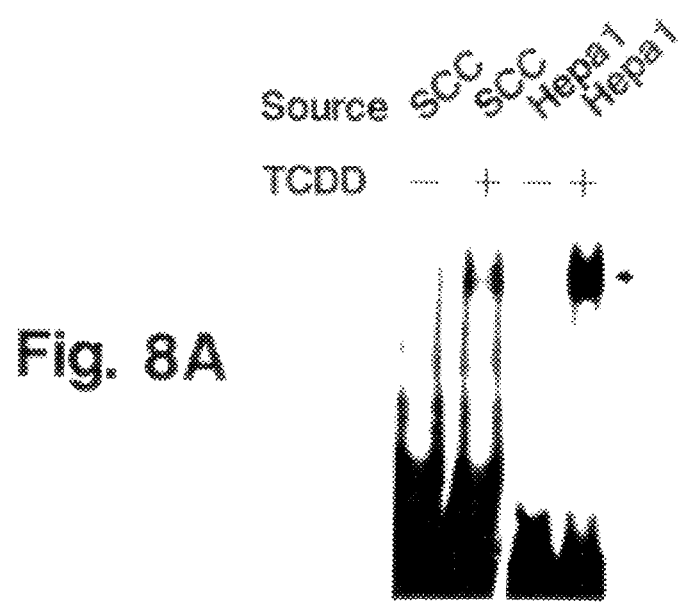
FIGS. 8A, 8B, and 8C show gel shift assays demonstrating the binding of Ah receptor (AhR)-ARNT heterodimers to DRE3.
Figure 8B:
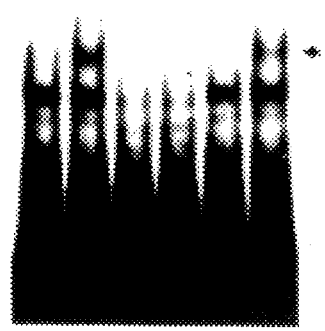
Figure 8C:

To determine if in vitro models could be developed to characterize the functional doamins of the Ah-receptor, both murine and human cDNAs in COS-1 cells were expressed and the cytosolic fractions photoaffinity labeled with the transfectants with [$^{125}$I]-2-azido-3-iodo-7, 8-dibromodibenzo-p-dioxin. Poland, A., Glove, E., Ebetiono, F. H. and Kende, A. S., *J. Biol. Chem.* 261:6352–6365 (1986). To demonstrate sepcificity of ligand binding, the reactions were performed in the presence of an excess of the receptor agonist β-naphthoflavone, which inhibited the labeling of the receptors. See FIG. 7. Since the Ah-receptor and ARNT are constitutively expressed in COS-1 cells (See FIG. 7) cDNA expression in a reticulocyte lysate system was used. Both the human and mouse receptors were specifically labeled with the photoaffinity ligand. See FIG. 7. Despite its structural similarity to the Ah-receptor, ARNT does not bind the photoaffinity ligand under the conditions used to label the receptor nor under conditions of 5-fold excess radioligand. Hoffman, E. C., et al., *Science* 252:954-8 (1991). Also, ligand binding is independent of ARNT, as ligand binding is independent of the presence or absence of ARNT. The DNA binding properties of these translated receptors were examined by employing gel shift assays using a synthetic oligonucleotide corresponding to well characterized DRE. Dension, M. S., Fisher, J. M., Whitlock, J. P., *J. Biol. Chem.* 264:16478–16482 (1989). Cytosolic extracts from human and murine cells were shown to interact with the DRE in a ligand dependent manner. See FIGS. 8A, 8B, and 8C. Similarly, in the presence of ARNT, the in vitro expressed human and murine receptors bound to the DRE upon ligand activation. See FIGS. 8A, 8B, and 8C. The specificity of DRE-binding was demonstrated by competition experiments using an excess of unlabeled DRE oligonucleotide or an oligonucleotide containing a mutated DRE. This demonstrates that both the Ah-receptor and ARNT are required for DNA binding, since neither protein was able to bind to the DRE alone.

EXAMPLE 5: YEAST STRAINS AND PLASMIDS

*S. cerevisiae* strain A303 (Mata, ura3-52, trpl$\Delta$I, his3$\Delta$200, leu2$\Delta$1) was used as a host to transform the AHR, ARNT, and the lacZ reporter gene driven by two DREs. Strain GRS4 (Mata, can1-100, ade2-1, his3-11,15,leu2-3, 12; trp1-1, ura3-1, hse82 Leu2+, hsp82 Leu2+), deleted for the hsp82 and hsc82 alleles, contains the low copy number plasmid pTT8 carrying hsp82 under the control of the galactose-inducible GAL1 promoter. Picard, D., Khuraheed, B., Garabedian, M. J., Fortin, M. G., Lindquist, S., and Yamamoto, K. R. (1990) *Nature* 348, 166–168. When grown in media containing 2% galactose, hsp82 is expressed at levels comparable to the combined wild type levels of hsc82 and hsp82. In glucose media, hsp82 is expressed at only 5% of the wild type levels. Picard, D., Khuraheed, B., Garabedian, M. J., Fortin, M. G., Lindquist, S., and Yamamoto, K. R. (1990) *Nature* 348, 166–168. The low level expression of hsp82 appears to be the result of an uncharacterized mutation allowing limited expression from the GAL1 promoter in glucose media. Picard, D., Khuraheed, B., Garabedian, M. J., Fortin, M. G., Lindquist, S., and Yamamoto, K. R. (1990) *Nature* 348, 166–168. pCW10 is a CEN6/ARS4,HIS3-marked expression plasmid containing a phosphoglycerate kinase promoter to drive expression. Poon, D., Schroeder, S., Wang, C. K., Yamamoto, T., Horikoshi, M., Roeder, R. G., and Weil, P. A. (1991) *Mol. Cell. Biol.* 11, 4809–4821. To construct the pCWhuAHR, the full-length human AHR was excised from plasmid ph$\mu$AHR2, (See Dolwick, K. M., Schmidt, J. V., Carrer, L. A., Swanson, H. I., and Bradfield, C. A. (1993) *Mol. Pharmacol.* 44, 911–917), with XmaI and cloned into the corresponding site of pCW10. pY2ARNT was constructed by digesting plasmid pBM5/NEO-M1-1 with BGmHI and subcloning the ARNT fragment into the corresponding site of the expression vector pYPGE2, a 2 $\mu$,TRP1-marked plasmid containing a phosphoglycerate kinase promoter to drive expression. See Hoffman, E. C., Reyes, H., Chu, F. P., Sander, F., Conley, L. H., Brooks, B. A., and Hankinson, O. (1991) *Science* 252, 954–958 and Brunelli, J. P. and Pall, M. L. (1993) *Yeast* 9, 1299–1808. The reporter plasmid pDRE23-Z was constructed by first subcloning the HindIII/EcoRI fragment of pGEMLS3.2, (See Denison, M. S., Fisher, J. M., and Whitlock, J. P. J. (1988) *Proc. Natl. Acad. Sci. U.S.A.* 85, 2528–2532), containing DRE2-DRE3 into pBluescriptSK (Stratagene) to generate pSKDRE23. The DRE2-DRE3 fragment was subsequently amplified by polymerase chain reaction from pSKDRE23 using 50 pmol of primers OL146 (5'-GAATTGTAATACGACTCACTATAGGG-3' SEQUENCE ID NO. 24) and OL290 (5'-CGCTCGAGAACTAGTGGATC-3' SEQUENCE ID NO. 25) in a 50-$\mu$l reaction containing 200 $\mu$m each dNTP, 2 mM MgCl$_2$, 10 mm Tris, 50 mM KCl, 0.001% gelatin (wv). The reaction was incubated at 95° C. for 5 minutes, then 72° C. for 5 minutes during which 2.5 units of Taq polymerases were added and the reaction continued at 95° C. (1 minute) then 50° C. (1 minute) and then 72° C. (1 minute) for 25 cycles. The resulting polymerase chain reaction product was digested with XhoI and cloned into the XhoI site of p2UGZ, (See Picard, D., Schena, M. and Yamamuto, K. R. (1990) *Gene(Amst.)* 86, 257–261), in the same orientation as originally found in pGEMLS3.2. pEG202 is a 2 $\mu$, HIS3-selectable plasmid containing the coding sequence for amino acids 1–202 of the bacterial repressor LexA under the control of the alcohol dehydrogenase-1 promoter. The plasmid pEGAHRN$\Delta$166, containing the AHR with amino acids 1–167 replaced by residues 1–202 of LexA, was constructed by cloning the EcoRI fragment of pSGN$\Delta$166, (See Dolwick, K. M., Schmidt, J. V., Carrer, L. A., Swanson, H. I., and Bradfield, C. A. (1993) *Mol. Pharmacol.* 44,911–917), into the EcoRI site of pEG202. The reporter plasmid pSH18-34 is a 2 $\mu$, URA3-selectabel vector containing the GAL1 promoter fused to the bacterial lacZ gene in which the UAS$_c$ has been replaced with eight LexA binding sites.

TRANSFORMATION OF THE PLASMIDS

Plasmids were sequentially transformed into the appropriate yeast strain by electroporation, (See Becker, D. M., and Guarente, L. (1991) *Methods of Enzymol.* 194, 182–187), or by a modified LiAc method (See Schiestl, R. H., and Giest, R. D. (1989) *Curr. Genet.* 16, 339–346). For electroporation, 100–500 ng of plasmid DNA was added to 50 $\mu$l or electrocompetent cells and incubated on ice for 5 minutes. The mixture was then transferred to a 2-mm cuvette and electroporated using a BTX electrocell manipulator 600 (BRX, San Diego, Calif.) at 2.5 kV, 129 ohm, for 5 ms and then immediately plated on selection plates containing 1M sorbitol and incubated at 30° C. until colonies appeared. For the LiAc protocol, a single colony of A303 cells was picked and added to 10 $\mu$l of Miniprep DNA in a sterile microcentrifuge tube. After mixing, 500 $\mu$l of PLATE solution (40% polyethylene glycol 4000, 100 mM LiAc, 10 mM Tris, pH 7.5, 1 mM EDTA) was added and the mixture incubated at room temperature overnight. Following incubation, the cell/DNA mixture was heated at 42° C. for 20 minutes and plated on selection media.

$\beta$-GALACTOSIDASE ASSAYS

For the AHR/ARNT/DRE-Z system in A303 cells, a single colony was inoculated into a 2-ml primary culture of glucose media and incubated at 30° C. overnight. Two hundred microliters of this culture was then used to inoculate a second 2-ml culture followed by addition of agonist dissolved in Me$_2$SO. Cultures were grown for 16–18 hours at 30° C. and then pelleted and resuspended in 700 $\mu$l of Z-buffer (60 mM Na$_2$HPO 40 mM NaH$_2$PO$_4$, 10 mM KCl, 1 mM MgSO$_4$ 35 mM $\beta$-mercaptoethanol). The cells were permeabilized by the addition of 50 $\mu$l of CHCl$_3$ and 50 $\mu$l of 0.1% SDS followed by vigorous vortexing for 30 seconds. Following permeabilization, 160 $\mu$l of an ONPG solution (4 mg/ml in Z-buffer) was added to each tube, mixed, and incubated at 30° C. for 20 hours. The reaction was stopped by the addition of 400 µl of 1M $Na_2CO_3$, the cell debris removed by centrifugation at 16,000×g for 10 minutes, and the $A_{420}$ of the sample was determined.

β-Galactosidase assays carried out on the AHR-LexANΔ166 chimera system were performed as above except for the following changes. Yeast strains were grown from a single colony overnight at 30° C. in 2 ml of selection medium containing either 2% glucose or 2% galactose as a carbon source. Fifty microliters of this primary culture was used to inoculate a 1-ml culture of the same media containing appropriate concentrations of agonist dissolved in $Me_2SO$. The culture was grown for 16–18 hours with vigorous shaking at room temperature. β-Galactosidase activity was determined by adding a 50-µl aliquot of the cultures to 650 µl of Z-buffer, permeabilizing the cells, and incubating with ONPG at 30° C. for 30 minutes. β-Galactosidase units were determined using the following formula: $(A_{420})/(A_{600})$ of 1/10 dilution of cells×volume of culture×length of incubation))×1000.

RESULTS

As described above, yeast strain A303 was transformed with expression plasmids containing the full-length Ah receptor, its dimerization partner ARNT, and a lacZ reporter plasmid drive by two DREs derived from the CYP1A1 promoter. The transformed yeast were exposed to various concentrations of β-napthflavone (βNF) and α-naphthoflavone (αNF) and the activity from the DRE-driven lac Z reporter measured. See FIG. 14A. The results of at least three independent experiments indicated that both βNF and αNF activated the AHR an average of 12-fold over background in a dose-dependent manner, while dexamethasone, which does not bind to the AHR, did not activate signaling. See FIG. 14B. For data presentation, the β-galactosidase units were normalized to the maximal response seen for βNF, a sigmoidal curve was constructed, and the $EC_{50}$ values generated from that curve. The $EC_{50}$ values were $7.9\pm3.6\times10^{-8}M$ and $8.0\pm0.9\times10^{-7}M$ for βNF and αNF, respectively. These values are generally within the known rank order potencies and AHR binding constants ($K_D$ values) reported for these compounds (i.e. $1.8\times10^{-9}M$ for βNF and $2.9\times10^{-8}M$ for αNF). See Knutson, J. C., and Poland, A. (1981) in *Toxicity of Halogenated Hydrocarbons* (Khan, M. A. Q., and Stanton, R. H., eds) pp. 187–201, Pergamom Press, New York. In control experiments, the inventors found that NF did not activate the lacZ reporter in cells expressing only the AHR or ARNT. Additonally, reporter gene activity was not activated by vehicle alone.

As described above, strain GRS4 was transformed with a AHR-LexAN 166 fusion plasmid, pEGAHRNΔ166 containing the chimeric Ah receptor and a LexA operator reporter plasmid pSH18-34. In this system, expression of the reporter gene was dependent on pEGAHRNΔ166 expresson and on the presence of agonist. Incubation with either βNF or βNF caused an average of 90-fold induction of lac Z activity over bacground with $EC_{50}$ values of $6.1\pm3.5\times10^{-8}$ M and $1.9\pm0.2\times10^{-6}M$, respectively. The dose-response curves obtained from this chimeric receptor system closely paralleled those of the complete AHR/ARNT/DRE pathway expressed in A303 cells. See FIG. 14C. The $EC_{50}$ of each agonist used in the chimeric system was within 1 order of the magnitude of the $EC_{50}$ values in the AHR/ARNT/DRE pathway expressed in A303 cells, indicating that the AHR-Lex A chimeria has similar pharmacology to the intact AHR.

EXAMPLE 6: MAMMALIAN STRAINS AND PLASMIDS GENERAL METHODS

The PCR was performed with annealing temperatures generally a few degrees below the calculated $T_m$ of the primers. (Delidow, B. C., Lunch, J. P., Peluso, J. P., and White, b. R. (1993) (TiDelidow, B. C., Lynch, J. P., Peluso, J. P., and White, B., eds) Humana Press, Totowa, N.J.) Template extension was performed at 72° C. using Taq polymerase and standard core reagents from Perkin-Elmer Corp. Typically, the amplified products were purified from 0.8% agarose gels and subcloned by standard molecular biology methods (Delidow, B. C., Lynch, J. P., Peluso, J. P., and White, B. R. (1993) in *PCR Protocols: Current Methods and Applications* (White, B., ed) Vol. 15 pp. 1–29, Humana Press, Totowa, N.J. 281–282). The recombinant plasmids were confirmed by a combination of restriction enzyme mapping, DNA sequencing and functional analysis of expressed proteins (Delidow, B. C., Lynch, J. P., Peluso, J. P., and White, B. R. (1993) in *PCR Protocols: Current Methods and Applications* (White, B., ed) Vol. 15 pp. 1–29, Humana Press, Totowa, N.J. 281–282; Sambrook, J., Fritsch, E. F., and Maniatis, T. (1989;) Molecular Cloning: A Laboratory Manual, Cold spring Harbor Laboratory, Cold Spring Harbor, N.Y.). In all cases, the inventors confirmed that the proteins expressed from our constructs yielded the anticipated mobilities upon SDS-polyacrylamide gel electrophoresis and Western blot analysis. The oligonucleotides used for plasmid construction are listed below.

OLIGONUCLEOTIDES (5'-3')–The oligonucleotides used were as follows: OL124, CCCAAGCTTACGCGTGGTCTTTGAAGTCAACCTCACC (SEQUENCE ID NO. 23); OL146, GAAT-TGTAATACGACTCACTATAGGG (SEQUENCED ID NO. 24); OL169, AGCTGCTTAATTAATTAAGCA (SEQUENCE ID NO. 26); OL170, AGCTTGCTTAAT-TAATTAAGC (SEQUENCE ID NO. 27); OL180, GCGTC-GACTGATGAGCAGCGGCGCCAACATCACC (SEQUENCE ID NO. 28); OL202, CATTACTTATCTA-GAGCTCG (SEQUENCE ID NO. 29); OL209, GATTTAG-GTGACACTATAG (SEQUENCE ID NO. 30); OL227, GATAAGAATGCGGCCGCACGGATCCAG-CAGCAACAGCAAACAGAATTGG (SEQUENCE ID NO. 31); OL231, ATAAGAATGCGGCCGCAGC-CCCCCCGACCGATGTCAGC (SEQUENCE ID NO. 32); OL232, ATAGTTTAGCGGCCGCCCCACCG-TACTCGTCAATTCC (SEQUENCED ID NO. 33); OL258, GCCGTCGACGCGGCCGCGAAGTCTAGCT-TGTGTTTGG (SEQUENCE ID NO. 34); OL263, ATAA-GAATGCGGCCGCACCCTCAATGTTGTGTCGGG (SEQUENCE ID NO. 35); OL291; CGGGATCCTCGCG-GCCGCAGAGAATTTCAGGAATAGTGGC (SEQUENCE ID NO. 36).

PLASMID CONSTRUCTION

All Gal4 fusion plasmids were constructed in the pSG424 vector (Sadowski, and Ptashner, M. (1989) *Nucleic Acids Res.* 17, 7539). This vector contains the amino-terminal 147 amino acids of the yeast Gal4 protein under the control of the SV40 promoter, followed by a multiple cloning site that allows in-frame cloning of sequences derived from a second cDNA. The plasmid pSport3 was prepared by cloning a universal termination fragment, OL169 and OL170 (annealed) into the HindIII site of pSV-Sport1 (Van Doren, K., Hanahan, D., and Gluzman, Y. (1984) *J. Virol.* 50, 606–61). The names of all Gal4 fusion plasmids start with the prefix "pG," indicating that the first 147 amino acids are from Gal4. The amino and carboxyl-terminal deletions are indicated by "NΔ" or "CΔ," respectively. The numbers in the plasmid names correspond to the number of amino acids deleted from either the amino terminus or the carboxyl terminus.

GAl4-AHR FUSION CONSTRUCTS

The plasmids pGAHRNΔ166, pGAHRNΔ315, pGAHRNΔ409/CΔ165, and pGAHRNΔ520 were generated from the EcoRI, KpnI, BglII, and SacI restriction enzyme fragments of the murine AHR derived from the plasmid pcAHR (See Dolwick, K. M., Swanson, H. L. and Bradfield, C. A. (1993) *Proc. Natl. Acad. Sci., U.S.A.* 90, 8566–8570), respectively, and subcloned into the compatible sites of pSG424. The plasmid pGAHRNΔ520/CΔ165 was generated by cloning the SacI restriction enzyme fragment of pGAHRNΔ409/CΔ165 into the corresponding site of pSG424. To generate pGAHR, a 2.2-kilobase pair KpnI fragment of pcAHR was subcloned into the KpnI site of PGAHRNΔ315. To construct pGAHRCΔ516, the plasmid pmuAHR (See Dolwick, K. M., Swanson, H. L. and Bradfield, C. A. (1993) *Proc. Natl. Acad. Sci., U.S.A.* 90, 8566–8570) was first amplified with OL258 and OL209 using PCR, and the amplified product was subcloned into the SalI/NotI sites of pSport3 to yield pSport3CΔ516. Then, pSport3CΔ516 was PCR amplified with OL180 and OL146 (a vector-specific T7 primer), and the amplified product was subcloned into SalI/XbaI sites of pSG424 to yield pGAHRCΔ516. The plasmid PGAHRNΔ409 was constructed by subcloning the 1.1-kilobase pair SacI fragment of pGAHRNΔ520 into the corresponding site of pGAHRNΔ409/CΔ165. The plasmid pGAHRNΔ315/CΔ284 was constructed by deleting the SacI fragment from pGAHRNΔ315. To construct the plasmid pGAHRCΔ516/VP, the transactivation domain of the herpes simplex virus VP16 protein (See Ptashne, M. (1988) *Nature* 335, 683–689; Triezenberg, S. J., Kingsburgy, R. C., and McKnight, S. L. (1988) *Genes & Dev.*, 2, 718–729) was PCR amplified with OL231 and OL232 and subcloned into the NotI site of pGAHRCΔ516.

GAl4-ARNT FUSION CONSTRUCTS

The ARNT constructs presented in this report were derived from pBM5NeoM1-1, which does not contain the amino-terminal 15-amino acid alternatively splices exon (See Hoffman, E. C., Rayes, H., Chu, F. F., Sander, F., Conley, L. H., Brooks, B. A., and Mankinson, O. (1991) *Science* 252, 954–958). The absence of this alternatively splices exon has previously been shown to have not effect on ARNT signaling (See Hoffman, E. C., Rayes, H., Chu, F. F., Sander, F., Conley, L. H., Brooks, B. A., and Mankinson, O. (1991) *Science* 252, 954–958). The plasmid pGARNT was constructed by cloning the BamHI fragment from phuARNT (See Dolwick, K. M., Schmidt, J. V., Carver, L. A. Swanson, H. L, and Bradfield, C. A. (1993) *Mol. Pharmacol*, 44, 911–917) into the corresponding sites of pSG424. The plasmid pGARNTNΔ487 was constructed by PCR amplifying phuARNT with OL227 and OL146 and subcloning the amplified product into the BamHI sites of pSG424. The plasmid pGARNTNΔ581 was constructed by cloning a PCR-amplified fragment (using OL291 and OL202) from pGARNTNΔ487 into the BamHI site of pSG424. The plasmid pGARNTNΔ581/A604–697 was constructed by removal of the 282-base pair PstI fragment from pGARNTNΔ581. The plasmid pSportARNTCΔ418 was constructed by cloning a PCR-amplified product from phuARNT (using OL209 and OL263) into the SalI/NotI sites of pSport3. The plasmid pGARNTCΔ418 was constructed by cloning the 1.1-kilobase pair BamHI fragment of pSportARNTCΔ418 into the corresponding site of pSG424. The plasmid pGARNTCΔ418/VP was constructed by cloning the NotI-digested VP16TAD (see above) fragment into the corresponding site of PGARNTCΔ418. The plasmid pGARNTCΔ673 was constructed by removal of the 600-base pair KpnI fragment from pGARNTCΔ418.

CELL CULTURE AND TRANSIENT TRANSFECTION

COS-1 cells were maintained in Dulbecco's modified Eagle's medium supplemented with 10% heat-inactivated bovine calf serum, 100 units/ml penicillin, 100 µg/ml streptomycin, and 2.5 µg/ml fungizone at 37° C. in a humidified 10% $CO_2$ atmosphere. For transient transfections, subconfluent COS-1 cells were trypsinized, pelleted, and resuspended in Dulbecco's modified Eagle's medium at a concentration of approximately $4 \times 10^6$ cells/ml. Ten micrograms of Gal4 fusion plasmids, 10 µg of pG5BCAT (CAT reporter plasmid containing five $UAS_G$ elements upstream of the adenovirus E1B TATA box core promoter, (See Lillie, J. W., and Green, M. R. (1989) *Nature* 338, 39–44)), and 1.0 µg of pCH110 (β-galactosidase transfection efficiency control plasmid, (See Herbomel, P., Bourachot, B., and Yaniv, M. (1984) *Cell* 39, 653–662)) was added to 350 µl (approximately $1 \times 10^6$ cells) of the suspension in 2-mm electroporation cuvettes and incubated for 5 minutes on ice. After electroporation (BTX Electro Cell Manipulator 600, Biotechnologies and Experimental Research Inc.; at settings of V=150 volts, C=1200 microfarads, and R=48 ohms), cells were incubated for 5 minutes on ice, diluted with 600 µl of Dulbecco's modified Eagle's medium, and then plated in 60-mm sterile dishes containing 4 ml of media. After 24 hours fresh medium was added, and at 48 hours the cells were harvested. Constructs that were being tested for agonist dependence were incubated in the presence of either 5 µl of βNF (1 µm) in dimethylsulfoxide, or 5 µl of dimethylsulfoxide 24 hours after transfection. To harvest, the cells were washed twice with phosphate-buffered saline, scraped in 1 ml. of phosphate-buffered saline, centrifuged for 2 minutes at 16,000×g at 4° C., and then resuspended in 100 µl of 0.25×Tris (pH 7.8). Extracts were made by four freeze/thaw cycles of 3 minutes each in a dry ice/ethanol bath and a 37° C. water bath. The soluble fraction of the extracts was then collected by centrifugation at 16,000×g at 4° C. for 5 minutes and stored at −80° C. until ready for analysis.

β-GALACTOSIDASE AND CAT ASSAYS

For β-galactosidase assays, 20 µl of cell extract was incubated with 2×assay buffer (120 mM $Na_7HPO_4$, 80 mM $NaH_7PO_4$, 2 mM $MgCl_2$, 100 mM β-mercaptoethanol, and 1.33 mg,ml o-nitrophenyl β-o-galactopyranoside) in a 300-µl reaction volume at 37° C. for 30 minutes. The reaction was stopped with 500 µl of 1M $Na_2CO_3$, and the absorbance of 420 nm was determined. For CAT assays, the quantity of cell extract used was normalized to transfection efficiency based on the results of the β-galactosidase assays. Assays for CAT activity were carried out 100-µl reaction volumes (See Gorman, C. M., Moffiat, L. F., and Howard, B. H. (1982) *Mol. Cell. Biol.* 2, 1044–1051) by incubating the extracts with 0.8 mM acetyl-CoA, 0.25 µCi[$^{14}$C]chloramphenicol, and 1M Tris (pH 7.8) for 45 minutes at 37° C. The reactions were extracted with 1 ml of ethyl acetate, and the organic phase was dried under vacuum and resuspended in 30 µl of ethyl acetate. The products were resolved on silica gel thin-layer chromatography sheets (Eastman Kodak Co.) using a chloroform/methanol (190:10 (v/v)) solvent and analyzed on a Fuji BAS 2000 phosphor imaging system. The activity as converted to counts/min. using known amounts of

[¹⁴C]chloramphenicol as standards. Samples generating products beyond the linear range of the assay were appropriately diluted and reanalyzed. Each construct was tested at least twice in independent experiments, and the standard error was never more than 25%. Fold increase in CAT activity was calculated by dividing the percent acetylation resulting from each test plasmid by percent acetylation of the control pSG424.

Indirect Immunoflourescence Microscopy—Immunocytochemistry was performed essentially as described, Ausubel, F. M., Brent, R., Kingston, R. E., Moore, D. D., Seidman, J. G., Smith, J. A., and Struhl, K. (1991) *Current Protocols in Molecular Biology*, Vol. 2, Greene Publishing Associates and Wiley-Interscience, New York, N.Y. and Alvares, K., Widrow, R. J., Abu-Jawdeh, J. M., Schmidt, J. V., Yeldandi, A. V., Rao, M. S., and Reddy, J. K. (1992) *Proc. Natl. Acad. Sci. U.S.A.* 89:4908–4912. Briefly, cells were harvested by trypsinization 48 h after tranfection, placed onto glass slides by centrifugation at 89×g (Cytospin2, Shandon Instruments), fixed and permeabilized with methanol at −20° C. for 20 minutes, blocked with 3% bovine serum albumin in phosphate-buffered saline, incubated overnight at 4° C. with the primary antibody at 1:100 dilution in 3% bovine serum albumin/phosphate-buffered saline, washed and inucbated with fluoroscein isothiocyanate-linked secondary antibody (Jackson Immunoresearch), and viewed with a Ziess microscope equipped for epifluorescence microscopy (Carl Ziess Inc.). The position of the nuclei was confirmed by parallel phase contrast microscopy.

RESULTS

Figure 15:
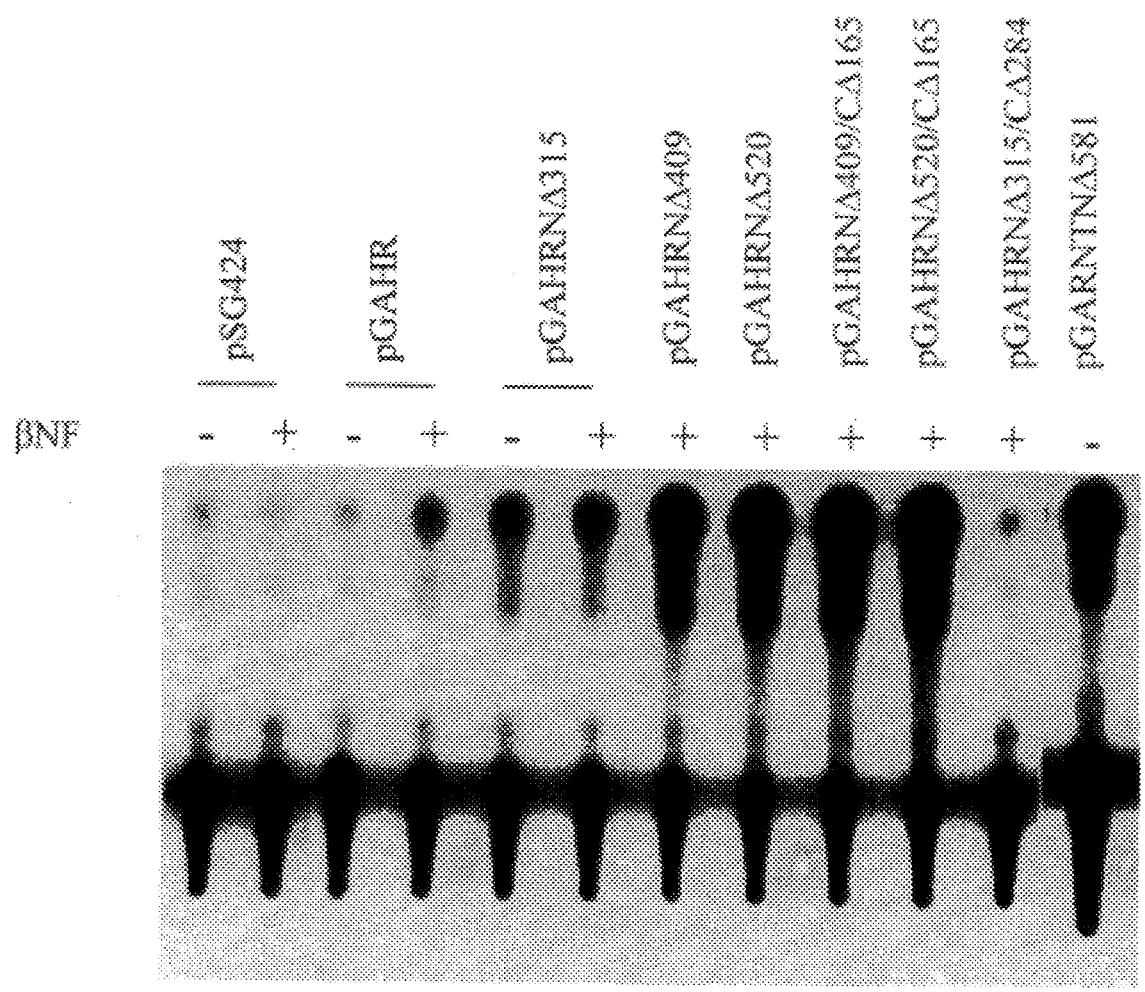
FIG. 15 shows a representative CAT assay of extracts from cells tranfected with selected Gal4-fusion chimeras. The (−) means without βNF, the (+) means with βNF. Due to the high level of activity, extracts from the following plasmids were diluted 10-fold:pGAHRNΔ409, pGAHRCΔ418/VP, pGAHRNΔ520. Extracts from plasmids pGAHRNΔ409/CΔ165 and pGARNTNΔ581 were diluted 20-fold.

A representative CAT assay is shown in FIG. 15. FIG. 15 shows assays of extracts from cells tranfected with selected GAL14-fusion chimeras. To control for variability in tranfection efficiencies between samples, all extracts that were used for CAT assays were normalized to the expression of a cotranfected β-galactosidase control (pCH110). Jain et al., "Potent Transactivation Domains of the Ah Receptor and the Ah Receptor Nuclear Translocator Map to Their Carboxyl Termini," *J. of Bio. Chem.*, 269:1–7 (1994), hereby incorporated by reference.

Figure 16:
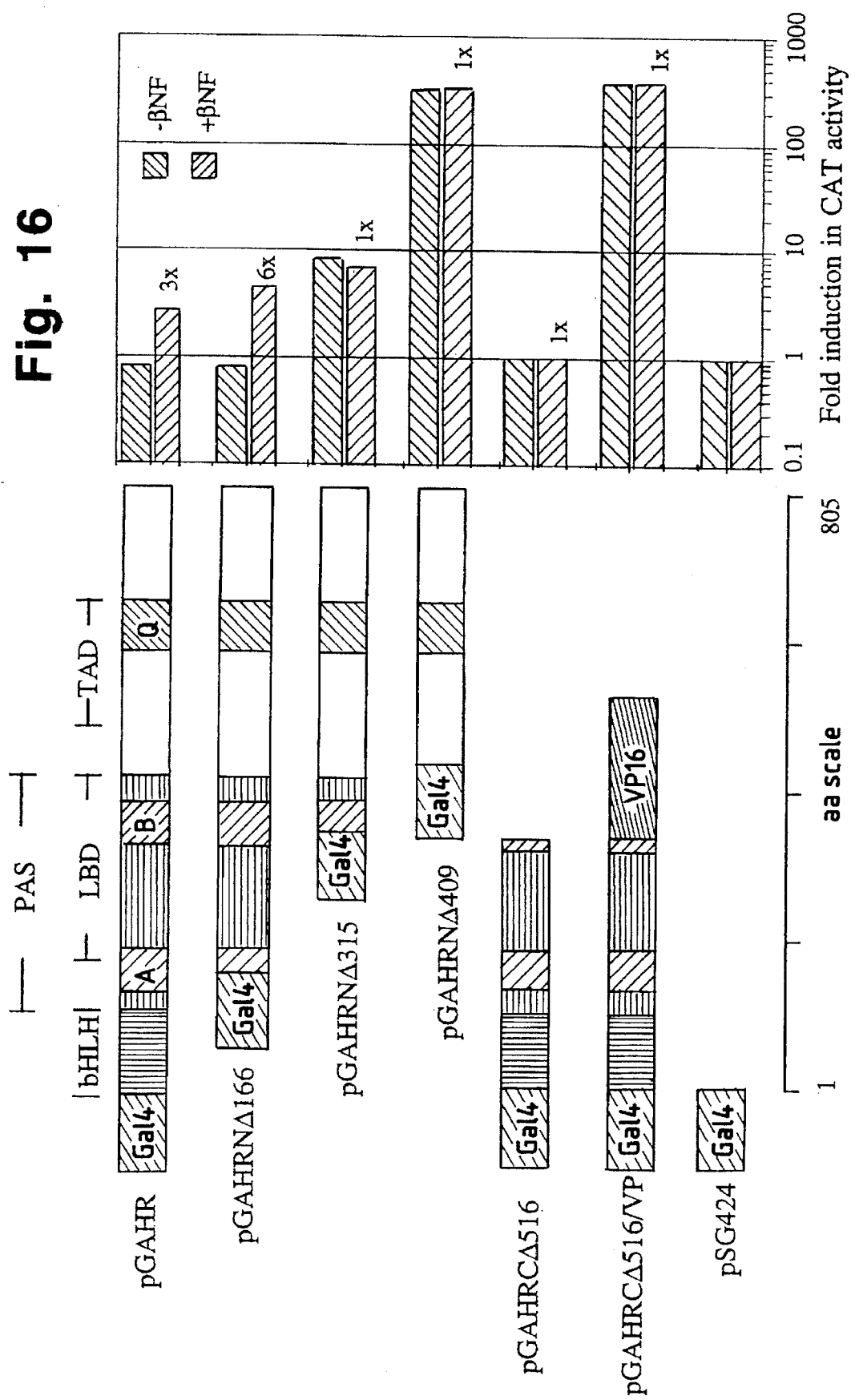
FIG. 16 shows a schematic diagram of amino - and carboxyl-terminal deletion GAL4-AHR fusion constructs and the average of their CAT assay results. The values reported are the average of two to four independnt experiments with standard error never greater than 25%. The box marked GAL4 represents yeast GAL4 (1–147 amino acids) vertical bars represent the basic helix loop helix (bHLH) the stripped box represents the PAS domain with the "A" and "B" repeats indicated therein with black boxes (2); box with left-to-right diagonal ines represents the glutamine-rich region (Q) and the gray shaded box corresponds to TAD of the herpes simplex virus VP16 protein (VP16). The positions of the PAS, ligand binding domina, and TAD are indicated with horizontal bars. Fold induction, reported in the bar graph on the right, is relative to the control pS6424. Bars with a gray diagonal ines represent experiments without βNF, and black bars are those with βNF. Ligand-dependent induction is indicated to the right of bars when relevant.

FIG. 16 contains a schematic diagram of the amino- and carboxyl terminal deletion of the following Gal4-AHR fusion constructs and the average of their CAT assay results: pGAHR, pGAHRNΔ166, pGAHRNΔ315, pGAHRNΔ409, pGAHRCΔ516, and pGAHRCΔ516/VP. In an attempt to define the boundaries of the ligand binding domain of the AHR, the inventors decided to examine the impact that ligand has on constructs containing residues 166 and 388. The inventors observed that all Gal4 chimeras fused to the complete ligand binding domain of the AHR drove CAT expression in a ligand—dependent manner (pGAHR and pGAHRNΔ166) and that all fusions lacking this domain did not retain ligand responsiveness. The ligand responsiveness of these constructs is consistant with previous observations demonstrating the modular nature of the AHR, the independence of the ligand binding domain from surrounding sequences, and the potential for this region to confer ligand responsiveness on a glucocorticord receptor/AHR chimera. An additional important observation was that ARNT was not required to obtain ligand responsiveness of these chimeras.

EXAMPLE 7: PROTOCOL FOR PLATE β-GALACTOSIDASE ASSAY FOR DETECTING AGONSITS TO THE Ah RECEPTOR IN ENVIRONMENTAL SAMPLE

1. To assay for AHR agonists, the yeast reporter strain should be plated to agar plates containing the appropriate concentration of the compound under study and incubated 2–3 days until colonies appear.

2. β-galactosidase activity can be approximated by overlaying the plates with 10 ml of solution containing 0.5% agarose/0.5M sodium phosphate, pH=7/0.1% sodium dodecyl sulfate/2% (vol/vol) dimethylformimide/0.05% 5-bromo-4-chloro-3-indolyl β-D-galactopyranoside (X-gal).

3. Incubate plates at room temperature for 4 to 18 hours or at 37° C. until blue color appears.

EXAMPLE 8: PROTOCOL FOR AHR INDUCTION—LIQUID ASSAY FOR DETECTING AGONISTS TO THE Ah RECEPTOR IN ENVIRONMENTAL SAMPLES

A. Set up primary culture.

1. Aliquot 1–2 ml of liquid media into a sterile 10 ml culture tube (round bottomed—not conical—is best to ensure adequate aeration during growth).

2. Using a sterile toothpick of flamed loop, inoculate media with a single, well isolated colony from the plate.

3. Incubate overnight 16–18 hours at 30° C. with shaking (300 rpm). You should see a dense growth of cells ($OD_{600}$>1).

B. Set up secondary culture.

1. Aliquot i ml of liquid media to sterile, round bottomed culture tubes.

2. Inoculate each tube with 50 µl of cells from primary culture.

3. Add 10 µl of 100 nM βNF solution (1 µM final concentration or 10 µl DMSO (vehicle control) to the 1 ml of secondary culture.

4. Grow secondary culture at room temperature for 16 hours with vigorous shaking (300 rpm).

β-galactosidase assay—Liquid Assay

1. For each assay you will need 2 microfuge tubes.

Into one tube, aliquot 650 µl of Z-buffer. This tube, Tube A, will be used for the colorimetric assay. To the second tube, aliquot 450 µl Z-buffer. This tube, Tube B, will be used to determine the cell density of the secondary culture.

2. To both Tube A and Tube B, add 50 µl of cells from the secondary culture. Tube B can be closed and set aside for later.

3. To Tube A, add 50 µl 10.1% sodium dodecyl sulfate (SDS) and 50 µl chloroform. Vortex at top speed for 30 seconds to permeabilize cells.

4. Add 160 µl ONPG solution. Close tube, vortex briefly to mix and place at 30° C. until color develops in positive tubes, about 20–30 minutes.

5. Quench reaction with 400 µl 1M $Na_2CO_3$. Invert tubes several times to mix. Addition of $Na_2CO_3$ may cause yellow color to deepen.

6. Spin tubes in microfuge 12,000–16,000×g for 5 minutes to remove cell debris.

7. Measure optical density in a spectrophotometer.

Blank against Z-buffer

Tube A and 420 nm

Tube B at 600 nm

If the $OD_{420}$ of Tube A is >1, dilute sample 1:10 and reread. If the $OD_{420}$ of a 1:10 dilution of Tube A is >0.5 the reaction exceeded to linear range of the assay. Repeat assay and quench the $Na_2CO_3$ at an earlier time point.

8. Calculate β-galactosidase units.

$$\frac{(OD420) * 100}{(OD600 \text{ of } 1:10 \text{ dilution of cells})*(\text{length of incubation in min.})*(\text{vol of culture used in ml})}$$

Sample calculation
    50 µl of secondary culture assayed
    25 min. incubation at 30° C.
    OD420 of sample = 1.789
        OD420 > 1 so dilute sample 1:10 in Z-buffer
        OD420 of 1:10 dilution = 0.161
    OD600 of sample = 0.201

$$\frac{(0.161)*(10)*(100)}{(0.201)*(25)*(0.50)} = 640.8 \text{ units}$$

The above protocol can be modified for use with mammalian cells.

Although the invention has been described in terms of the specific embodiments many modifications and variations of the present invention are possible in light of the teachings. It is, therefore, to be understood that within the scope of the appended claims the invention may be practiced otherwise than as specifically described.

We claim:

1. A genetically engineered viable yeast cell transformed with plasmids expressing an Ah receptor protein having an amino acid sequence corresponding to Seq. ID. No. 4, an Ah receptor nuclear translocator, a dioxin responsive element and a reporter gene, wherein the reporter gene detects the activation of the Ah receptor upon the binding of agonists to the Ah receptor.

2. The yeast cell of claim 1 wherein said yeast cell is selected from the group consisting of *Saccharomyces cerevisiae* and *Saccharomyces pombe*.

3. The yeast cell of claim 1 wherein the reporter gene is lac Z.

4. A genetically engineered viable yeast cell transformed with plasmids expressing a chimeric Ah receptor, said chimeric Ah receptor comprising an Ah receptor having an amino acid sequence corresponding to Seq. ID. No. 4 and having its DNA binding and dimerization domain replaced with the analogous domain from a protein capable of binding DNA sequences, an operator sequence comprising the binding sites from the binding domain of the protein used to replace the binding domain of the Ah receptor, and a reporter gene for detecting the activation of the chimeric Ah receptor upon the binding of agonists to said chimeric Ah receptor.

5. The yeast cell of claim 4 wherein the yeast is selected from the group consisting of *Saccharomyces cerevisiae* and *Saccharomyces pombe*.

6. The yeast cell claim 4 wherein the DNA binding and dimerization domain of the Ah receptor is replaced with the DNA binding and dimerization domain from a LexA protein.

7. The yeast cell of claim 4 wherein the operator is Lex A operator.

8. The yeast cell of claim 4 wherein the reporter gene is lac Z.

9. A genetically engineered viable mammalian cell transformed with plasmids expressing a chimeric Ah receptor, said chimeric Ah receptor comprising an Ah receptor having an amino acid sequence corresponding to sequence ID. No. 4 having its DNA binding and dimerization domain replaced with the analogous domain from a protein capable of binding DNA sequences, an operator sequence comprising the binding sites from the binding domain of the protein used to replace the binding domain of the Ah receptor, and a reporter gene for detecting the activation of the chimeric Ah receptor upon the binding of agonists to said chimeric Ah receptor.

10. The mammalian cell of claim 9 wherein the mammalian cell is a COS-1 cell.

11. The mammalian cell of claim 9 wherein the DNA binding and dimerization domain of the Ah receptor is replaced with the DNA binding and dimerization domain from a Gal4 protein.

12. An assay for detecting agonists to an Ah receptor in environmental samples, the assay comprising the steps of:
    a) preparing a culture of the genetically engineered viable cell of claims 1, 4, or 9;
    b) incorporating a sample to be tested into the culture containing the cell of step a;
    c) growing the culture for several hours;
    d) determining Ah receptor activation by detecting reporter gene expression; and e) detecting agonists based on Ah receptor activation.

13. The assay of claim 12 wherein the cell is a yeast cell.

14. The assay of claim 12 wherein the cell is a mammalian cell.

15. The assay of claim 12 wherein the environmental sample is a water sample.

16. The assay of claim 12 wherein the environmental sample is a air sample.

17. The assay of claim 12 wherein the environmental sample is a soil sample.

* * * * *